US011939618B2

(12) United States Patent
Lee et al.

(10) Patent No.: US 11,939,618 B2
(45) Date of Patent: Mar. 26, 2024

(54) FUSION PROTEINS USEFUL FOR MODIFYING TERPENES

(71) Applicant: The Regents of the University of California, Oakland, CA (US)

(72) Inventors: Taek Soon Lee, Berkeley, CA (US); Xi Wang, Emeryville, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 255 days.

(21) Appl. No.: 17/207,097

(22) Filed: Mar. 19, 2021

(65) Prior Publication Data

US 2021/0292797 A1   Sep. 23, 2021

Related U.S. Application Data

(60) Provisional application No. 62/993,629, filed on Mar. 23, 2020.

(51) Int. Cl.
| | |
|---|---|
| *C12P 17/08* | (2006.01) |
| *C12N 9/02* | (2006.01) |
| *C12N 9/88* | (2006.01) |
| *C12P 5/00* | (2006.01) |

(52) U.S. Cl.
CPC ............ *C12P 5/007* (2013.01); *C12N 9/0073* (2013.01); *C12N 9/88* (2013.01); *C07K 2319/00* (2013.01); *C12Y 114/13106* (2013.01); *C12Y 114/14* (2013.01)

(58) Field of Classification Search
CPC ............ C12P 17/08; C12P 15/00; C12N 9/88
See application file for complete search history.

(56) References Cited

U.S. PATENT DOCUMENTS

| | | |
|---|---|---|
| 4,500,707 A | 2/1985 | Caruthers et al. |
| 4,683,195 A | 7/1987 | Mullis et al. |
| 5,436,327 A | 7/1995 | Southern et al. |
| 5,700,637 A | 12/1997 | Southern |
| 11,180,782 B2 * | 11/2021 | Kumaran .................. C12P 7/26 |

OTHER PUBLICATIONS

Boutanaev et al. Investigation of terpene diversification across multiple sequenced plant genomes, PNAS : E81-E88, (2014). (Year: 2014).*
Aharoni et al., "Volatile Science? Metabolic Engineering of Terpenoids in Plants." Trends Plant Sci. 2005, 10 (12), 594-602 (2005).
Chang et al., "Engineering *Escherichia coli* for Production of Functionalized Terpenoids Using Plant P450s." Nat. Chem. Biol. 3, 274-277 (2007).
Renault et al., "Cytochrome P450-Mediated Metabolic Engineering: Current Progress and Future Challenges." Curr. Opin. Plant Biol. 19, 27-34 (2014).
Van Beilen et al., "Biocatalytic Production of Perillyl Alcohol from Limonene by Using a Novel *Mycobacterium* Sp. Cytochrome P450 Alkane Hydroxylase Expressed in Pseudomonas Putida." Appl. Environ. Microbiol. 71 (4), 1737- 1744 (2005).
Alonso-Gutierrez et al., "Metabolic Engineering of *Escherichia coli* for Limonene and Perillyl Alcohol Production." Metab. Eng. 19, 33 41 (2013).
Conrado et al., "Engineering the Spatial Organization of Metabolic Enzymes: Mimicking Nature's Synergy." Curr. Opin. Biotechnol. 19 (5), 492-499 (2008).
Meynial Salles et al., "Evolution of a *Saccharomyces cerevisiae* Metabolic Pathway in *Escherichia coli*." Metab. Eng., 9 (2), 152-159 (2007).
Kourtz et al., "A Novel Thiolase-Reductase Gene Fusion Promotes the Production of Polyhydroxybutyrate in *Arabidopsis*." Plant Biotechnol. J., 3 (4), 435-447 (2005).
Dueber et al., "Synthetic Protein Scaffolds Provide Modular Control over Metabolic Flux." Nat. Biotechnol. 27 (8), 753-759 (2009).
Avalos et al., "Compartmentalization of Metabolic Pathways in Yeast Mitochondria Improves the Production of Branched-Chain Alcohols." Nat. Biotechnol. 31, 335-341 (2013).
Yu et al., "Synthetic Fusion Protein Design and Applications." Biotechnol. Adv. 33 (1), 155-164 (2015).
Sarria et al., "Microbial Synthesis of Pinene." ACS Synth. Biol. 3 (7), 466-475 (2014).
Gao et al., "Engineering the Methylerythritol Phosphate Pathway in Cyanobacteria for Photosynthetic Isoprene Production from CO2." Energy Environ. Sci. 9 (4), 1400-1411 (2016).
Zuo et al., "Engineered P450 Biocatalysts Show Improved Activity and Regio-Promiscuity in Aromatic Nitration." Sci. Rep. 7 (1), 842 (2017), 9 pages.
Girvan et al., "Applications of Microbial Cytochrome P450 Enzymes in Biotechnology and Synthetic Biology." Curr. Opin. Chem. Biol. 31, 136-145 (2016).
Munro, A. W.; Girvan, H. M.; Mason, A. E.; Dunford, A. J.; McLean, K. J. What Makes a P450 Tick? Trends Biochem. Sci. 38 (3), 140-150 (2013).
Shaw et al., "Identification of a Fungal 1,8-Cineole Synthase from *Hypoxylon* Sp. with Specificity Determinants in Common with the Plant Synthases" J. Biol. Chem. 290 (13), 8511-8526 (2015).
Yang et al., "Highly Efficient Conversion of Terpenoid Biomass to Jet-Fuel Range Cycloalkanes in a Biphasic Tandem Catalytic Process." Green Chem. 19 (15), 3566-3573 (2017).
Bergman et al., "Metabolic Engineering Strategies to Convert Carbohydrates to Aviation Range Hydrocarbons;" Chuck, C. J. B. T.- B. for A., Ed.; Academic Press, pp. 151-190 (2016).
Mendez-Perez et al., "Production of Jet Fuel Precursor Monoterpenoids from Engineered *Escherichia coli*." Biotechnol. Bioeng. 114 (8), 1703-1712 (2017).
Leita et al., "Production of P-Cymene and Hydrogen from a Bio-Renewable Feedstock-1,8-Cineole (Eucalyptus Oil)." Green Chem. 12 (1), 70-76 (2010).

(Continued)

*Primary Examiner* — Tekchand Saidha
(74) *Attorney, Agent, or Firm* — Robin C. Chiang; LAWRENCE BERKELEY NATIONAL LABORATORY

(57) ABSTRACT

The present invention provides for a fusion protein comprising: (a) a terpene synthase (TS), or a homolog thereof, (b) a peptide linker, and (c) a P450 enzyme, or a homolog thereof.

22 Claims, 12 Drawing Sheets

Specification includes a Sequence Listing.

(56) References Cited

OTHER PUBLICATIONS

Hawkes et al., "Cytochrome P450cin (CYP176A), Isolation, Expression, and Characterization" J. Biol. Chem. 277 (31), 27725-27732 (2002).

Hawkes et al., "Cloning, Expression and Purification of Cindoxin, an Unusual Fmn-Containing Cytochrome P450 Redox Partner." ChemBioChem 1 (8), 1107-1114 (2010).

Guo et al., "Effect of Flexible Linker Length on the Activity of Fusion Protein 4-Coumaroyl-CoA Ligase::Stilbene Synthase." Mol. Biosyst. 13 (3), 598-606 (2017).

Ljungcrantz et al., "Construction of an Artificial Bifunctional Enzyme, .Beta.-Galactosidase/Galactose Dehydrogenase, Exhibiting Efficient Galactose Channeling." Biochemistry 28 (22), 8786-8792 (1989).

Hoffmann et al., "The Impact of Linker Length on P450 Fusion Constructs: Activity, Stability and Coupling." ChemCatChem 8 (8), 1591-1597 (2016).

Belsare, K. D.; Ruff, A. J.; Martinez, R.; Shivange, A. V; Mundhada, H.; Holtmann, D.; Schrader, J.; Schwaneberg, U. P-Link: A Method for Generating Multicomponent Cytochrome P450 Fusions with Variable Linker Length. Biotechniques 57 (1), 13-20 (2014).

Zhao et al., "Biosynthesis of the Sesquiterpene Antibiotic Albaflavenone in Streptomyces Coelicolor A3(2)." J. Biol. Chem. 283 (13), 8183-8189 (2008).

Liu et al., "Renewable Production of High Density Jet Fuel Precursor Sesquiterpenes from *Escherichia coli*." Biotechnol. Biofuels 11 (1), 285 (2018).

Kang et al.., "Isopentenyl Diphosphate (IPP)-Bypass Mevalonate Pathways for Isopentenol Production." Metab. Eng. 34, 25-35 (2016).

Redding-Johanson et al., "Targeted Proteomics for Metabolic Pathway Optimization: Application to Terpene Production." Metab. Eng. 13 (2), 194-203 (2011).

"Citrobacter braakii P450cin (cinA), cindoxin reductase (cinB), and cindoxin (cinC) genes, complete cds" GenBank ID: AF456128 (2012).

"*Escherichia coli* str. K-12 substr. MG1655 chromosome, complete genome" GenBank ID: CP032667 (2018).

\* cited by examiner

SEQUENCE LISTING

<160> NUMBER OF SEQ ID NOS: 22

<210> SEQ ID NO 1
<211> LENGTH: 330
<212> TYPE: PRT
<213> ORGANISM: Streptomyces clavuligerus

<400> SEQUENCE: 1

```
Met Pro Ala Gly His Glu Glu Phe Asp Ile Pro Phe Pro Ser Arg Val
 1               5                  10                  15

Asn Pro Phe His Ala Arg Ala Glu Asp Arg His Val Ala Trp Met Arg
            20                  25                  30

Ala Met Gly Leu Ile Thr Gly Asp Ala Ala Glu Ala Thr Tyr Arg Arg
        35                  40                  45

Trp Ser Pro Ala Lys Val Gly Ala Arg Trp Phe Tyr Leu Ala Gln Gly
    50                  55                  60

Glu Asp Leu Asp Leu Gly Cys Asp Ile Phe Gly Trp Phe Phe Ala Tyr
65                  70                  75                  80

Asp Asp His Phe Asp Gly Pro Thr Gly Thr Asp Pro Arg Gln Thr Ala
                85                  90                  95

Ala Phe Val Asn Arg Thr Val Ala Met Leu Asp Pro Arg Ala Asp Pro
            100                 105                 110

Thr Gly Glu His Pro Leu Asn Ile Ala Phe His Asp Leu Trp Gln Arg
        115                 120                 125

Glu Ser Ala Pro Met Ser Pro Leu Trp Gln Arg Arg Ala Val Asp His
    130                 135                 140

Trp Thr Gln Tyr Leu Thr Ala His Ile Thr Glu Ala Thr Asn Arg Thr
145                 150                 155                 160

Arg His Thr Ser Pro Thr Ile Ala Asp Tyr Leu Glu Leu Arg His Arg
                165                 170                 175

Thr Gly Phe Met Pro Pro Leu Leu Asp Leu Ile Glu Arg Val Trp Arg
            180                 185                 190

Ala Glu Ile Pro Ala Pro Val Tyr Thr Thr Pro Glu Val Gln Thr Leu
        195                 200                 205

Leu His Thr Thr Asn Gln Asn Ile Asn Ile Val Asn Asp Val Leu Ser
    210                 215                 220

Leu Glu Lys Glu Glu Ala His Gly Asp Pro His Asn Leu Val Leu Val
225                 230                 235                 240

Ile Gln His Glu Arg Gln Ser Thr Arg Gln Gln Ala Leu Ala Thr Ala
                245                 250                 255

Arg Arg Met Ile Asp Glu Trp Thr Asp Thr Phe Ile Arg Thr Glu Pro
            260                 265                 270

Arg Leu Pro Ala Leu Cys Gly Arg Leu Gly Ile Pro Leu Ala Asp Arg
        275                 280                 285

Thr Ser Leu Tyr Thr Ala Val Glu Gly Met Arg Ala Ala Ile Arg Gly
    290                 295                 300

Asn Tyr Asp Trp Cys Ala Glu Thr Asn Arg Tyr Ala Val His Arg Pro
305                 310                 315                 320

Thr Gly Thr Gly Arg Ala Thr Thr Pro Trp
                325                 330
```

<210> SEQ ID NO 2
<211> LENGTH: 361
<212> TYPE: PRT
<213> ORGANISM: Streptomyces coelicolor

<400> SEQUENCE: 2

```
Met His Ala Phe Pro His Gly Thr Thr Ala Thr Pro Thr Ala Ile Ala
1               5                   10                  15

Val Pro Pro Ser Leu Arg Leu Pro Val Ile Glu Ala Ala Phe Pro Arg
            20                  25                  30

Gln Leu His Pro Tyr Trp Pro Lys Leu Gln Glu Thr Thr Arg Thr Trp
        35                  40                  45

Leu Leu Glu Lys Arg Leu Met Pro Ala Asp Lys Val Glu Glu Tyr Ala
    50                  55                  60

Asp Gly Leu Cys Tyr Thr Asp Leu Met Ala Gly Tyr Tyr Leu Gly Ala
65                  70                  75                  80

Pro Asp Glu Val Leu Gln Ala Ile Ala Asp Tyr Ser Ala Trp Phe Phe
                85                  90                  95

Val Trp Asp Asp Arg His Asp Arg Asp Ile Val His Gly Arg Ala Gly
            100                 105                 110

Ala Trp Arg Arg Leu Arg Gly Leu Leu His Thr Ala Leu Asp Ser Pro
        115                 120                 125

Gly Asp His Leu His His Glu Asp Thr Leu Val Ala Gly Phe Ala Asp
    130                 135                 140

Ser Val Arg Arg Leu Tyr Ala Phe Leu Pro Ala Thr Trp Asn Ala Arg
145                 150                 155                 160

Phe Ala Arg His Phe His Thr Val Ile Glu Ala Tyr Asp Arg Glu Phe
                165                 170                 175

His Asn Arg Thr Arg Gly Ile Val Pro Gly Val Glu Glu Tyr Leu Glu
            180                 185                 190

Leu Arg Arg Leu Thr Phe Ala His Trp Ile Trp Thr Asp Leu Leu Glu
        195                 200                 205

Pro Ser Ser Gly Cys Glu Leu Pro Asp Ala Val Arg Lys His Pro Ala
    210                 215                 220

Tyr Arg Arg Ala Ala Leu Leu Ser Gln Glu Phe Ala Ala Trp Tyr Asn
225                 230                 235                 240

Asp Leu Cys Ser Leu Pro Lys Glu Ile Ala Gly Asp Glu Val His Asn
                245                 250                 255

Leu Gly Ile Ser Leu Ile Thr His His Ser Leu Thr Leu Glu Glu Ala
            260                 265                 270

Ile Gly Glu Val Arg Arg Val Glu Glu Cys Ile Thr Glu Phe Leu
        275                 280                 285

Ala Val Glu Arg Asp Ala Leu Arg Phe Ala Asp Glu Leu Ala Asp Gly
    290                 295                 300

Thr Val Arg Gly Lys Glu Leu Ser Gly Ala Val Arg Ala Asn Val Gly
305                 310                 315                 320

Asn Met Arg Asn Trp Phe Ser Ser Val Tyr Trp Phe His His Glu Ser
                325                 330                 335

Gly Arg Tyr Met Val Asp Ser Trp Asp Asp Arg Ser Thr Pro Pro Tyr
            340                 345                 350

Val Asn Asn Glu Ala Ala Gly Glu Lys
355                 360
```

<210> SEQ ID NO 3
<211> LENGTH: 606
<212> TYPE: PRT
<213> ORGANISM: Citrus limon

<400> SEQUENCE: 3

-continued

```
Met Ser Ser Cys Ile Asn Pro Ser Thr Leu Val Thr Ser Val Asn Ala
1               5                   10                  15

Phe Lys Cys Leu Pro Leu Ala Thr Asn Lys Ala Ala Ile Arg Ile Met
            20                  25                  30

Ala Lys Tyr Lys Pro Val Gln Cys Leu Ile Ser Ala Lys Tyr Asp Asn
                35                  40                  45

Leu Thr Val Asp Arg Arg Ser Ala Asn Tyr Gln Pro Ser Ile Trp Asp
    50                  55                  60

His Asp Phe Leu Gln Ser Leu Asn Ser Asn Tyr Thr Asp Glu Ala Tyr
65                  70                  75                  80

Lys Arg Arg Ala Glu Glu Leu Arg Gly Lys Val Lys Ile Ala Ile Lys
                85                  90                  95

Asp Val Ile Glu Pro Leu Asp Gln Leu Glu Leu Ile Asp Asn Leu Gln
                100                 105                 110

Arg Leu Gly Leu Ala His Arg Phe Glu Thr Glu Ile Arg Asn Ile Leu
            115                 120                 125

Asn Asn Ile Tyr Asn Asn Asn Lys Asp Tyr Asn Trp Arg Lys Glu Asn
    130                 135                 140

Leu Tyr Ala Thr Ser Leu Glu Phe Arg Leu Leu Arg Gln His Gly Tyr
145                 150                 155                 160

Pro Val Ser Gln Glu Val Phe Asn Gly Phe Lys Asp Asp Gln Gly Gly
                165                 170                 175

Phe Ile Cys Asp Asp Phe Lys Gly Ile Leu Ser Leu His Glu Ala Ser
            180                 185                 190

Tyr Tyr Ser Leu Glu Gly Glu Ser Ile Met Glu Glu Ala Trp Gln Phe
            195                 200                 205

Thr Ser Lys His Leu Lys Glu Val Met Ile Ser Lys Asn Met Glu Glu
    210                 215                 220

Asp Val Phe Val Ala Glu Gln Ala Lys Arg Ala Leu Glu Leu Pro Leu
225                 230                 235                 240

His Trp Lys Val Pro Met Leu Glu Ala Arg Trp Phe Ile His Ile Tyr
                245                 250                 255

Glu Arg Arg Glu Asp Lys Asn His Leu Leu Leu Glu Leu Ala Lys Met
            260                 265                 270

Glu Phe Asn Thr Leu Gln Ala Ile Tyr Gln Glu Glu Leu Lys Glu Ile
    275                 280                 285

Ser Gly Trp Trp Lys Asp Thr Gly Leu Gly Glu Lys Leu Ser Phe Ala
    290                 295                 300

Arg Asn Arg Leu Val Ala Ser Phe Leu Trp Ser Met Gly Ile Ala Phe
305                 310                 315                 320

Glu Pro Gln Phe Ala Tyr Cys Arg Arg Val Leu Thr Ile Ser Ile Ala
                325                 330                 335

Leu Ile Thr Val Ile Asp Asp Ile Tyr Asp Val Tyr Gly Thr Leu Asp
            340                 345                 350

Glu Leu Glu Ile Phe Thr Asp Ala Val Glu Arg Trp Asp Ile Asn Tyr
        355                 360                 365

Ala Leu Lys His Leu Pro Gly Tyr Met Lys Met Cys Phe Leu Ala Leu
    370                 375                 380

Tyr Asn Phe Val Asn Glu Phe Ala Tyr Tyr Val Leu Lys Gln Gln Asp
385                 390                 395                 400

Phe Asp Leu Leu Leu Ser Ile Lys Asn Ala Trp Leu Gly Leu Ile Gln
                405                 410                 415

Ala Tyr Leu Val Glu Ala Lys Trp Tyr His Ser Lys Tyr Thr Pro Lys
```

```
                420             425             430
Leu Glu Glu Tyr Leu Glu Asn Gly Leu Val Ser Ile Thr Gly Pro Leu
            435                 440                 445

Ile Ile Thr Ile Ser Tyr Leu Ser Gly Thr Asn Pro Ile Ile Lys Lys
        450                 455                 460

Glu Leu Glu Phe Leu Glu Ser Asn Pro Asp Ile Val His Trp Ser Ser
465                 470                 475                 480

Lys Ile Phe Arg Leu Gln Asp Asp Leu Gly Thr Ser Ser Asp Glu Ile
            485                 490                 495

Gln Arg Gly Asp Val Pro Lys Ser Ile Gln Cys Tyr Met His Glu Thr
                500                 505                 510

Gly Ala Ser Glu Glu Val Ala Arg Gln His Ile Lys Asp Met Met Arg
            515                 520                 525

Gln Met Trp Lys Lys Val Asn Ala Tyr Thr Ala Asp Lys Asp Ser Pro
        530                 535                 540

Leu Thr Gly Thr Thr Thr Glu Phe Leu Leu Asn Leu Val Arg Met Ser
545                 550                 555                 560

His Phe Met Tyr Leu His Gly Asp Gly His Gly Val Gln Asn Gln Glu
                565                 570                 575

Thr Ile Asp Val Gly Phe Thr Leu Leu Phe Gln Pro Ile Pro Leu Glu
            580                 585                 590

Asp Lys His Met Ala Phe Thr Ala Ser Pro Gly Thr Lys Gly
        595                 600                 605

<210> SEQ ID NO 4
<211> LENGTH: 622
<212> TYPE: PRT
<213> ORGANISM: Cannabis sativa

<400> SEQUENCE: 4

Met Gln Cys Ile Ala Phe His Gln Phe Ala Ser Ser Ser Ser Leu Pro
1               5                   10                  15

Ile Trp Ser Ser Ile Asp Asn Arg Phe Thr Pro Lys Thr Ser Ile Thr
            20                  25                  30

Ser Ile Ser Lys Pro Lys Pro Lys Leu Lys Ser Lys Ser Asn Leu Lys
        35                  40                  45

Ser Arg Ser Arg Ser Ser Thr Cys Tyr Ser Ile Gln Cys Thr Val Val
    50                  55                  60

Asp Asn Pro Ser Ser Thr Ile Thr Asn Asn Ser Asp Arg Arg Ser Ala
65                  70                  75                  80

Asn Tyr Gly Pro Pro Ile Trp Ser Phe Asp Phe Val Gln Ser Leu Pro
                85                  90                  95

Ile Gln Tyr Lys Gly Glu Ser Tyr Thr Ser Arg Leu Asn Lys Leu Glu
            100                 105                 110

Lys Asp Val Lys Arg Met Leu Ile Gly Val Glu Asn Ser Leu Ala Gln
        115                 120                 125

Leu Glu Leu Ile Asp Thr Ile Gln Arg Leu Gly Ile Ser Tyr Arg Phe
    130                 135                 140

Glu Asn Glu Ile Ile Ser Ile Leu Lys Glu Lys Phe Thr Asn Asn Asn
145                 150                 155                 160

Asp Asn Pro Asn Pro Asn Tyr Asp Leu Tyr Ala Thr Ala Leu Gln Phe
                165                 170                 175

Arg Leu Leu Arg Gln Tyr Gly Phe Glu Val Pro Gln Glu Ile Phe Asn
            180                 185                 190
```

-continued

Asn Phe Lys Asn His Lys Thr Gly Glu Phe Lys Ala Asn Ile Ser Asn
            195                 200                 205

Asp Ile Met Gly Ala Leu Gly Leu Tyr Glu Ala Ser Phe His Gly Lys
        210                 215                 220

Lys Gly Glu Ser Ile Leu Glu Glu Ala Arg Ile Phe Thr Thr Lys Cys
225                 230                 235                 240

Leu Lys Lys Tyr Lys Leu Met Ser Ser Ser Asn Asn Asn Asn Met Thr
                245                 250                 255

Leu Ile Ser Leu Leu Val Asn His Ala Leu Glu Met Pro Leu Gln Trp
            260                 265                 270

Arg Ile Thr Arg Ser Glu Ala Lys Trp Phe Ile Glu Glu Ile Tyr Glu
        275                 280                 285

Arg Lys Gln Asp Met Asn Pro Thr Leu Leu Glu Phe Ala Lys Leu Asp
290                 295                 300

Phe Asn Met Leu Gln Ser Thr Tyr Gln Glu Glu Leu Lys Val Leu Ser
305                 310                 315                 320

Arg Trp Trp Lys Asp Ser Lys Leu Gly Glu Lys Leu Pro Phe Val Arg
                325                 330                 335

Asp Arg Leu Val Glu Cys Phe Leu Trp Gln Val Gly Val Arg Phe Glu
            340                 345                 350

Pro Gln Phe Ser Tyr Phe Arg Ile Met Asp Thr Lys Leu Tyr Val Leu
        355                 360                 365

Leu Thr Ile Ile Asp Asp Met His Asp Ile Tyr Gly Thr Leu Glu Glu
        370                 375                 380

Leu Gln Leu Phe Thr Asn Ala Leu Gln Arg Trp Asp Leu Lys Glu Leu
385                 390                 395                 400

Asp Lys Leu Pro Asp Tyr Met Lys Thr Ala Phe Tyr Phe Thr Tyr Asn
                405                 410                 415

Phe Thr Asn Glu Leu Ala Phe Asp Val Leu Gln Glu His Gly Phe Val
            420                 425                 430

His Ile Glu Tyr Phe Lys Lys Leu Met Val Glu Leu Cys Lys His His
        435                 440                 445

Leu Gln Glu Ala Lys Trp Phe Tyr Ser Gly Tyr Lys Pro Thr Leu Gln
    450                 455                 460

Glu Tyr Val Glu Asn Gly Trp Leu Ser Val Gly Gly Gln Val Ile Leu
465                 470                 475                 480

Met His Ala Tyr Phe Ala Phe Thr Asn Pro Val Thr Lys Glu Ala Leu
                485                 490                 495

Glu Cys Leu Lys Asp Gly His Pro Asn Ile Val Arg His Ala Ser Ile
            500                 505                 510

Ile Leu Arg Leu Ala Asp Asp Leu Gly Thr Leu Ser Asp Glu Leu Lys
        515                 520                 525

Arg Gly Asp Val Pro Lys Ser Ile Gln Cys Tyr Met His Asp Thr Gly
530                 535                 540

Ala Ser Glu Asp Glu Ala Arg Glu His Ile Lys Tyr Leu Ile Ser Glu
545                 550                 555                 560

Ser Trp Lys Glu Met Asn Asn Glu Asp Gly Asn Ile Asn Ser Phe Phe
                565                 570                 575

Ser Asn Glu Phe Val Gln Val Cys Gln Asn Leu Gly Arg Ala Ser Gln
            580                 585                 590

Phe Ile Tyr Gln Tyr Gly Asp Gly His Ala Ser Gln Asn Asn Leu Ser
        595                 600                 605

Lys Glu Arg Val Leu Gly Leu Ile Ile Thr Pro Ile Pro Met

<210> SEQ ID NO 5
<211> LENGTH: 556
<212> TYPE: PRT
<213> ORGANISM: Vitis vinifera

<400> SEQUENCE: 5

```
Met Ser Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Leu Ser Asn Leu
            245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Arg Ile Leu Thr Lys Val Ile Ala
    290                 295                 300

Met Thr Ser Ile Leu Asp Asp Ile His Asp Ala Tyr Gly Thr Pro Glu
305                 310                 315                 320

Glu Leu Lys Leu Phe Ile Glu Ala Ile Glu Arg Trp Asp Ile Asn Ser
                325                 330                 335

Ile Asn Gln Leu Pro Glu Tyr Met Lys Leu Cys Tyr Val Ala Leu Leu
            340                 345                 350

Asp Val Tyr Lys Glu Ile Glu Glu Met Glu Lys Glu Gly Asn Gln
        355                 360                 365
```

```
Tyr Arg Val His Tyr Ala Lys Glu Val Met Lys Asn Gln Val Arg Ala
    370                 375                 380

Tyr Phe Ala Glu Ala Lys Trp Leu His Glu Glu His Val Pro Ala Phe
385                 390                 395                 400

Glu Glu Tyr Met Arg Val Ala Leu Ala Ser Ser Gly Tyr Cys Leu Leu
                405                 410                 415

Ala Thr Thr Ser Phe Val Gly Met Gly Glu Ile Ala Thr Lys Glu Ala
            420                 425                 430

Phe Asp Trp Val Thr Ser Asp Pro Lys Ile Met Ser Ser Asn Phe
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Gly
465                 470                 475                 480

Val Ser Glu Glu Gln Val Tyr Ser Glu Phe Gln Lys Gln Ile Glu Asn
                485                 490                 495

Ala Trp Leu Asp Ile Asn Gln Gly Cys Leu Lys Pro Thr Ala Val Ser
            500                 505                 510

Met Pro Leu Leu Ala Arg Leu Leu Asn Phe Thr Arg Thr Met Asp Val
        515                 520                 525

Ile Tyr Lys Glu Gln Asp Ser Tyr Thr His Val Gly Lys Val Met Arg
    530                 535                 540

Asp Asn Ile Ala Ser Val Phe Ile Asn Ala Val Ile
545                 550                 555

<210> SEQ ID NO 6
<211> LENGTH: 590
<212> TYPE: PRT
<213> ORGANISM: Vitis vinifera

<400> SEQUENCE: 6

Met Ala Leu Ser Met Leu Ser Ser Ile Pro Asn Leu Ile Thr His Thr
1               5                   10                  15

Arg Leu Pro Ile Ile Ile Lys Ser Ser Cys Lys Ala Ser Pro Arg
            20                  25                  30

Gly Ile Lys Val Lys Ile Gly Asn Ser Asn Cys Glu Glu Ile Ile Val
            35                  40                  45

Arg Arg Thr Ala Asn Tyr His Pro Thr Ile Trp Asp Tyr Asp Tyr Val
    50                  55                  60

Gln Ser Leu Arg Ser Asp Tyr Val Gly Glu Thr Tyr Thr Arg Arg Leu
65                  70                  75                  80

Asp Lys Leu Lys Arg Asp Val Lys Pro Met Leu Gly Lys Val Lys Lys
                85                  90                  95

Pro Leu Asp Gln Leu Glu Leu Ile Asp Val Leu Gln Arg Leu Gly Ile
            100                 105                 110

Tyr Tyr His Phe Lys Asp Glu Ile Lys Arg Ile Leu Asn Gly Ile Tyr
        115                 120                 125

Asn Gln Tyr Asn Arg His Glu Glu Trp Gln Lys Asp Asp Leu Tyr Ala
    130                 135                 140

Thr Ala Leu Glu Phe Arg Leu Leu Arg Gln His Gly Tyr Asp Val Pro
145                 150                 155                 160

Gln Asp Val Phe Ser Arg Phe Lys Asp Asp Thr Gly Ser Phe Lys Ala
                165                 170                 175

Cys Leu Cys Glu Asp Met Lys Gly Met Leu Cys Leu Tyr Glu Ala Ser
            180                 185                 190
```

-continued

Tyr Leu Cys Val Gln Gly Glu Ser Thr Met Glu Gln Ala Arg Asp Phe
                195                 200                 205

Ala His Arg His Leu Gly Lys Gly Leu Glu Gln Asn Ile Asp Gln Asn
    210                 215                 220

Leu Ala Ile Glu Val Lys His Ala Leu Glu Leu Pro Leu His Trp Arg
225                 230                 235                 240

Met Pro Arg Leu Glu Ala Arg Trp Phe Ile Asp Val Tyr Lys Arg
                245                 250                 255

Gln Asp Met Asn Pro Ile Leu Leu Glu Phe Ala Lys Leu Asp Phe Asn
                260                 265                 270

Met Val Gln Ala Thr His Gln Glu Asp Leu Arg His Met Ser Ser Trp
                275                 280                 285

Trp Ser Ser Thr Arg Leu Gly Glu Lys Leu Asn Phe Ala Arg Asp Arg
    290                 295                 300

Leu Met Glu Asn Phe Leu Trp Thr Val Gly Val Ile Phe Glu Pro Gln
305                 310                 315                 320

Tyr Gly Tyr Cys Arg Arg Met Ser Thr Lys Val Asn Thr Leu Ile Thr
                325                 330                 335

Ile Ile Asp Asp Val Tyr Asp Val Tyr Gly Thr Met Asp Glu Leu Glu
                340                 345                 350

Leu Phe Thr Asp Val Val Asp Arg Trp Asp Ile Asn Ala Met Asp Pro
    355                 360                 365

Leu Pro Glu Tyr Met Lys Leu Cys Phe Leu Ala Leu Tyr Asn Ser Thr
    370                 375                 380

Asn Glu Met Ala Tyr Asp Ala Leu Lys Glu His Gly Leu His Ile Val
385                 390                 395                 400

Ser Tyr Leu Arg Lys Ala Trp Ser Asp Leu Cys Lys Ser Tyr Leu Leu
                405                 410                 415

Glu Ala Lys Trp Tyr Tyr Ser Arg Tyr Thr Pro Ser Leu Gln Glu Tyr
                420                 425                 430

Ile Ser Asn Ser Trp Ile Ser Ile Ser Gly Pro Val Ile Leu Val His
    435                 440                 445

Ala Tyr Phe Leu Val Ala Asn Pro Ile Thr Lys Glu Ala Leu Gln Ser
    450                 455                 460

Leu Glu Arg Tyr His Asn Ile Ile Arg Trp Ser Ser Met Ile Leu Arg
465                 470                 475                 480

Leu Ser Asp Asp Leu Gly Thr Ser Leu Asp Glu Leu Lys Arg Gly Asp
                485                 490                 495

Val Pro Lys Ser Ile Gln Cys Tyr Met Tyr Glu Thr Gly Ala Ser Glu
                500                 505                 510

Glu Asp Ala Arg Lys His Thr Ser Tyr Leu Ile Gly Glu Thr Trp Lys
                515                 520                 525

Lys Leu Asn Glu Asp Gly Ala Val Glu Ser Pro Phe Pro Glu Thr Phe
530                 535                 540

Ile Gly Ile Ala Met Asn Leu Ala Arg Met Ala Gln Cys Met Tyr Gln
545                 550                 555                 560

His Gly Asp Gly His Gly Ile Glu Tyr Gly Glu Thr Glu Asp Arg Val
                565                 570                 575

Leu Ser Leu Leu Val Glu Pro Ile Pro Ser Leu Ser Ser Glu
                580                 585                 590

<210> SEQ ID NO 7
<211> LENGTH: 628

<212> TYPE: PRT
<213> ORGANISM: Pinus taeda

<400> SEQUENCE: 7

```
Met Ala Leu Val Ser Ala Val Pro Leu Asn Ser Lys Leu Cys Leu Arg
1               5                   10                  15

Arg Thr Leu Phe Gly Phe Ser His Glu Leu Lys Ala Ile His Ser Thr
            20                  25                  30

Val Pro Asn Leu Gly Met Cys Arg Gly Gly Lys Ser Ile Ala Pro Ser
        35                  40                  45

Met Ser Met Ser Ser Thr Thr Ser Val Ser Asn Glu Asp Gly Val Pro
    50                  55                  60

Arg Arg Ile Ala Gly His His Ser Asn Leu Trp Asp Asp Ser Ile
65                  70                  75                  80

Ala Ser Leu Ser Thr Ser Tyr Glu Ala Pro Ser Tyr Arg Lys Arg Ala
                85                  90                  95

Asp Lys Leu Ile Gly Glu Val Lys Asn Ile Phe Asp Leu Met Ser Val
            100                 105                 110

Glu Asp Gly Val Phe Thr Ser Pro Leu Ser Asp Leu His His Arg Leu
        115                 120                 125

Trp Met Val Asp Ser Val Glu Arg Leu Gly Ile Asp Arg His Phe Lys
    130                 135                 140

Asp Glu Ile Asn Ser Ala Leu Asp His Val Tyr Ser Tyr Trp Thr Glu
145                 150                 155                 160

Lys Gly Ile Gly Arg Gly Arg Glu Ser Gly Val Thr Asp Leu Asn Ser
                165                 170                 175

Thr Ala Leu Gly Leu Arg Thr Leu Arg Leu His Gly Tyr Thr Val Ser
            180                 185                 190

Ser His Val Leu Asp His Phe Lys Asn Glu Lys Gly Gln Phe Thr Cys
        195                 200                 205

Ser Ala Ile Gln Thr Glu Gly Glu Ile Arg Asp Val Leu Asn Leu Phe
    210                 215                 220

Arg Ala Ser Leu Ile Ala Phe Pro Gly Glu Lys Ile Met Glu Ala Ala
225                 230                 235                 240

Glu Ile Phe Ser Thr Met Tyr Leu Lys Asp Ala Leu Gln Lys Ile Pro
                245                 250                 255

Pro Ser Gly Leu Ser Gln Glu Ile Glu Tyr Leu Leu Glu Phe Gly Trp
            260                 265                 270

His Thr Asn Leu Pro Arg Met Glu Thr Arg Met Tyr Ile Asp Val Phe
        275                 280                 285

Gly Glu Asp Thr Thr Phe Glu Thr Pro Tyr Leu Ile Arg Glu Lys Leu
    290                 295                 300

Leu Glu Leu Ala Lys Leu Glu Phe Asn Ile Phe His Ser Leu Val Lys
305                 310                 315                 320

Arg Glu Leu Gln Ser Leu Ser Arg Trp Trp Lys Asp Tyr Gly Phe Pro
                325                 330                 335

Glu Ile Thr Phe Ser Arg His Arg His Val Glu Tyr Tyr Thr Leu Ala
            340                 345                 350

Ala Cys Ile Ala Asn Asp Pro Lys His Ser Ala Phe Arg Leu Gly Phe
        355                 360                 365

Gly Lys Ile Ser His Met Ile Thr Ile Leu Asp Asp Ile Tyr Asp Thr
    370                 375                 380

Phe Gly Thr Met Glu Glu Leu Lys Leu Leu Thr Ala Ala Phe Lys Arg
385                 390                 395                 400
```

-continued

Trp Asp Pro Ser Ser Ile Glu Cys Leu Pro Asp Tyr Met Lys Gly Val
                405                 410                 415

Tyr Met Ala Val Tyr Asp Asn Ile Asn Glu Met Ala Arg Glu Ala Gln
            420                 425                 430

Lys Ile Gln Gly Trp Asp Thr Val Ser Tyr Ala Arg Lys Ser Trp Glu
        435                 440                 445

Ala Phe Ile Gly Ala Tyr Ile Gln Glu Ala Lys Trp Ile Ser Ser Gly
    450                 455                 460

Tyr Leu Pro Thr Phe Asp Glu Tyr Leu Glu Asn Gly Lys Val Ser Phe
465                 470                 475                 480

Gly Ser Arg Ile Thr Thr Leu Glu Pro Met Leu Thr Leu Gly Phe Pro
                485                 490                 495

Leu Pro Pro Arg Ile Leu Gln Glu Ile Asp Phe Pro Ser Lys Phe Asn
            500                 505                 510

Asp Leu Ile Cys Ala Ile Leu Arg Leu Lys Gly Asp Thr Gln Cys Tyr
        515                 520                 525

Lys Ala Asp Arg Ala Arg Gly Glu Ala Ser Ala Val Ser Cys Tyr
    530                 535                 540

Met Lys Asp His Pro Gly Ile Thr Glu Glu Asp Ala Val Asn Gln Val
545                 550                 555                 560

Asn Ala Met Val Asp Asn Leu Thr Lys Glu Leu Asn Trp Glu Leu Leu
                565                 570                 575

Arg Pro Asp Ser Gly Val Pro Ile Ser Tyr Lys Lys Val Ala Phe Asp
            580                 585                 590

Ile Cys Arg Val Phe His Tyr Gly Tyr Lys Tyr Arg Asp Gly Phe Ser
        595                 600                 605

Val Ala Ser Ile Glu Ile Lys Asn Leu Val Thr Arg Thr Val Val Glu
    610                 615                 620

Thr Val Pro Leu
625

<210> SEQ ID NO 8
<211> LENGTH: 629
<212> TYPE: PRT
<213> ORGANISM: Pinus taeda

<400> SEQUENCE: 8

Met Ser Pro Val Ser Val Ile Ser Leu Pro Ser Asp Leu Cys Leu Pro
1               5                   10                  15

Thr Ser Phe Ile Asp Arg Ser Gly Arg Glu Leu Ile Pro Leu His Ile
            20                  25                  30

Thr Ile Pro Asn Val Ala Met Arg Arg Gln Gly Lys Leu Met Thr Arg
        35                  40                  45

Ala Ser Met Ser Met Asn Leu Arg Thr Ala Val Ser Asp Asp Ala Val
    50                  55                  60

Ile Arg Arg Arg Gly Asp Phe His Ser Asn Leu Trp Asp Asp Leu
65                  70                  75                  80

Ile Gln Ser Leu Ser Ser Pro Tyr Gly Glu Pro Ser Tyr Arg Glu Arg
                85                  90                  95

Ala Glu Arg Leu Ile Gly Glu Val Lys Asn Ser Phe Asn Ser Met Ser
            100                 105                 110

Asn Glu Asp Gly Glu Ser Ile Thr Pro Leu Asp Asp Leu Ile Gln Arg
        115                 120                 125

Leu Trp Met Val Asp Ser Val Glu Arg Leu Gly Ile Asp Arg His Phe

```
                130                 135                 140
Lys Lys Glu Ile Lys Ser Ala Leu Asp His Val Tyr Arg Tyr Trp Ser
145                 150                 155                 160

Glu Lys Gly Ile Gly Cys Gly Arg Glu Ser Val Val Thr Asp Leu Asn
                165                 170                 175

Ser Thr Ala Leu Gly Leu Arg Thr Leu Arg Leu His Gly Tyr Asp Val
                180                 185                 190

Ser Ala Asp Val Leu Asn His Phe Lys Asn Gln Ser Gly Gln Phe Ala
                195                 200                 205

Cys Thr Leu Lys Gln Thr Glu Asp Gln Ile Arg Thr Val Leu Asn Leu
                210                 215                 220

Tyr Arg Ala Ser Leu Ile Ala Phe Pro Gly Glu Lys Val Met Asp Glu
225                 230                 235                 240

Ala Glu Ser Phe Ser Ala Lys Tyr Leu Lys Glu Ala Leu Gln Lys Ile
                245                 250                 255

Pro Val Ser Ser Phe Ser Arg Glu Ile Gly Asp Val Leu Glu Tyr Gly
                260                 265                 270

Trp His Thr Tyr Leu Pro Arg Leu Glu Ala Arg Asn Tyr Ile Asp Val
                275                 280                 285

Phe Gly Gln Asp Thr Glu Asn Ser Lys Ser Tyr Met Lys Thr Glu Lys
                290                 295                 300

Leu Leu Glu Leu Ala Lys Leu Glu Phe Asn Ile Phe His Ala Leu Gln
305                 310                 315                 320

Lys Arg Glu Leu Glu Tyr Leu Val Arg Trp Trp Lys Gly Ser Gly Ser
                325                 330                 335

Pro Gln Met Thr Phe Cys Arg His Arg His Val Glu Tyr Tyr Thr Leu
                340                 345                 350

Ala Ser Cys Ile Ala Phe Glu Pro Gln His Ser Gly Phe Arg Leu Gly
                355                 360                 365

Phe Ala Lys Ala Cys His Ile Ile Thr Val Leu Asp Asp Met Tyr Asp
                370                 375                 380

Thr Phe Gly Thr Leu Asp Glu Leu Glu Leu Phe Thr Ser Ala Ile Lys
385                 390                 395                 400

Arg Trp Asp Pro Ser Ala Thr Glu Cys Leu Pro Glu Tyr Met Lys Gly
                405                 410                 415

Val Tyr Met Ile Val Tyr Asn Thr Val Asn Glu Met Ser Gln Glu Ala
                420                 425                 430

Asp Lys Ala Gln Gly Arg Asp Thr Leu Asn Tyr Cys Arg Gln Ala Trp
                435                 440                 445

Glu Glu Tyr Ile Asp Ala Tyr Met Gln Glu Ala Lys Trp Ile Ala Ser
                450                 455                 460

Gly Glu Val Pro Thr Phe Glu Glu Tyr Tyr Glu Asn Gly Lys Val Ser
465                 470                 475                 480

Ser Gly His Arg Val Ser Ala Leu Gln Pro Ile Leu Thr Thr Asp Ile
                485                 490                 495

Pro Phe Pro Glu His Val Leu Lys Glu Val Asp Ile Pro Ser Gln Leu
                500                 505                 510

Asn Asp Leu Ala Ser Ala Ile Leu Arg Leu Arg Gly Asp Thr Arg Cys
                515                 520                 525

Tyr Gln Ala Asp Arg Ala Arg Gly Glu Glu Ala Ser Cys Ile Ser Cys
                530                 535                 540

Tyr Met Lys Asp Asn Pro Gly Thr Thr Glu Glu Asp Ala Leu Asn His
545                 550                 555                 560
```

```
Leu Asn Ala Met Ile Ser Asp Val Ile Lys Gly Leu Asn Trp Glu Leu
                565                 570                 575

Leu Lys Pro Asn Ser Ser Val Pro Ile Ser Ala Lys Lys His Ala Phe
                580                 585                 590

Asp Ile Ser Arg Ala Phe His Cys Gly Tyr Lys Tyr Arg Asp Gly Tyr
                595                 600                 605

Ser Val Ala Asn Ile Glu Thr Lys Ser Leu Val Lys Arg Thr Val Ile
            610                 615                 620

Asp Pro Val Thr Leu
625
```

<210> SEQ ID NO 9
<211> LENGTH: 582
<212> TYPE: PRT
<213> ORGANISM: Artemisia annua

<400> SEQUENCE: 9

```
Met Ala Ser Met Cys Thr Phe Ser Ser Pro Phe Leu Leu Cys Asn Ser
1               5                   10                  15

Ser Ile Ser Arg Thr Asn Ile Val Ala Cys Asn Lys Gln Thr Ser Thr
                20                  25                  30

Leu Gln Ala Gln Val Lys Asn Val Ala Thr Ile Glu Thr Thr Asn Arg
            35                  40                  45

Arg Ser Ala Asn Tyr Ala Pro Ser Leu Trp Ser Tyr Asp Phe Val Gln
50                  55                  60

Ser Leu Ser Ser Lys Tyr Lys Gly Asp Asn Tyr Met Ala Arg Ser Arg
65                  70                  75                  80

Ala Leu Lys Gly Val Val Arg Thr Met Ile Leu Glu Ala Asn Gly Ile
                85                  90                  95

Glu Asn Pro Leu Ser Leu Leu Asn Leu Val Asp Asp Leu Gln Arg Leu
            100                 105                 110

Gly Ile Ser Tyr His Phe Leu Asp Glu Ile Ser Asn Val Leu Glu Lys
        115                 120                 125

Ile Tyr Leu Asn Phe Tyr Lys Ser Pro Glu Lys Trp Thr Asn Met Asp
130                 135                 140

Leu Asn Leu Arg Ser Leu Gly Phe Arg Leu Leu Arg Gln His Gly Tyr
145                 150                 155                 160

His Ile Pro Gln Glu Ile Phe Lys Asp Phe Ile Asp Val Asn Gly Asn
                165                 170                 175

Phe Lys Gly Asp Ile Ile Ser Met Leu Asn Leu Tyr Glu Ala Ser Tyr
            180                 185                 190

His Ser Val Glu Glu Glu Ser Ile Leu Asp Asp Ala Arg Glu Phe Thr
        195                 200                 205

Thr Lys Tyr Leu Lys Glu Thr Leu Glu Asn Ile Glu Asp Gln Asn Ile
210                 215                 220

Ala Leu Phe Ile Ser His Ala Leu Val Phe Pro Leu His Trp Met Val
225                 230                 235                 240

Pro Arg Val Glu Thr Ser Trp Phe Ile Glu Val Tyr Pro Lys Lys Val
                245                 250                 255

Gly Met Asn Pro Thr Val Leu Glu Phe Ala Lys Leu Asp Phe Asn Ile
            260                 265                 270

Leu Gln Ala Val His Gln Glu Asp Met Lys Lys Ala Ser Arg Trp Trp
        275                 280                 285

Lys Glu Thr Cys Trp Glu Lys Phe Gly Phe Ala Arg Asp Arg Leu Val
```

```
                290                 295                 300
Glu Asn Phe Met Trp Thr Val Ala Glu Asn Tyr Leu Pro His Phe Gln
305                 310                 315                 320

Thr Gly Arg Gly Val Leu Thr Lys Val Asn Ala Met Ile Thr Thr Ile
                325                 330                 335

Asp Asp Val Tyr Asp Val Tyr Gly Thr Leu Pro Glu Leu Glu Leu Phe
            340                 345                 350

Thr Asn Ile Val Asn Ser Trp Asp Ile Asn Ala Ile Asp Glu Leu Pro
        355                 360                 365

Asp Tyr Leu Lys Ile Cys Phe Leu Ala Cys Tyr Asn Ala Thr Asn Glu
    370                 375                 380

Leu Ser Tyr Asn Thr Leu Thr Asn Lys Gly Phe Phe Val His Pro Tyr
385                 390                 395                 400

Leu Lys Lys Ala Trp Gln Asp Leu Cys Asn Ser Tyr Ile Ile Glu Ala
                405                 410                 415

Lys Trp Phe Asn Asp Gly Tyr Thr Pro Thr Phe Asn Glu Phe Ile Glu
            420                 425                 430

Asn Ala Tyr Met Ser Ile Gly Ile Ala Pro Ile Ile Arg His Ala Tyr
        435                 440                 445

Leu Leu Thr Leu Thr Ser Val Thr Glu Glu Ala Leu Gln His Ile Glu
    450                 455                 460

Arg Ala Glu Ser Met Ile Arg Asn Ala Cys Leu Ile Val Arg Leu Thr
465                 470                 475                 480

Asn Asp Met Gly Thr Ser Ser Asp Glu Leu Glu Arg Gly Asp Ile Pro
                485                 490                 495

Lys Ser Ile Gln Cys Tyr Met His Glu Ser Gly Ala Thr Glu Met Glu
            500                 505                 510

Ala Arg Ala Tyr Ile Lys Gln Phe Ile Val Glu Thr Trp Lys Lys Leu
        515                 520                 525

Asn Lys Glu Arg Gln Glu Ile Gly Ser Glu Phe Pro Gln Glu Phe Val
    530                 535                 540

Asp Cys Val Ile Asn Leu Pro Arg Met Gly His Phe Met Tyr Thr Asp
545                 550                 555                 560

Gly Asp Lys His Gly Lys Pro Asp Met Phe Lys Pro Tyr Val Phe Ser
                565                 570                 575

Leu Phe Val Asn Pro Ile
            580

<210> SEQ ID NO 10
<211> LENGTH: 556
<212> TYPE: PRT
<213> ORGANISM: Solanum tuberosum

<400> SEQUENCE: 10

Met Thr Pro Ala Ala Val Val Met Ser Asn Tyr Gly Glu Glu Ile
1               5                   10                  15

Val Arg Pro Ile Ala Asp Phe Ser Pro Ser Leu Trp Gly Asp Arg Phe
                20                  25                  30

His Ser Phe Ser Leu Asp Asn Gln Ile Ala Gly Lys Tyr Ala Gln Glu
            35                  40                  45

Ile Glu Thr Leu Lys Glu Gln Ser Arg Ile Ile Leu Ser Ala Ser Ser
        50                  55                  60

Arg Arg Thr Leu Ala Glu Lys Leu Asp Leu Ile Asp Ile Val Glu Arg
65                  70                  75                  80
```

```
Leu Gly Ile Ala Tyr His Phe Glu Lys Gln Ile Asp Asp Met Leu Asp
                85                  90                  95

Gln Phe Tyr Lys Ala Asp Pro Asn Phe Glu Ala His Glu Tyr Asn Asp
            100                 105                 110

Leu Gln Thr Leu Ser Val Gln Phe Arg Leu Leu Arg Gln His Gly Tyr
        115                 120                 125

Asn Ile Ser Pro Lys Leu Phe Ile Arg Phe Gln Asp Ala Lys Gly Lys
    130                 135                 140

Phe Lys Glu Ser Leu Cys Asn Asp Ile Lys Gly Leu Leu Asn Leu Tyr
145                 150                 155                 160

Glu Ala Ser His Val Arg Thr His Gly Glu Asp Ile Leu Glu Ala
                165                 170                 175

Leu Ala Phe Ser Thr Ala His Leu Glu Ser Ala Ala Pro His Leu Lys
            180                 185                 190

Ser Pro Leu Ser Lys Gln Val Thr His Ala Leu Glu Gln Ser Leu His
        195                 200                 205

Lys Ser Ile Pro Arg Val Glu Thr Arg Tyr Phe Ile Ser Ile Tyr Glu
    210                 215                 220

Glu Glu Glu Gln Lys Asn Asp Val Leu Leu Gln Phe Ala Lys Leu Asp
225                 230                 235                 240

Phe Asn Leu Leu Gln Met Leu His Lys Gln Glu Leu Ser Glu Val Ser
                245                 250                 255

Arg Trp Trp Lys Asp Leu Asp Phe Val Thr Thr Leu Pro Tyr Ala Arg
            260                 265                 270

Asp Arg Ala Val Glu Cys Tyr Phe Trp Thr Met Gly Val Tyr Ala Glu
        275                 280                 285

Pro Gln Tyr Ser Gln Ala Arg Val Met Leu Ala Lys Thr Ile Ala Met
    290                 295                 300

Ile Ser Ile Val Asp Asp Thr Phe Asp Ala Tyr Gly Ile Val Lys Glu
305                 310                 315                 320

Leu Glu Ile Tyr Thr Asp Ala Ile Gln Arg Trp Asp Ile Ser Gln Ile
                325                 330                 335

Asp Arg Leu Pro Asp Tyr Met Lys Ile Ser Tyr Lys Ala Leu Leu Asp
            340                 345                 350

Leu Tyr Asn Asp Tyr Glu Met Glu Leu Ser Lys Asp Gly Arg Ser Asp
        355                 360                 365

Val Val His Tyr Ala Lys Glu Arg Met Lys Glu Ile Val Arg Asn Tyr
    370                 375                 380

Phe Val Glu Ala Lys Trp Phe Ile Glu Gly Tyr Met Pro Pro Val Ser
385                 390                 395                 400

Glu Tyr Leu Ser Asn Ala Leu Ala Thr Ser Thr Tyr Tyr Leu Leu Thr
                405                 410                 415

Thr Thr Ser Tyr Leu Gly Met Lys Ser Ala Asn Lys Gln Asp Phe Glu
            420                 425                 430

Trp Leu Ala Lys Asn Pro Lys Ile Leu Glu Ala Asn Val Thr Leu Cys
        435                 440                 445

Arg Val Ile Asp Asp Ile Ala Thr Tyr Glu Val Glu Lys Gly Arg Gly
    450                 455                 460

Gln Ile Ala Thr Gly Ile Glu Cys Tyr Met Arg Asp Tyr Gly Val Ser
465                 470                 475                 480

Thr Glu Lys Ala Met Glu Lys Phe Gln Glu Met Ala Glu Thr Ala Trp
                485                 490                 495

Lys Asp Val Asn Glu Gly Ile Leu Arg Pro Thr Pro Val Ser Thr Glu
```

```
                     500                 505                 510
Ile Leu Thr Arg Ile Leu Asn Leu Ala Arg Ile Ile Asp Val Thr Tyr
                515                 520                 525

Lys His Asn Gln Asp Gly Tyr Thr His Pro Glu Lys Val Leu Lys Pro
            530                 535                 540

His Ile Ala Leu Leu Val Asp Ser Ile Glu Ile
545                 550                 555

<210> SEQ ID NO 11
<211> LENGTH: 546
<212> TYPE: PRT
<213> ORGANISM: Artemisia annua

<400> SEQUENCE: 11

Met Ser Leu Thr Glu Glu Lys Pro Ile Arg Pro Ile Ala Asn Phe Pro
1               5                   10                  15

Pro Ser Ile Trp Gly Asp Gln Phe Leu Ile Tyr Glu Lys Gln Val Glu
                20                  25                  30

Gln Gly Val Glu Gln Ile Val Asn Asp Leu Lys Lys Glu Val Arg Gln
            35                  40                  45

Leu Leu Lys Glu Ala Leu Asp Ile Pro Met Lys His Ala Asn Leu Leu
        50                  55                  60

Lys Leu Ile Asp Glu Ile Gln Arg Leu Gly Ile Pro Tyr His Phe Glu
65                  70                  75                  80

Arg Glu Ile Asp His Ala Leu Gln Cys Ile Tyr Glu Thr Tyr Gly Asp
                85                  90                  95

Asn Trp Asn Gly Asp Arg Ser Ser Leu Trp Phe Arg Leu Met Arg Lys
            100                 105                 110

Gln Gly Tyr Tyr Val Thr Cys Asp Val Phe Asn Asn Tyr Lys Asp Lys
        115                 120                 125

Asn Gly Ala Phe Lys Gln Ser Leu Ala Asn Asp Val Glu Gly Leu Leu
130                 135                 140

Glu Leu Tyr Glu Ala Thr Ser Met Arg Val Pro Gly Glu Ile Ile Leu
145                 150                 155                 160

Glu Asp Ala Leu Gly Phe Thr Arg Ser Arg Leu Ser Ile Met Thr Lys
                165                 170                 175

Asp Ala Phe Ser Thr Asn Pro Ala Leu Phe Thr Glu Ile Gln Arg Ala
            180                 185                 190

Leu Lys Gln Pro Leu Trp Lys Arg Leu Pro Arg Ile Glu Ala Ala Gln
        195                 200                 205

Tyr Ile Pro Phe Tyr Gln Gln Gln Asp Ser His Asn Lys Thr Leu Leu
    210                 215                 220

Lys Leu Ala Lys Leu Glu Phe Asn Leu Leu Gln Ser Leu His Lys Glu
225                 230                 235                 240

Glu Leu Ser His Val Cys Lys Trp Trp Lys Ala Phe Asp Ile Lys Lys
                245                 250                 255

Asn Ala Pro Cys Leu Arg Asp Arg Ile Val Glu Cys Tyr Phe Trp Gly
            260                 265                 270

Leu Gly Ser Gly Tyr Glu Pro Gln Tyr Ser Arg Ala Arg Val Phe Phe
        275                 280                 285

Thr Lys Ala Val Ala Val Ile Thr Leu Ile Asp Asp Thr Tyr Asp Ala
    290                 295                 300

Tyr Gly Thr Tyr Glu Glu Leu Lys Ile Phe Thr Glu Ala Val Glu Arg
305                 310                 315                 320
```

```
Trp Ser Ile Thr Cys Leu Asp Thr Leu Pro Glu Tyr Met Lys Pro Ile
            325                 330                 335

Tyr Lys Leu Phe Met Asp Thr Tyr Thr Glu Met Glu Glu Phe Leu Ala
            340                 345                 350

Lys Glu Gly Arg Thr Asp Leu Phe Asn Cys Gly Lys Glu Phe Val Lys
            355                 360                 365

Glu Phe Val Arg Asn Leu Met Val Glu Ala Lys Trp Ala Asn Glu Gly
370                 375                 380

His Ile Pro Thr Thr Glu His Asp Pro Val Ile Ile Thr Gly
385                 390                 395                 400

Gly Ala Asn Leu Leu Thr Thr Thr Cys Tyr Leu Gly Met Ser Asp Ile
                405                 410                 415

Phe Thr Lys Glu Ser Val Glu Trp Ala Val Ser Ala Pro Pro Leu Phe
            420                 425                 430

Arg Tyr Ser Gly Ile Leu Gly Arg Arg Leu Asn Asp Leu Met Thr His
            435                 440                 445

Lys Ala Glu Gln Glu Arg Lys His Ser Ser Ser Leu Glu Ser Tyr
            450                 455                 460

Met Lys Glu Tyr Asn Val Asn Glu Gly Tyr Ala Gln Thr Leu Ile Tyr
465                 470                 475                 480

Lys Glu Val Glu Asp Val Trp Lys Asp Ile Asn Arg Glu Tyr Leu Thr
                485                 490                 495

Thr Lys Asn Ile Pro Arg Pro Leu Leu Met Ala Val Ile Tyr Leu Cys
                500                 505                 510

Gln Phe Leu Glu Val Gln Tyr Ala Gly Lys Asp Asn Phe Thr Arg Met
            515                 520                 525

Gly Asp Glu Tyr Lys His Leu Ile Lys Ser Leu Leu Val Tyr Pro Met
            530                 535                 540

Ser Ile
545

<210> SEQ ID NO 12
<211> LENGTH: 545
<212> TYPE: PRT
<213> ORGANISM: Pogostemon cablin

<400> SEQUENCE: 12

Met Ala Ala Phe Thr Ala Asn Ala Val Asp Met Arg Pro Pro Val Ile
1               5                   10                  15

Thr Ile His Pro Arg Ser Lys Asp Ile Phe Ser Gln Phe Ser Leu Asp
            20                  25                  30

Asp Lys Leu Gln Lys Gln Tyr Ala Gln Gly Ile Glu Ala Leu Lys Glu
            35                  40                  45

Glu Ala Arg Ser Met Leu Met Ala Ala Lys Ser Ala Lys Val Met Ile
        50                  55                  60

Leu Ile Asp Thr Leu Glu Arg Leu Gly Leu Gly Tyr His Phe Glu Lys
65                  70                  75                  80

Glu Ile Glu Glu Lys Leu Glu Ala Ile Tyr Lys Lys Glu Asp Gly Asp
                85                  90                  95

Asp Tyr Asp Leu Phe Thr Thr Ala Leu Arg Phe Arg Leu Leu Arg Gln
            100                 105                 110

His Gln Arg Arg Val Pro Cys Ser Val Phe Asp Lys Phe Met Asn Lys
            115                 120                 125

Glu Gly Lys Phe Glu Glu Glu Pro Leu Ile Ser Asp Val Glu Gly Leu
            130                 135                 140
```

```
Leu Ser Leu Tyr Asp Ala Ala Tyr Leu Gln Ile His Gly Glu His Ile
145                 150                 155                 160

Leu Gln Glu Ala Leu Ile Phe Thr Thr His His Leu Thr Arg Ile Glu
                165                 170                 175

Pro Gln Leu Asp Asp His Ser Pro Leu Lys Leu Lys Leu Asn Arg Ala
            180                 185                 190

Leu Glu Phe Pro Phe Tyr Arg Glu Ile Pro Ile Ile Tyr Ala His Phe
        195                 200                 205

Tyr Ile Ser Val Tyr Glu Arg Asp Asp Ser Arg Asp Glu Val Leu Leu
    210                 215                 220

Lys Met Ala Lys Leu Ser Tyr Asn Phe Leu Gln Asn Leu Tyr Lys Lys
225                 230                 235                 240

Glu Leu Ser Gln Leu Ser Arg Trp Trp Asn Lys Leu Glu Leu Ile Pro
                245                 250                 255

Asn Leu Pro Tyr Ile Arg Asp Ser Val Ala Gly Ala Tyr Leu Trp Ala
            260                 265                 270

Val Ala Leu Tyr Phe Glu Pro Gln Tyr Ser Asp Val Arg Met Ala Ile
        275                 280                 285

Ala Lys Leu Ile Gln Ile Ala Ala Val Asp Asp Thr Tyr Asp Asn
290                 295                 300

Tyr Ala Thr Ile Arg Glu Ala Gln Leu Leu Thr Glu Ala Leu Glu Arg
305                 310                 315                 320

Leu Asn Val His Glu Ile Asp Thr Leu Pro Asp Tyr Met Lys Ile Val
                325                 330                 335

Tyr Arg Phe Val Met Ser Trp Ser Glu Asp Phe Glu Arg Asp Ala Thr
            340                 345                 350

Ile Lys Glu Gln Met Leu Ala Thr Pro Tyr Phe Lys Ala Glu Met Lys
        355                 360                 365

Lys Leu Gly Arg Ala Tyr Asn Gln Glu Leu Lys Trp Val Met Glu Arg
    370                 375                 380

Gln Leu Pro Ser Phe Glu Glu Tyr Met Lys Asn Ser Glu Ile Thr Ser
385                 390                 395                 400

Gly Val Tyr Ile Met Phe Thr Val Ile Ser Pro Tyr Leu Asn Ser Ala
                405                 410                 415

Thr Gln Lys Asn Ile Asp Trp Leu Leu Ser Gln Pro Arg Leu Ala Ser
            420                 425                 430

Ser Thr Ala Ile Val Met Arg Cys Cys Asn Asp Leu Gly Ser Asn Gln
        435                 440                 445

Arg Glu Ser Lys Gly Gly Glu Val Met Thr Ser Leu Asp Cys Tyr Met
    450                 455                 460

Lys Gln His Gly Ala Ser Lys Gln Glu Thr Ile Ser Lys Phe Lys Leu
465                 470                 475                 480

Ile Ile Glu Asp Glu Trp Lys Asn Leu Asn Glu Glu Trp Ala Ala Thr
                485                 490                 495

Thr Cys Leu Pro Lys Val Met Val Glu Ile Phe Arg Asn Tyr Ala Arg
            500                 505                 510

Ile Ala Gly Phe Cys Tyr Lys Asn Asn Gly Asp Ala Tyr Thr Ser Pro
        515                 520                 525

Lys Ile Val Gln Gln Cys Phe Asp Ala Leu Phe Val Asn Pro Leu Arg
    530                 535                 540

Ile
545
```

<210> SEQ ID NO 13
<211> LENGTH: 576
<212> TYPE: PRT
<213> ORGANISM: Pogostemon cablin

<400> SEQUENCE: 13

```
Met Asp Ala Phe Ala Thr Ser Pro Thr Thr Ala Leu Phe Glu Thr Val
1               5                   10                  15

Asn Cys Asn Ala His Val Ala Pro Met Ala Gly Glu Asp Ser Ser Glu
            20                  25                  30

Asn Arg Pro Ala Ser Asn Tyr Lys Pro Ser Thr Trp Asp Tyr Glu Phe
        35                  40                  45

Leu Gln Ser Leu Ala Thr Thr Asn Asn Thr Val Gly Glu Lys His Thr
    50                  55                  60

Arg Met Ala Asp Lys Leu Lys Glu Glu Val Lys Ser Met Met Lys Gly
65                  70                  75                  80

Thr Met Glu Pro Val Ala Lys Leu Glu Leu Ile Asn Ile Val Gln Arg
                85                  90                  95

Leu Gly Leu Lys Tyr Arg Phe Glu Ser Glu Ile Lys Glu Glu Leu Phe
            100                 105                 110

Ser Leu Tyr Lys Asp Gly Thr Asp Ala Trp Trp Val Gly Asn Leu His
        115                 120                 125

Ala Thr Ala Leu Arg Phe Arg Leu Leu Arg Glu Asn Gly Ile Phe Val
    130                 135                 140

Pro Gln Asp Val Phe Glu Thr Phe Lys Asp Lys Ser Gly Glu Phe Lys
145                 150                 155                 160

Ser Gln Leu Cys Lys Asp Val Arg Gly Leu Leu Ser Leu Tyr Glu Ala
                165                 170                 175

Ser Tyr Leu Gly Trp Glu Gly Glu Leu Leu Asp Gly Ala Lys Lys
            180                 185                 190

Phe Ser Thr Thr Asn Leu Asn Asn Val Lys Glu Ser Ile Ser Ser Asn
        195                 200                 205

Thr Leu Gly Arg Leu Val Lys His Ala Leu Asn Leu Pro Leu His Trp
    210                 215                 220

Ser Ala Ala Arg Tyr Glu Ala Arg Trp Phe Ile Asp Glu Tyr Glu Arg
225                 230                 235                 240

Glu Glu Asn Val Ile Pro Asn Leu Leu Lys Tyr Ala Lys Leu Asp Phe
                245                 250                 255

Asn Val Val Gln Ser Ile His Gln Lys Glu Leu Gly Asn Leu Ala Arg
            260                 265                 270

Trp Trp Val Glu Thr Gly Leu Asp Lys Leu Gly Phe Val Arg Asn Thr
        275                 280                 285

Leu Met Gln Asn Phe Met Trp Gly Cys Ala Met Ala Phe Glu Pro Gln
    290                 295                 300

Tyr Gly Lys Val Arg Asp Ala Ala Val Lys Leu Gly Ser Leu Ile Thr
305                 310                 315                 320

Met Val Asp Asp Val Tyr Asp Val Tyr Gly Thr Leu Glu Glu Leu Glu
                325                 330                 335

Ile Phe Thr Asp Ile Val Asp Arg Trp Asp Ile Asn Gly Ile Asp Lys
            340                 345                 350

Leu Pro Arg Asn Ile Ser Met Ile Val Leu Thr Met Phe Asn Thr Ala
        355                 360                 365

Asn Gln Ile Ser Tyr Asp Leu Leu Arg Asp Arg Gly Phe Asn Ser Ile
    370                 375                 380
```

```
Pro His Ile Ala Glu Ala Trp Ala Thr Leu Cys Lys Thr Tyr Leu Lys
385                 390                 395                 400

Glu Ala Lys Trp Tyr His Ser Gly Tyr Lys Pro Thr Leu Glu Glu Tyr
                405                 410                 415

Leu Glu Asn Gly Leu Val Ser Ile Ser Phe Val Leu Ser Leu Val Thr
            420                 425                 430

Ala Tyr Leu Gln Thr Glu Arg Leu Glu Asn Leu Thr Tyr Glu Ser Ala
        435                 440                 445

Ala Tyr Val Asn Ser Val Pro Pro Leu Val Arg Tyr Ser Gly Leu Leu
    450                 455                 460

Asn Arg Leu Tyr Asn Asp Leu Gly Thr Ser Ala Glu Ile Ala Arg
465                 470                 475                 480

Gly Asp Thr Leu Lys Ser Ile Gln Cys Tyr Met Thr Gln Thr Gly Ala
                485                 490                 495

Thr Glu Glu Val Ala Arg Glu His Ile Lys Gly Leu Val His Glu Ala
            500                 505                 510

Trp Lys Gly Met Asn Arg Cys Leu Phe Glu Gln Thr Pro Leu Ala Glu
        515                 520                 525

Pro Phe Val Gly Phe Asn Val Asn Thr Val Arg Gly Ser Gln Phe Phe
    530                 535                 540

Tyr Gln His Gly Asp Gly Tyr Ala Val Thr Glu Ser Trp Thr Lys Asp
545                 550                 555                 560

Leu Ser Leu Ser Val Leu Ile His Pro Ile Pro Leu Asn Glu Glu Asp
                565                 570                 575

<210> SEQ ID NO 14
<211> LENGTH: 533
<212> TYPE: PRT
<213> ORGANISM: Zea mays

<400> SEQUENCE: 14

Met Asp Ala Thr Ala Phe His Pro Ser Leu Trp Gly Asp Phe Phe Val
1               5                   10                  15

Lys Tyr Lys Pro Pro Thr Ala Pro Lys Arg Gly His Met Thr Glu Arg
                20                  25                  30

Ala Glu Leu Leu Lys Glu Val Arg Lys Thr Leu Lys Ala Ala Ala
            35                  40                  45

Asn Gln Ile Thr Asn Ala Leu Asp Leu Ile Ile Thr Leu Gln Arg Leu
        50                  55                  60

Gly Leu Asp His His Tyr Glu Asn Glu Ile Ser Glu Leu Leu Arg Phe
65                  70                  75                  80

Val Tyr Ser Ser Ser Asp Tyr Asp Asp Lys Asp Leu Tyr Val Val Ser
                85                  90                  95

Leu Arg Phe Tyr Leu Leu Arg Lys His Gly His Cys Val Ser Ser Asp
            100                 105                 110

Val Phe Thr Ser Phe Lys Asp Glu Glu Gly Asn Phe Val Val Asp Asp
        115                 120                 125

Thr Lys Cys Leu Leu Ser Leu Tyr Asn Ala Ala Tyr Val Arg Thr His
130                 135                 140

Gly Glu Lys Val Leu Asp Glu Ala Ile Thr Phe Thr Arg Arg Gln Leu
                150                 155                 160
145

Glu Ala Ser Leu Leu Asp Pro Leu Glu Pro Ala Leu Ala Asp Glu Val
            165                 170                 175

His Leu Thr Leu Gln Thr Pro Leu Phe Arg Arg Leu Arg Ile Leu Glu
```

```
                180             185             190
Ala Ile Asn Tyr Ile Pro Ile Tyr Gly Lys Glu Ala Gly Arg Asn Glu
        195             200             205

Ala Ile Leu Glu Leu Ala Lys Leu Asn Phe Asn Leu Ala Gln Leu Ile
210             215             220

Tyr Cys Glu Glu Leu Lys Glu Val Thr Leu Trp Lys Gln Leu Asn
225             230             235             240

Val Glu Thr Asn Leu Ser Phe Ile Arg Asp Arg Ile Val Glu Cys His
        245             250             255

Phe Trp Met Thr Gly Ala Cys Cys Glu Pro Gln Tyr Ser Leu Ser Arg
        260             265             270

Val Ile Ala Thr Lys Met Thr Ala Leu Ile Thr Val Leu Asp Asp Met
        275             280             285

Met Asp Thr Tyr Ser Thr Thr Glu Glu Ala Met Leu Leu Ala Glu Ala
        290             295             300

Ile Tyr Arg Trp Glu Glu Asn Ala Ala Glu Leu Leu Pro Arg Tyr Met
305             310             315             320

Lys Asp Phe Tyr Leu Tyr Leu Leu Lys Thr Ile Asp Ser Cys Gly Asp
                325             330             335

Glu Leu Gly Pro Asn Arg Ser Phe Arg Thr Phe Tyr Leu Lys Glu Met
        340             345             350

Leu Lys Val Leu Val Arg Gly Ser Ser Gln Glu Ile Lys Trp Arg Asn
        355             360             365

Glu Asn Tyr Val Pro Lys Thr Ile Ser Glu His Leu Glu His Ser Gly
        370             375             380

Pro Thr Val Gly Ala Phe Gln Val Ala Cys Ser Ser Phe Val Gly Met
385             390             395             400

Gly Asp Ser Ile Thr Lys Glu Ser Phe Glu Trp Leu Leu Thr Tyr Pro
                405             410             415

Glu Leu Ala Lys Ser Leu Met Asn Ile Ser Arg Leu Leu Asn Asp Thr
        420             425             430

Ala Ser Thr Lys Arg Glu Gln Asn Ala Gly Gln His Val Ser Thr Val
        435             440             445

Gln Cys Tyr Met Leu Lys His Gly Thr Thr Met Asp Glu Ala Cys Glu
        450             455             460

Lys Ile Lys Glu Leu Thr Glu Asp Ser Trp Lys Asp Met Met Glu Leu
465             470             475             480

Tyr Leu Thr Pro Thr Glu His Pro Lys Leu Ile Ala Gln Thr Ile Val
                485             490             495

Asp Phe Ala Arg Thr Ala Asp Tyr Met Tyr Lys Glu Thr Asp Gly Phe
        500             505             510

Thr Phe Ser His Thr Ile Lys Asp Met Ile Ala Lys Leu Phe Val Asp
        515             520             525

Pro Ile Ser Leu Phe
        530

<210> SEQ ID NO 15
<211> LENGTH: 540
<212> TYPE: PRT
<213> ORGANISM: Ocimum basilicum

<400> SEQUENCE: 15

Met Asp Val Ser Ile Leu Arg Asp Val Arg Pro Pro Val Thr Ser Tyr
1               5               10              15
```

```
Ala Pro Asn Ile Trp Ala Asp Thr Phe Ser Asn Ile Ser Leu Asp Glu
            20                  25                  30

Glu Val Gln Lys Lys Tyr Ala Glu Thr Ile Glu Ala Leu Lys Gln Val
        35                  40                  45

Val Arg Gly Met Leu Met Ala Ala Thr Pro Ile Lys Gln Met Ile
50                  55                  60

Phe Ile Asp Thr Leu Glu Arg Leu Gly Leu Ala Tyr His Phe Glu Thr
65                  70                  75                  80

Glu Ile Glu His Lys Leu Gln Lys Ile Tyr Asp Asp Asn Val Cys Gly
                85                  90                  95

Asp Asp Cys Asp Leu Phe Thr Thr Ala Leu Arg Phe Arg Leu Leu Arg
            100                 105                 110

Gln His Arg His His Val Ser Cys Asp Val Phe Asp Lys Phe Leu Tyr
        115                 120                 125

Glu Glu Gly Lys Phe Lys Gly Asp Ala Glu Gly Leu Leu Ser Leu Tyr
        130                 135                 140

Glu Ala Ser His Val Arg Phe His Asn Glu Lys Ile Leu Glu Glu Ala
145                 150                 155                 160

Glu Arg Phe Thr Arg Gln Glu Leu Ser Cys Trp Ile Lys Leu Gln Ser
                165                 170                 175

Pro Leu Lys Asp Lys Val Lys Arg Ala Leu Glu Arg Pro Leu His Arg
            180                 185                 190

Glu Val Pro Ile Leu Tyr Ala Arg His Phe Ile Ser Ile Tyr Glu Lys
        195                 200                 205

Asp Glu Ser Met Asp Glu His Leu Leu Lys Leu Ala Lys Phe Asn Phe
        210                 215                 220

Asn Phe Leu Gln Asn Leu Tyr Lys Lys Glu Leu Tyr Asp Leu Ser Arg
225                 230                 235                 240

Trp Trp Asn Lys Phe Asp Leu Lys Thr Lys Leu Pro Tyr Ile Arg Asp
                245                 250                 255

Arg Leu Ala Glu Ala Tyr Leu Trp Gly Val Gly Tyr His Phe Glu Pro
            260                 265                 270

Gln Tyr Ser Tyr Val Arg Lys Gly Val Val Leu Ser Ile Lys Ile Ile
        275                 280                 285

Gly Ile Leu Asp Asp Thr Tyr Asp Asn Tyr Ala Thr Val Asn Glu Ala
290                 295                 300

Gln Leu Phe Thr Glu Ile Leu Asp Arg Trp Ser Met Asp Glu Ile Asp
305                 310                 315                 320

Arg Leu Pro Asp Tyr Met Lys Ile Val Leu His Phe Val Met Ser Ala
                325                 330                 335

Tyr Glu Glu Tyr Glu Arg Asp Ala Lys Ile Val Tyr Gly Lys Lys Phe
            340                 345                 350

Ala Ser Pro Tyr Phe Lys Glu Thr Ile Gln Gln Leu Ala Arg Gly Tyr
        355                 360                 365

Asn Gln Glu Leu Lys Trp Val Met Glu Lys Gln Met Pro Pro Phe Lys
        370                 375                 380

Asp Tyr Leu Lys Asn Ser Glu Ile Thr Ser Cys Ile Tyr Ile Met Phe
385                 390                 395                 400

Ala Ser Ile Ile Pro Gly Leu Lys Ser Phe Thr Gln Glu Ala Ile Asp
                405                 410                 415

Trp Ile Lys Asn Glu Pro Asn Phe Ala Val Lys Ala Gly Leu Ile Gly
            420                 425                 430

Arg Tyr Trp Asp Asp Ile Gly Ser His Lys Arg Glu Ser Lys Gly Gly
```

```
            435                 440                 445
Glu Met Leu Thr Val Met Asp Cys Tyr Met Lys Gln Tyr Ser Val Ser
450                 455                 460

Ile Gln Glu Thr Ile Ser Glu Phe Ala Lys Ala Val Glu Asp Ser Trp
465                 470                 475                 480

Lys Glu Val Asn Glu Gly Trp Val Tyr Thr Ile Ser Met Ser Lys Glu
                    485                 490                 495

Ile Thr Val Gln Phe Leu Asn Tyr Ser Arg Met Cys Asp Ala Ser Tyr
                500                 505                 510

Asn Arg Asn Asn Gly Asp Gly Tyr Thr Asp Pro Ser Phe Ala Lys Ser
            515                 520                 525

Asn Ile Thr Ala Leu Phe Val Asp Pro Ile Ile Ile
530                 535                 540

<210> SEQ ID NO 16
<211> LENGTH: 342
<212> TYPE: PRT
<213> ORGANISM: Penicillium roqueforti

<400> SEQUENCE: 16

Met Ala Thr Ser Thr Glu Thr Ile Ser Ser Leu Ala Gln Pro Phe Val
1               5                   10                  15

His Leu Glu Asn Pro Ile Asn Ser Pro Leu Val Lys Glu Thr Ile Arg
            20                  25                  30

Pro Arg Asn Asp Thr Thr Ile Thr Pro Pro Thr Gln Trp Ser Tyr
        35                  40                  45

Leu Cys His Pro Arg Val Lys Glu Val Gln Asp Glu Val Asp Gly Tyr
50                  55                  60

Phe Leu Glu Asn Trp Lys Phe Pro Ser Phe Lys Ala Val Arg Thr Phe
65                  70                  75                  80

Leu Asp Ala Lys Phe Ser Glu Val Thr Cys Leu Tyr Phe Pro Leu Ala
                85                  90                  95

Leu Asp Asp Arg Ile His Phe Ala Cys Arg Leu Leu Thr Val Leu Phe
            100                 105                 110

Leu Ile Asp Asp Val Leu Glu His Met Ser Phe Ala Asp Gly Glu Ala
        115                 120                 125

Tyr Asn Asn Arg Leu Ile Pro Ile Ser Arg Gly Asp Val Leu Pro Asp
130                 135                 140

Arg Thr Lys Pro Glu Glu Phe Ile Leu Tyr Asp Leu Trp Glu Ser Met
145                 150                 155                 160

Arg Ala His Asp Ala Glu Leu Ala Asn Glu Val Leu Glu Pro Thr Phe
                165                 170                 175

Val Phe Met Arg Ala Gln Thr Asp Arg Ala Arg Leu Ser Ile His Glu
            180                 185                 190

Leu Gly His Tyr Leu Glu Tyr Arg Glu Lys Asp Val Gly Lys Ala Leu
        195                 200                 205

Leu Ser Ala Leu Met Arg Phe Ser Met Gly Leu Arg Leu Ser Ala Asp
210                 215                 220

Glu Leu Gln Asp Met Lys Ala Leu Glu Ala Asn Cys Ala Lys Gln Leu
225                 230                 235                 240

Ser Val Val Asn Asp Ile Tyr Ser Tyr Asp Lys Glu Glu Ala Ser
                245                 250                 255

Arg Thr Gly His Lys Glu Gly Ala Phe Leu Cys Ser Ala Val Lys Val
            260                 265                 270
```

```
Leu Ala Glu Glu Ser Lys Leu Gly Ile Pro Ala Thr Lys Arg Val Leu
                275                 280                 285

Trp Ser Met Thr Arg Glu Trp Glu Thr Val His Asp Glu Ile Val Ala
            290                 295                 300

Glu Lys Ile Ala Ser Pro Asp Gly Cys Ser Glu Ala Ala Lys Ala Tyr
305                 310                 315                 320

Met Lys Gly Leu Glu Tyr Gln Met Ser Gly Asn Glu Gln Trp Ser Lys
                325                 330                 335

Thr Thr Arg Arg Tyr Asn
            340

<210> SEQ ID NO 17
<211> LENGTH: 5
<212> TYPE: PRT
<213> ORGANISM: Streptomyces clavuligerus
<220> FEATURE:
<221> NAME/KEY: misc_feature
<222> LOCATION: (3)..(4)
<223> OTHER INFORMATION: Xaa can be any naturally occurring amino acid

<400> SEQUENCE: 17

Asp Asp Xaa Xaa Asp
1               5

<210> SEQ ID NO 18
<211> LENGTH: 5
<212> TYPE: PRT
<213> ORGANISM: Streptomyces clavuligerus
<220> FEATURE:
<221> NAME/KEY: misc_feature
<222> LOCATION: (3)..(4)
<223> OTHER INFORMATION: Xaa can be any naturally occurring amino acid

<400> SEQUENCE: 18

Asp Asp Xaa Xaa Glu
1               5

<210> SEQ ID NO 19
<211> LENGTH: 404
<212> TYPE: PRT
<213> ORGANISM: Citrobacter braakii

<400> SEQUENCE: 19

Met Thr Ala Thr Val Ala Ser Thr Ser Leu Phe Thr Thr Ala Asp His
1               5                   10                  15

Tyr His Thr Pro Leu Gly Pro Asp Gly Thr Pro His Ala Phe Phe Glu
                20                  25                  30

Ala Leu Arg Asp Glu Ala Glu Thr Thr Pro Ile Gly Trp Ser Glu Ala
            35                  40                  45

Tyr Gly Gly His Trp Val Val Ala Gly Tyr Lys Glu Ile Gln Ala Val
        50                  55                  60

Ile Gln Asn Thr Lys Ala Phe Ser Asn Lys Gly Val Thr Phe Pro Arg
65                  70                  75                  80

Tyr Glu Thr Gly Glu Phe Glu Leu Met Met Ala Gly Gln Asp Asp Pro
                85                  90                  95

Val His Lys Lys Tyr Arg Gln Leu Val Ala Lys Pro Phe Ser Pro Glu
                100                 105                 110

Ala Thr Asp Leu Phe Thr Glu Gln Leu Arg Gln Ser Thr Asn Asp Leu
            115                 120                 125

Ile Asp Ala Arg Ile Glu Leu Gly Glu Gly Asp Ala Ala Thr Trp Leu
        130                 135                 140
```

```
Ala Asn Glu Ile Pro Ala Arg Leu Thr Ala Ile Leu Leu Gly Leu Pro
145                 150                 155                 160

Pro Glu Asp Gly Asp Thr Tyr Arg Arg Trp Val Trp Ala Ile Thr His
            165                 170                 175

Val Glu Asn Pro Glu Glu Gly Ala Glu Ile Phe Ala Glu Leu Val Ala
            180                 185                 190

His Ala Arg Thr Leu Ile Ala Glu Arg Arg Thr Asn Pro Gly Asn Asp
            195                 200                 205

Ile Met Ser Arg Val Ile Met Ser Lys Ile Asp Gly Glu Ser Leu Ser
210                 215                 220

Glu Asp Asp Leu Ile Gly Phe Phe Thr Ile Leu Leu Leu Gly Gly Ile
225                 230                 235                 240

Asp Asn Thr Ala Arg Phe Leu Ser Ser Val Phe Trp Arg Leu Ala Trp
            245                 250                 255

Asp Ile Glu Leu Arg Arg Arg Leu Ile Ala His Pro Glu Leu Ile Pro
            260                 265                 270

Asn Ala Val Asp Glu Leu Leu Arg Phe Tyr Gly Pro Ala Met Val Gly
            275                 280                 285

Arg Leu Val Thr Gln Glu Val Thr Val Gly Asp Ile Thr Met Lys Pro
290                 295                 300

Gly Gln Thr Ala Met Leu Trp Phe Pro Ile Ala Ser Arg Asp Arg Ser
305                 310                 315                 320

Ala Phe Asp Ser Pro Asp Asn Ile Val Ile Glu Arg Thr Pro Asn Arg
            325                 330                 335

His Leu Ser Leu Gly His Gly Ile His Arg Cys Leu Gly Ala His Leu
            340                 345                 350

Ile Arg Val Glu Ala Arg Val Ala Ile Thr Glu Phe Leu Lys Arg Ile
            355                 360                 365

Pro Glu Phe Ser Leu Asp Pro Asn Lys Glu Cys Glu Trp Leu Met Gly
            370                 375                 380

Gln Val Ala Gly Met Leu His Val Pro Ile Ile Phe Pro Lys Gly Lys
385                 390                 395                 400

Arg Leu Ser Glu

<210> SEQ ID NO 20
<211> LENGTH: 461
<212> TYPE: PRT
<213> ORGANISM: Streptomyces coelicolor

<400> SEQUENCE: 20

Met Thr Val Glu Ser Val Asn Pro Glu Thr Arg Ala Pro Ala Ala Pro
1               5                   10                  15

Gly Ala Pro Glu Leu Arg Glu Pro Val Ala Gly Gly Val Pro
            20                  25                  30

Leu Leu Gly His Gly Trp Arg Leu Ala Arg Asp Pro Leu Ala Phe Met
            35                  40                  45

Ser Gln Leu Arg Asp His Gly Asp Val Val Arg Ile Lys Leu Gly Pro
50                  55                  60

Lys Thr Val Tyr Ala Val Thr Asn Pro Glu Leu Thr Gly Ala Leu Ala
65                  70                  75                  80

Leu Asn Pro Asp Tyr His Ile Ala Gly Pro Leu Trp Glu Ser Leu Glu
            85                  90                  95

Gly Leu Leu Gly Lys Glu Gly Val Ala Thr Ala Asn Gly Pro Leu His
            100                 105                 110
```

```
Arg Arg Gln Arg Arg Thr Ile Gln Pro Ala Phe Arg Leu Asp Ala Ile
            115                 120                 125

Pro Ala Tyr Gly Pro Ile Met Glu Glu Glu Ala His Ala Leu Thr Glu
        130                 135                 140

Arg Trp Gln Pro Gly Lys Thr Val Asp Ala Thr Ser Glu Ser Phe Arg
145                 150                 155                 160

Val Ala Val Arg Val Ala Ala Arg Cys Leu Leu Arg Gly Gln Tyr Met
                165                 170                 175

Asp Glu Arg Ala Glu Arg Leu Cys Val Ala Leu Ala Thr Val Phe Arg
                180                 185                 190

Gly Met Tyr Arg Arg Met Val Val Pro Leu Gly Pro Leu Tyr Arg Leu
                195                 200                 205

Pro Leu Pro Ala Asn Arg Arg Phe Asn Asp Ala Leu Ala Asp Leu His
        210                 215                 220

Leu Leu Val Asp Glu Ile Ile Ala Glu Arg Arg Ala Ser Gly Gln Lys
225                 230                 235                 240

Pro Asp Asp Leu Leu Thr Ala Leu Leu Glu Ala Lys Asp Asp Asn Gly
                245                 250                 255

Asp Pro Ile Gly Glu Gln Glu Ile His Asp Gln Val Val Ala Ile Leu
            260                 265                 270

Thr Pro Gly Ser Glu Thr Ile Ala Ser Thr Ile Met Trp Leu Leu Gln
        275                 280                 285

Ala Leu Ala Asp His Pro Glu His Ala Asp Arg Ile Arg Asp Glu Val
        290                 295                 300

Glu Ala Val Thr Gly Gly Arg Pro Val Ala Phe Glu Asp Val Arg Lys
305                 310                 315                 320

Leu Arg His Thr Gly Asn Val Ile Val Glu Ala Met Arg Leu Arg Pro
                325                 330                 335

Ala Val Trp Val Leu Thr Arg Arg Ala Val Ala Glu Ser Glu Leu Gly
                340                 345                 350

Gly Tyr Arg Ile Pro Ala Gly Ala Asp Ile Ile Tyr Ser Pro Tyr Ala
        355                 360                 365

Ile Gln Arg Asp Pro Lys Ser Tyr Asp Asn Leu Glu Phe Asp Pro
        370                 375                 380

Asp Arg Trp Leu Pro Glu Arg Ala Ala Asn Val Pro Lys Tyr Ala Met
385                 390                 395                 400

Lys Pro Phe Ser Ala Gly Lys Arg Lys Cys Pro Ser Asp His Phe Ser
                405                 410                 415

Met Ala Gln Leu Thr Leu Ile Thr Ala Ala Leu Ala Thr Lys Tyr Arg
            420                 425                 430

Phe Glu Gln Val Ala Gly Ser Asn Asp Ala Val Arg Val Gly Ile Thr
        435                 440                 445

Leu Arg Pro His Asp Leu Leu Val Arg Pro Val Ala Arg
        450                 455                 460

<210> SEQ ID NO 21
<211> LENGTH: 10
<212> TYPE: PRT
<213> ORGANISM: Streptomyces coelicolor
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
```

```
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 21

Phe Xaa Xaa Gly Xaa Arg Xaa Cys Xaa Gly
1               5                  10

<210> SEQ ID NO 22
<211> LENGTH: 19
<212> TYPE: DNA
<213> ORGANISM: Artificial Sequence
<220> FEATURE:
<223> OTHER INFORMATION: Ribosomal binding site

<400> SEQUENCE: 22
tttaagaagg agatatacc                                                19
```

FUSION PROTEINS USEFUL FOR MODIFYING TERPENES

CROSS-REFERENCE TO RELATED APPLICATIONS

This application claims priority to U.S. Provisional Patent Application Ser. No. 62/993,629, filed on Mar. 23, 2020, which is hereby incorporated by reference.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of production of modifying terpenes.

REFERENCE TO A "SEQUENCE LISTING" SUBMITTED AS ASCII TEXT FILES VIA EFS-WEB

The Sequence Listing written in file 2019-108-02_Sequence_Listing_ST25.txt created on Mar. 19, 2021, 82,950 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Terpenes are a large class of organic compounds, primarily produced by plants and constitute the main components of essential oils. A typical monoterpene ($C_{10}$), such as limonene, is a cyclic hydrocarbon molecule ($C_{10}H_{16}$) and can be used as a precursor of fuel additives, fragrances, insecticides, and pharmaceuticals[1]. Production of terpenes in the microbial system is considered a more sustainable and stable alternative to the isolation from natural plants or chemical synthesis. Functionalization of the terpene carbon backbone by enzymes such as cytochrome P450s can further expand the range of bio-based compounds which frequently can be converted to products of commercial interest[2,3]. For example, limonene can be oxidized by P450 (CYP153) to perillyl alcohol, a precursor of promising anti-cancer agents[4,5]. While P450s play an important role in the decorations and modifications of terpenes essential for the new bioactivities, the hydrophobicity and volatility of terpene molecules could severely limit the availability of the substrate around the enzyme and turn out a low enzymatic conversion efficiency. Particularly, when a solvent overlay is used to improve the production titer during the microbial production, it facilitates the extraction of terpenes to the overlay from the cell and also worsens the subsequent enzymatic reaction efficiencies[5].

To overcome the low availability of hydrophobic substrates for downstream enzymes such as P450s, one possible strategy is to create a spatial favorability that improves the proximity between the enzyme and the substrate[6]. For example, engineering fusion proteins[7,8], protein scaffolds[9] and compartmentalization of metabolic pathways[10] have been explored to achieve the proximity effect. Because of the simplicity and effectiveness, engineering an artificial fusion protein has been extensively used to modify enzymes toward efficient metabolic catalysis[11]. Using a short peptide linker sequence, two or more enzymes are combined together and generated a single polypeptide that exhibits more than one activity or increases consecutive enzyme reaction rates. In microbial production of isoprenoids, for example, a higher pinene production is reported by linking terpene synthase with geranyl pyrophosphate (GPP) synthase to overcome the product inhibition from GPP[12]. Similarly, an engineered fusion of isopentenyl diphosphate (IPP) isomerase and isoprene synthase shows a 3.3-fold increase in isoprene production[13]. For P450 enzymes, fusions of P450 with a heterologous cytochrome P450 reductase have also proven successful in various instances, such as a P450 TxtE linked to the reductase domain of P450BM3 for improved activity and regio-promiscuity in aromatic nitration[14].

Although engineering a fusion of P450 with a cytochrome P450 reductase is widely studied, it is still less reported for engineering a fusion between P450 and a biosynthetic pathway enzyme probably because of the complex structural conformation of P450 enzymes and the multi-factor involving catalytic mechanism (i.e. heme, P450 reductase, NADPH, FAD, FMN, etc.) during the reaction[3,15,16].

SUMMARY OF THE INVENTION

The present invention provides for a fusion protein comprising a fusion protein comprising: (a) a terpene synthase (TS), or a homolog thereof, (b) a peptide linker, and (c) a P450 enzyme, or a homolog thereof (or other modifying enzyme). The term "terpene synthase" also encompasses a terpene cyclase. In some embodiments, the modifying enzyme is a transaminase, N-oxygenase, or methyl-transferase.

In some embodiments, the TS is 1,8-cineole synthase, sesquiterpene epi-isozizaene synthase, (R)-limonene synthase, (S)-limonene synthase, valencene synthase, (−)-alpha-terpineol synthase, (+)-alpha-pinene synthase, (−)-alpha-pinene synthase, (+)-beta-pinene synthase, (−)-beta-pinene synthase, vetispiradiene synthase, amorphadiene synthase, curcumene synthase, bisabolene synthase, farnesene synthase, cadinene synthase, or aristolochene synthase.

In some embodiments, the TS comprises an amino acid sequence having at least 70%, 75%, 80%, 85%, 90%, 95% or 99% identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:15, SEQ ID NO:16. In some embodiments, the TS comprises the amino acid sequence Asp-Asp-Xaa-Xaa-Asp (DDXXD) (SEQ ID NO:17) or Asp-Asp-Xaa-Xaa-Glu (DDXXE) (SEQ ID NO:18).

In some embodiments, the P450 enzyme is 1,8-cineole 2-endo-monooxygenase or epi-isozizaene 5-monooxygenase. In some embodiments, the P450 enzyme comprises an amino acid sequence having at least 70%, 80%, 90%, 95%, or 99% identity with SEQ ID NO:19 or SEQ ID NO:20.

In some embodiments, the P450 enzyme, or homolog thereof, comprises FXXGXRXCXG (SEQ ID NO:21), or CXG, which forms part of the heme-binding domain and is important for heme-binding, and/or EXXR which forms part of the K-helix which are important for stabilizing the core and heme-binding. In some embodiments, the P450 enzyme comprises the amino acid sequence Glu-Xaa-Xaa-Arg (EXXR) motif. In some embodiments, the P450 enzyme comprises the amino acid sequence Cys-Xaa-Gly (CXG) motif.

In some embodiments, the peptide linker comprises of 0 (or 1) to 1000 amino acid residues. In some embodiments, the peptide linker comprises of 0 (or 1) to 500 amino acid residues. In some embodiments, the peptide linker comprises of 0 (or 1) to 100 amino acid residues. In some embodiments, the peptide linker comprises of 0 (or 1) to 50 amino acid residues. In some embodiments, the peptide linker comprises of 1, 2, 3, 4, or 5 repeats of the amino acid sequence GSG. In some embodiments, the peptide link can comprise any amino acid sequence that does not interfere in the enzymatic activity of the terpene synthase (TS), or a homolog thereof, and the P450 enzyme, or a homolog thereof (or other modifying enzyme).

The present invention provides for a genetically modified host cell capable of producing a modified terpenes, said genetically modified host cell comprising the fusion protein of the present invention.

The present invention provides for a nucleic acid comprising a nucleotide sequence encoding the fusion protein of the present invention operatively linked to a promoter.

The present invention provides for a vector comprising the nucleic acid of the present invention.

The present invention provides for a genetically modified host cell capable of producing a modified terpenes, said genetically modified host cell comprising the nucleic acid of the present invention or a vector of the present invention. In one embodiment, the nucleotide sequence encoding the fusion protein is codon optimized for the genetically modified host cell.

In some embodiments, the genetically modified host cell is a bacterium.

In some embodiments, the bacterium is of the genus *Escherichia, Enterobacter, Azotobacter, Erwinia, Bacillus, Pseudomonas, Klebsielia, Proteus, Salmonella, Serratia, Shigella, Rhizobia, Vitreoscilla,* or *Paracoccus*.

In some embodiments, the genetically modified host cell is a eukaryotic cell. In some embodiments, the eukaryotic cell is a fungal cell. In some embodiments, the genetically modified host cell is a eukaryotic cell. In some embodiments, the fungal cell is a yeast. In some embodiments, the genetically modified host cell is a yeast of the genus *Saccharomyces*. In some embodiments, the genetically modified host cell is *Saccharomyces cerevisiae*.

The present invention provides for a method for producing a modified terpene comprising: (a) providing the genetically modified host cell of the present invention, or a culture thereof, (b) culturing or growing the genetically modified host cell to produce the modified terpene, (c) optionally extracting or separating the modified terpene from the culture, and (d) optionally introducing a fuel additive to the extracted or separated the modified terpene. In some embodiments, the step of extracting or separating the modified terpene is concurrent or subsequent to the culturing or growing step.

The present invention provides for a fuel composition comprising: (a) a modified terpene produced by the fusion protein of the present invention; and (b) a fuel additive.

In some embodiments, the fuel composition further comprises a tricyclic sesquiterpene (such as epi-isozizaene, pentalenene, or α-isocomene), or hydrogenated tricyclic sesquiterpene, α-zingiberene, β-sesquiphellandrene, α-bisabolene, β-bisabolene, γ-bisabolene, curcumene, gossonorol, or any monocyclic sesquiterpene taught in U.S. Pat. No. 9,109,175 (herein incorporated by reference), or a mixture thereof.

In one embodiment, the fuel additive that is mixed with the hydrogenation product of the tricyclic sesquiterpene is a chemical compound or component added to the fuel composition to alter the property of the fuel, e.g., to improve engine performance, fuel handling, fuel stability, or for contaminant control, etc. The nature and amount of the one or more additives depends on the desired use of the final fuel composition. Some nonlimiting examples of conventional fuel additives include antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof.

In some embodiments, the fuel composition of the present invention may further comprise a conventional fuel component derived from petroleum, coal, wood, or any other hydrocarbon source. Nonlimiting examples of conventional fuel components include, but are not limited to, diesel fuels, jet fuels, kerosene, gasoline, and Fischer-Tropsch derived fuels. In some embodiments, the conventional fuel component is derived from petroleum or coal. In certain embodiments, the fuel component is or comprises a diesel fuel, a jet fuel, kerosene, gasoline, or a combination thereof. In other embodiments, the fuel component is or comprises a distillate diesel fuel.

In certain embodiments, the fuel composition of the present invention is intended for use in diesel engines. In other embodiments, the fuel composition of the present invention is intended for use in jet engines and/or missile propulsion systems. As such, the fuel compositions disclosed herein can be used as a fuel for internal combustion engines such as gasoline engines, diesel engines, jet engines, and/or missile propulsion systems.

In yet another aspect, the present invention provides a vehicle comprising an internal combustion engine, a fuel tank connected to the internal combustion engine, and a fuel composition in the fuel tank, wherein the fuel composition is the fuel composition of the present invention, wherein the fuel combustion is used to power the internal combustion engine. In one embodiment, the internal combustion engine is a diesel engine. In another embodiment, the internal combustion engine is a jet engine or missile propulsion system.

In a further aspect, the present invention provides a method of powering an engine comprising the step of combusting a fuel composition of the present invention in the engine. In one embodiment, the engine is a diesel engine. In another embodiment, the engine is a jet engine or a missile propulsion system.

Other objects, features, and advantages of the present invention will be apparent to one of skill in the art from the following detailed description and figures.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
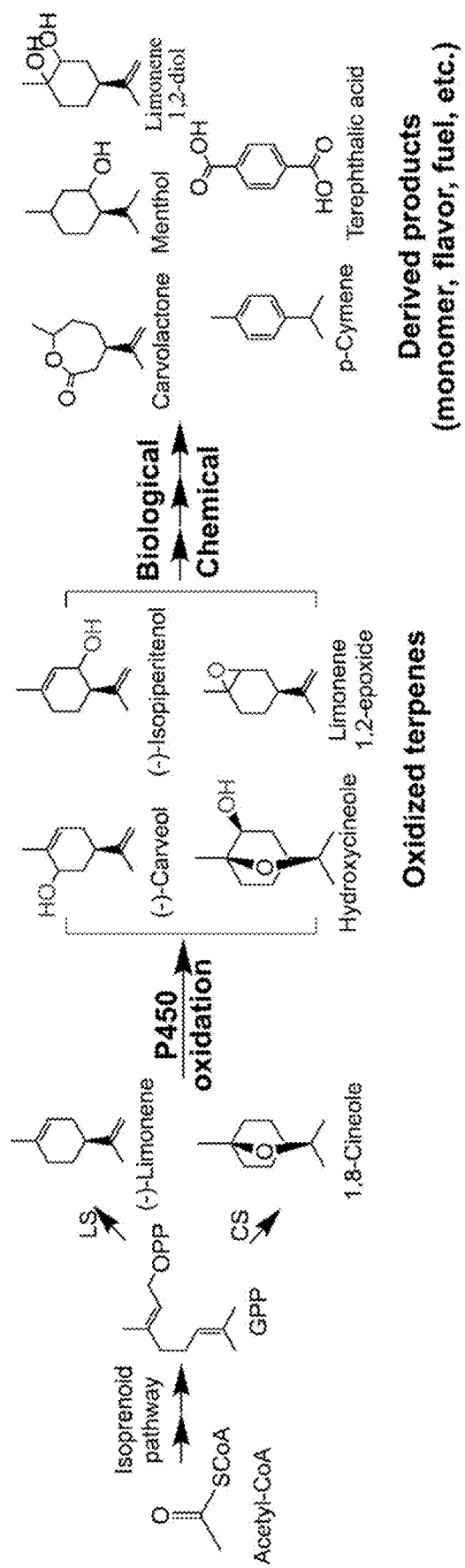
FIG. 1. Oxidation of (−)-limonene and 1,8-cineole.
Figure 2A:
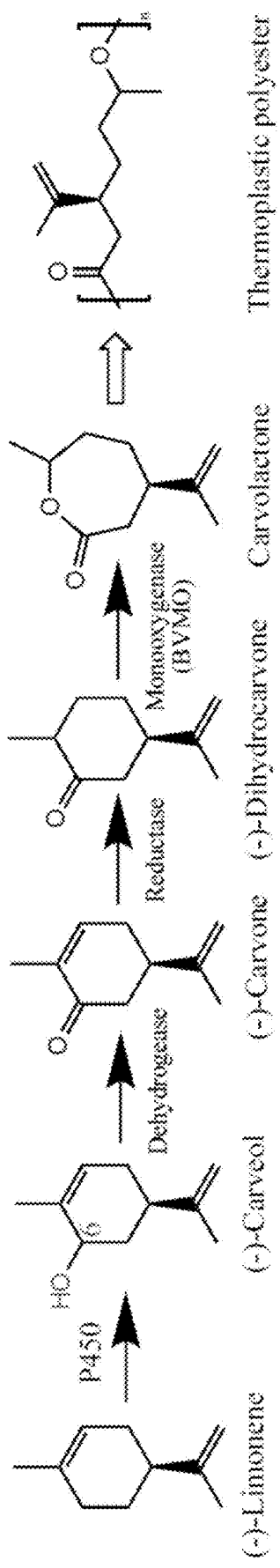
FIG. 2A. Biosynthetic pathway of carvolactone.
Figure 2B:
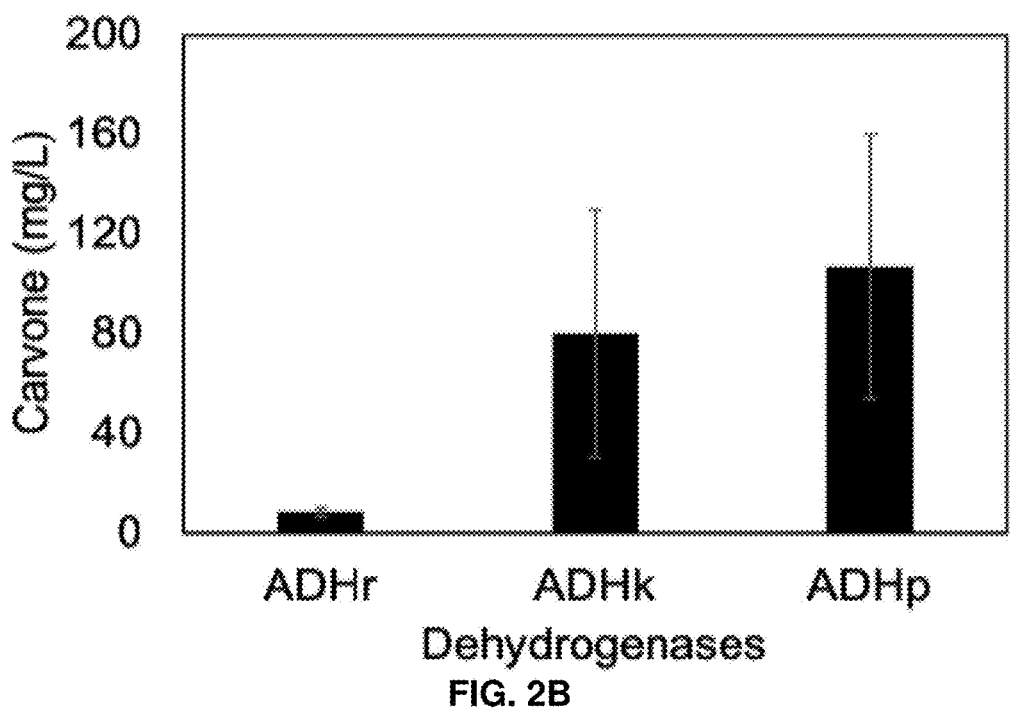
FIG. 2B. Carvone yield vs. dehydrogenase variants.
Figure 2C:
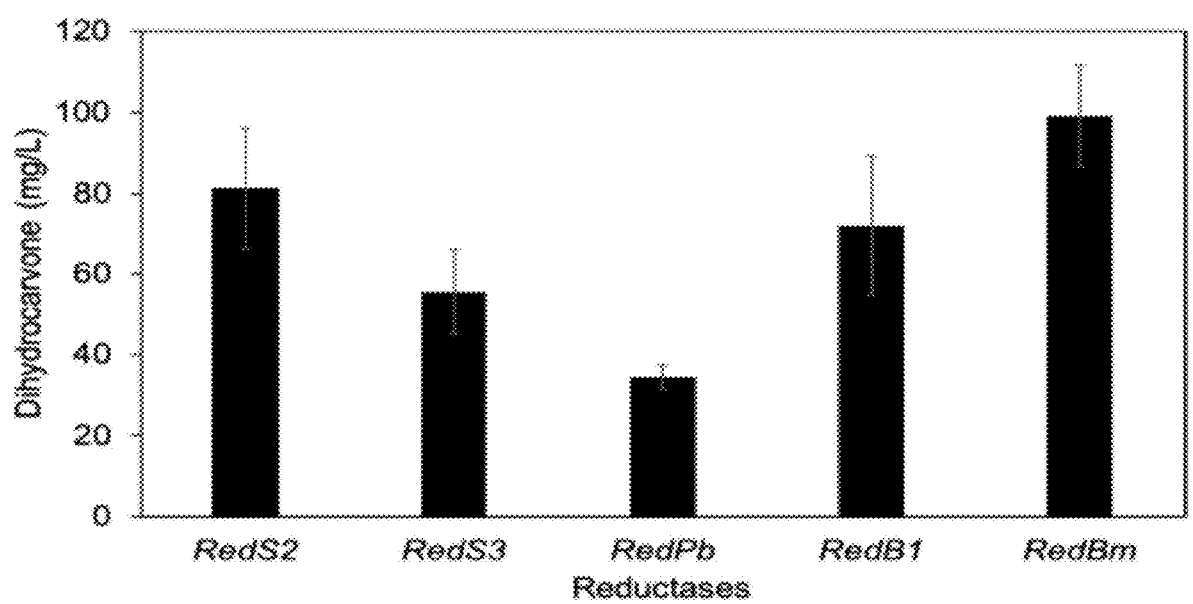
FIG. 2C. Dihydrocarvone yield vs. reductase variants.
Figure 2D:
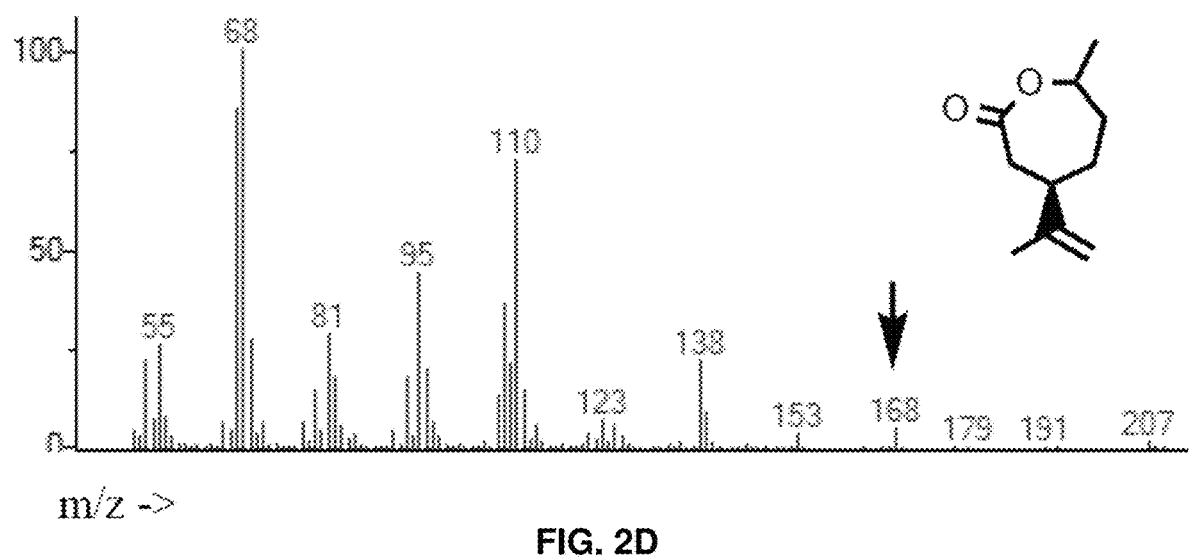
FIG. 2D. Mass spectra showing carvolactone peak.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" as used herein means a value that includes 10% less and 10% more than the value referred to.

The terms "host cell" and "host microorganism" are used interchangeably herein to refer to a living biological cell, such as a microbe, that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. The term "heterologous" as used herein refers to a structure or molecule wherein at least one of the following is true: (a) the structure or molecule is foreign to (i.e., not naturally found in) a given host microorganism; or (b) the structure or molecule may be naturally found in a given host microorganism, but in an unnatural (e.g., greater than expected) amount. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (Biochem. 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

Terpenes are a large class of organic compounds, primarily produced by plants and constitute the main components of essential oils. Functionalization of the terpene carbon backbone using various downstream processing enzymes, such as cytochrome P450 enzymes, could derive many useful compounds that can be converted to higher value products. Production of terpenes and their functionalized products through microbial metabolic engineering are considered a favorable green strategy compared with isolation from the natural plants or chemical synthesis. However, as terpenes are usually hydrophobic and volatile compounds, the severe evaporation limits their availabilities surrounding downstream processing enzymes (such as cytochrome P450) toward adding functional groups. Particularly, when a solvent overlay is used to trap terpenes and prevent evaporation during the microbial production, it facilitates the isolation of terpenes from the cell and worsens the downstream processing reaction.

One possible solution is to engineer a fusion protein between terpene synthase and downstream processing enzymes that could improve the spatial favorability for downstream processing enzymes and the terpene substrate, which in turn would improve the substrate availability for downstream conversion. In some embodiments, an enzyme fusion strategy is developed by linking a terpene synthase (or a terpene cyclase) and downstream processing enzyme, specifically cytochrome P450 enzymes. In some embodiments, a series of fusion proteins is engineered between 1,8-cineole synthase and P450cin (CYP176A1) with different lengths of peptide linker to investigate the hydroxylation of 1,8-cineole to produce hydroxycineole. The production of hydroxycineole from both in vitro and in vivo conditions is compared between the fusion and non-fusion proteins. Results show the engineered enzyme fusion is more efficient than non-fused individual enzymes, suggesting a feasible strategy for efficient production of functionalized terpenes as well as possible application during the production of terpene-based bioproducts. Compared with the non-fused enzymes, results show that hydroxycineole production under the in vitro conditions is increased up to 5.2 folds from the enzyme fusion and the production rate is up to 10.5 folds faster. The engineered enzyme fusion is also integrated into a 1,8-cineole overproducing E. coli strain using the mevalonate pathway to investigate the hydroxylation of 1,8-cineole at the in vivo conditions. Results show that the enzyme fusion produced up to 2.8-fold more hydroxycineole than the non-fused enzymes. Thus, the engineered fusion showed higher efficiency during the hydroxylation of 1,8-cineole from both in vitro and in vivo results. This suggests that engineering an enzyme fusion between terpene synthase (or terpene cyclase) and downstream processing enzyme (such as P450) presents a feasible strategy for efficient production of functionalized terpenes, as well as possible applications (i.e. epoxidation, cyclopropanation, and, nitration, and the like) during the production of terpene-based bioproducts (such as, limonene-1,2-epoxide, perillyl alcohol, artemisinic alcohol, and the like).

In some embodiments, the modifying enzyme is a transaminase, N-oxygenase, or methyl-transferase. In some embodiments, the P450 or other modifying enzyme, or homolog thereof, is any enzyme listed in Table 1.

TABLE 1

Suitable modifying enzymes and corresponding terpene substrate and products thereof.

| Potential reaction | Terpene substrates | Products | Enzyme |
| --- | --- | --- | --- |
| Oxidation | Amorphadiene | Artemsinic acid | 1.14.14.114 |
|  | Valencene | Nootkatone | 1.14.14.1 |
|  | Limonene | Perillyl alcohol | 1.14.15.1 |

TABLE 1-continued

Suitable modifying enzymes and corresponding terpene substrate and products thereof.

| Potential reaction | Terpene substrates | Products | Enzyme |
|---|---|---|---|
| | Limonene | Carveol | 1.14.14.51 |
| | Limonene | Isopiperitenol | 1.14.14.99 |
| | Limonene | Limonene-1,2-epoxide | 1.14.13.107 |
| | Terpineol | Sobrerol (Mucolytic agent) | 1.14.14.1 |
| | Pinene | Verbenol (insect pheromone) | 1.14.15.1 |
| Amination | Ketones | Terpene amines | transaminase |
| Nitration | Terpene amine | Nitro terpenoids | N-oxygenase |
| Cyclopropanation | | | Methyl transferase |

Enzymes, and Nucleic Acids Encoding Thereof

A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) Tet. Lett. 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in E. coli. See Shine et al. (1975) Nature 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) *Proc. Natl. Acad. Sci. USA*, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of the modified terpene ensured. When added, any intermediate is present in an excess amount in the culture medium.

Any means for extracting or separating the modified terpene from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC).

In some embodiments, the 1,8-cineole synthase (CS), or a homologous enzyme thereof, has an amino acid sequence having at least 70% identity to the amino acid sequence of *Streptomyces clavuligerus* 1,8-cineole synthase which is as follows:

```
                                              (SEQ ID NO: 1)
         10         20         30         40
  MPAGHEEFDI PFPSRVNPFH ARAEDRHVAW MRAMGLITGD 50         60         70         80
  AAEATYRRWS PAKVGARWFY LAQGEDLDLG CDIFGWFFAY 90        100        110        120
  DDHFDGPTGT DPRQTAAFVN RTVAMLDPRA DPTGEHPLNI 130        140        150        160
  AFHDLWQRES APMSPLWQRR AVDHWTQYLT AHITEATNRT 170        180        190        200
  RHTSPTIADY LELRHRTGFM PPLLDLIERV WRAEIPAPVY 210        220        230        240
  TTPEVQTLLH TTNQNINIVN DVLSLEKEEA HGDPHNLVLV 250        260        270        280
  IQHERQSTRQ QALATARRMI DEWTDTFIRT EPRLPALCGR 290        300        310        320
  LGIPLADRTS LYTAVEGMRA AIRGNYDWCA ETNRYAVHRP

330
  TGTGRATTPW
```

In some embodiments, the 1,8-cineole synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of 1,8-cineole synthase, presumably through binding to $Mg^{2+}$.

In some embodiments, the epi-isozizaene synthase (EIZS), or a homologous enzyme thereof, has an amino acid sequence having at least 70% identity to the amino acid sequence of *Streptomyces coelicolor* epi-isozizaene synthase which is as follows:

```
                                              (SEQ ID NO: 2)
         10         20         30         40
  MHAFPHGTTA TPTAIAVPPS LRLPVIEAAF PRQLHPYWPK 50         60         70         80
  LQETTRTWLL EKRLMPADKV EEYADGLCYT DLMAGYYLGA 90        100        110        120
  PDEVLQAIAD YSAWFFVWDD RHDRDIVHGR AGAWRRLRGL 130        140        150        160
  LHTALDSPGD HLHHEDTLVA GFADSVRRLY AFLPATWNAR 170        180        190        200
  FARHFHTVIE AYDREFHNRT RGIVPGVEEY LELRRLTFAH 210        220        230        240
  WIWTDLLEPS SGCELPDAVR KHPAYRRAAL LSQEFAAWYN 250        260        270        280
  DLCSLPKEIA GDEVHNLGIS LITHHSLTLE EAIGEVRRRV
```

```
           290         300         310         320
EECITEFLAV  ERDALRFADE  LADGTVRGKE  NMRNWFSSVY 330         340         350         360
LSGAVRANVG  WFHHESGRYM  VDSWDDRSTP  PYVNNEAAGE

K
```

In some embodiments, the epi-isozizaene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of epi-isozizaene synthase, presumably through binding to $Mg^{2+}$.

In some embodiments, the (R)-limonene synthase, or a homologous enzyme thereof, has an amino acid sequence having at least 70% identity to the amino acid sequence of *Citrus limon* (R)-limonene synthase which is as follows:

```
                                          (SEQ ID NO: 3)
            10          20          30          40
MSSCINPSTL  VTSVNAFKCL  PLATNKAAIR  IMAKYKPVQC 50          60          70          80
LISAKYDNLT  VDRRSANYQP  SIWDHDFLQS  LNSNYTDEAY 90         100         110         120
KRRAEELRGK  VKIAIKDVIE  PLDQLELIDN  LQRLGLAHRF 130         140         150         160
ETEIRNILNN  IYNNNKDYNW  RKENLYATSL  EFRLLRQHGY 170         180         190         200
PVSQEVENGF  KDDQGGFICD  DFKGILSLHE  ASYYSLEGES 210         220         230         240
IMEEAWQFTS  KHLKEVMISK  NMEEDVEVAE  QAKRALELPL 250         260         270         280
HWKVPMLEAR  WFIHIYERRE  DKNHLLLELA  KMEFNTLQAI 290         300         310         320
YQEELKEISG  WWKDTGLGEK  LSFARNRLVA  SFLWSMGIAF 330         340         350         360
EPQFAYCRRV  LTISIALITV  IDDIYDVYGT  LDELEIFTDA 370         380         390         400
VERWDINYAL  KHLPGYMKMC  FLALYNFVNE  FAYYVLKQQD 410         420         430         440
FDLLLSIKNA  WLGLIQAYLV  EAKWYHSKYT  PKLEEYLENG 450         460         470         480
LVSITGPLII  TISYLSGTNP  IIKKELEFLE  SNPDIVHWSS 490         500         510         520
KIFRLQDDLG  TSSDEIQRGD  VPKSIQCYMH  ETGASEEVAR 530         540         550         560
QHIKDMMRQM  WKKVNAYTAD  KDSPLIGTTT  EFLLNLVRMS 570         580         590         600
HFMYLHGDGH  GVQNQETIDV  GFTLLFQPIP  LEDKHMAFTA

SPGTKG
```

In some embodiments, the (R)-limonene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of (R)-limonene synthase, presumably through binding to $Mg^{2+}$.

In some embodiments, the (S)-limonene synthase, or a homologous enzyme thereof, has an amino acid sequence having at least 70% identity to the amino acid sequence of *Cannabis sativa* (S)-limonene synthase which is as follows:

```
                                          (SEQ ID NO: 4)
            10          20          30          40
MQCIAFHQFA  SSSSLPIWSS  IDNRFTPKTS  ITSISKPKPK 50          60          70          80
LKSKSNLKSR  SRSSTCYSIQ  CTVVDNPSST  ITNNSDRRSA 90         100         110         120
NYGPPIWSFD  FVQSLPIQYK  GESYTSRLNK  LEKDVKRMLI 130         140         150         160
GVENSLAQLE  LIDTIQRLGI  SYRFENEIIS  ILKEKFTNNN 170         180         190         200
DNPNPNYDLY  ATALQFRLLR  QYGFEVPQEI  FNNFKNHKTG 210         220         230         240
EFKANISNDI  MGALGLYEAS  FHGKKGESIL  EEARIFTTKC 250         260         270         280
LKKYKLMSSS  NNNNMTLISL  LVNHALEMPL  QWRITRSEAK 290         300         310         320
WFIEEIYERK  QDMNPTLLEF  AKLDENMLQS  TYQEELKVLS 330         340         350         360
RWWKDSKLGE  KLPFVRDRLV  ECFLWQVGVR  FEPQFSYFRI 370         380         390         400
MDTKLYVLLT  IIDDMHDIYG  TLEELQLFTN  ALQRWDLKEL 410         420         430         440
DKLPDYMKTA  FYFTYNFTNE  LAFDVLQEHG  FVHIEYFKKL 450         460         470         480
MVELCKHHLQ  EAKWFYSGYK  PTLQEYVENG  WLSVGGQVIL 490         500         510         520
MHAYFAFTNP  VTKEALECLK  DGHPNIVRHA  SIILRLADDL 530         540         550         560
GTLSDELKRG  DVPKSIQCYM  HDTGASEDEA  REHIKYLISE 570         580         590         600
SWKEMNNEDG  NINSFFSNEF  VQVCQNLGRA  SQFIYQYGDG 610         620
HASQNNLSKE  RVLGLIITPI  PM
```

In some embodiments, the (S)-limonene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of (S)-limonene synthase, presumably through binding to $Mg^{2+}$.

In some embodiments, the valencene synthase, or a homologous enzyme thereof, has an amino acid sequence having at least 70% identity to the amino acid sequence of *Vitis vinifera* valencene synthase which is as follows:

```
                                          (SEQ ID NO: 5)
            10          20          30          40
MSTQVSASSL  AQIPQPKNRP  VANFHPNIWG  DQFITYTPED 50          60          70          80
KVTRACKEEQ  IEDLKKEVKR  KLTAAAVANP  SQLLNFIDAV 90         100         110         120
QRLGVAYHFE  QEIEEALQHI  CNSFHDCNDM  DGDLYNIALG 130         140         150         160
FRLLRQQGYT  ISCDIFNKFT  DERGRFKEAL  ISDVRGMLGL
```

-continued

```
            170         180         190         200
YEAAHLRVHG  EDILAKALAF  TTTHLKAMVE  SLGYHLAEQV 210         220         230         240
AHALNRPIRK  GLERLEARWY  ISVYQDEAFH  DKTLLELAKL 250         260         270         280
DENLVQSLHK  EELSNLARWW  KELDFATKLP  FARDRLVEGY 290         300         310         320
FWMHGVYFEP  QYLRGRRILT  KVIAMTSILD  DIHDAYGTPE 330         340         350         360
ELKLFIEAIE  RWDINSINQL  PEYMKLCYVA  LLDVYKEIEE 370         380         390         400
EMEKEGNQYR  VHYAKEVMKN  QVRAYFAEAK  WLHEEHVPAF 410         420         430         440
EEYMRVALAS  SGYCLLATTS  FVGMGEIATK  EAFDWVTSDP 450         460         470         480
KIMSSSNFIT  RLMDDIKSHK  FEQKRGHVTS  AVECYMKQYG 490         500         510         520
VSEEQVYSEF  QKQIENAWLD  INQECLKPTA  VSMPLLARLL 530         540         550
NFTRTMDVIY  KEQDSYTHVG  KVMRDNIASV

FINAVI
```

In some embodiments, the valencene synthase comprises the amino acid sequence Asp-Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of valencene synthase, presumably through binding to $Mg^{2+}$.

In some embodiments, the (−)-alpha-terpineol synthase, or a homologous enzyme thereof, has an amino acid sequence having at least 70% identity to the amino acid sequence of *Vitis vinifera* (−)-alpha-terpineol synthase which is as follows:

```
                                    (SEQ ID NO: 6)
            10          20          30          40
MALSMLSSIP  NLITHTRLPI  IIKSSSCKAS  PRGIKVKIGN 50          60          70          80
SNCEEIIVRR  TANYHPTIWD  YDYVQSLRSD  YVGETYTRRL 90          100         110         120
DKLKRDVKPM  LGKVKKPLDQ  LELIDVLQRL  GIYYHFKDEI 130         140         150         160
KRILNGIYNQ  YNRHEEWQKD  DLYATALEFR  LLRQHGYDVP 170         180         190         200
QDVFSRFKDD  TGSFKACLCE  DMKGMLCLYE  ASYLCVQGES 210         220         230         240
TMEQARDFAH  RHLGKGLEQN  IDQNLAIEVK  HALELPLHWR 250         260         270         280
MPRLEARWFI  DVYEKRQDMN  PILLEFAKLD  FNMVQATHQE 290         300         310         320
DLRHMSSWWS  STRLGEKLNF  ARDRLMENFL  WTVGVIFEPQ 330         340         350         360
YGYCRRMSTK  VNTLITIIDD  VYDVYGTMDE  LELFTDVVDR 370         380         390         400
WDINAMDPLP  EYMKLCFLAL  YNSTNEMAYD  ALKEHGLHIV
```

```
            410         420         430         440
SYLRKAWSDL  CKSYLLEAKW  YYSRYTPSLQ  EYISNSWISI 450         460         470         480
SGPVILVHAY  FLVANPITKE  ALQSLERYHN  IIRWSSMILR 490         500         510         520
LSDDLGTSLD  ELKRGDVPKS  IQCYMYETGA  SEEDARKHTS 530         540         550         560
YLIGETWKKL  NEDGAVESPF  PETFIGIAMN  LARMAQCMYQ 570         580         590
HGDGHGIEYG  ETEDRVLSLL  VEPIPSLSSE
```

In some embodiments, the (−)-alpha-terpineol synthase comprises the amino acid Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of (−)-alpha-terpineol synthase, presumably through binding to $Mg^{2+}$.

In some embodiments, the (+)-alpha-pinene synthase, or a homologous enzyme thereof, has an amino acid sequence having at least 70% identity to the amino acid sequence of *Pinus taeda* (+)-alpha-pinene synthase which is as follows:

```
                                    (SEQ ID NO: 7)
            10          20          30          40
MALVSAVPLN  SKLCLRRTLF  GFSHELKAIH  STVPNLGMCR 50          60          70          80
GGKSIAPSMS  MSSTTSVSNE  DGVPRRIAGH  HSNLWDDDSI 90          100         110         120
ASLSTSYEAP  SYRKRADKLI  GEVKNIFDLM  SVEDGVFTSP 130         140         150         160
LSDLHHRLWM  VDSVERLGID  RHFKDEINSA  LDHVYSYWTE 170         180         190         200
KGIGRGRESG  VTDLNSTALG  LRTLRLHGYT  VSSHVLDHFK 210         220         230         240
NEKGQFTCSA  IQTEGEIRDV  LNLFRASLIA  FPGEKIMEAA 250         260         270         280
EIFSTMYLKD  ALQKIPPSGL  SQEIEYLLEF  GWHTNLPRME 290         300         310         320
TRMYIDVFGE  DTTFETPYLI  REKLLELAKL  EFNIFHSLVK 330         340         350         360
RELQSLSRWW  KDYGFPEITF  SRHRHVEYYT  LAACIANDPK 370         380         390         400
HSAFRLGFGK  ISHMITILDD  IYDTFGTMEE  LKLLTAAFKR 410         420         430         440
WDPSSIECLP  DYMKGVYMAV  YDNINEMARE  AQKIQGWDTV 450         460         470         480
SYARKSWEAF  IGAYIQEAKW  ISSGYLPTFD  EYLENGKVSF 490         500         510         520
GSRITTLEPM  LTLGFPLPPR  ILQEIDFPSK  FNDLICAILR 530         540         550         560
LKGDTQCYKA  DRARGEEASA  VSCYMKDHPG  ITEEDAVNQV 570         580         590         600
NAMVDNLTKE  LNWELLRPDS  GVPISYKKVA  FDICRVFHYG 610         620
YKYRDGFSVA  SIEIKNLVTR  TVVETVPL
```

In some embodiments, the (+)-alpha-pinene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of (+)-alpha-pinene synthase, presumably through binding to $Mg^{2+}$.

In some embodiments, the (−)-alpha-pinene synthase, or a homologous enzyme thereof, has an amino acid sequence having at least 70% identity to the amino acid sequence of *Pinus taeda* (−)-alpha-pinene synthase which is as follows:

```
                                              (SEQ ID NO: 8)
            10          20          30          40
    MSPVSVISLP  SDLCLPTSFI  DRSGRELIPL  HITIPNVAMR 50          60          70          80
    RQGKLMTRAS  MSMNLRTAVS  DDAVIRRRGD  FHSNLWDDDL 90         100         110         120
    IQSLSSPYGE  PSYRERAERL  IGEVKNSENS  MSNEDGESIT 130         140         150         160
    PLDDLIQRLW  MVDSVERLGI  DRHFKKEIKS  ALDHVYRYWS 170         180         190         200
    EKGIGCGRES  VVTDLNSTAL  GLRTLRLHGY  DVSADVLNHE 210         220         230         240
    KNQSGQFACT  LKQTEDQIRT  VLNLYRASLI  AFPGEKVMDE 250         260         270         280
    AESFSAKYLK  EALQKIPVSS  FSREIGDVLE  YGWHTYLPRL 290         300         310         320
    EARNYIDVFG  QDTENSKSYM  KTEKLLELAK  LEFNIFHALQ 330         340         350         360
    KRELEYLVRW  WKGSGSPQMT  FCRHRHVEYY  TLASCIAFEP 370         380         390         400
    QHSGFRLGFA  KACHIITVLD  DMYDTFGTLD  ELELFTSAIK 410         420         430         440
    RWDPSATECL  PEYMKGVYMI  VYNTVNEMSQ  EADKAQGRDT 450         460         470         480
    LNYCRQAWEE  YIDAYMQEAK  WIASGEVPTF  EEYYENGKVS 490         500         510         520
    SGHRVSALQP  ILTTDIPFPE  HVLKEVDIPS  QLNDLASAIL 530         540         550         560
    RLRGDTRCYQ  ADRARGEEAS  CISCYMKDNP  GTTEEDALNH 570         580         590         600
    LNAMISDVIK  GLNWELLKPN  SSVPISAKKH  AFDISRAFHC 610         620
    GYKYRDGYSV  ANIETKSLVK  RTVIDPVTL
```

In some embodiments, the (−)-alpha-pinene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of (−)-alpha-pinene synthase, presumably through binding to $Mg^{2+}$.

In some embodiments, the (−)-beta-pinene synthase, or a homologous enzyme thereof, has an amino acid sequence having at least 70% identity to the amino acid sequence of *Artemisia annua* (−)-beta-pinene synthase which is as follows:

```
                                              (SEQ ID NO: 9)
            10          20          30          40
    MASMCTESSP  FLLCNSSISR  TNIVACNKQT  STLQAQVKNV 50          60          70          80
    ATIETTNRRS  ANYAPSLWSY  DFVQSLSSKY  KGDNYMARSR 90         100         110         120
    ALKGVVRTMI  LEANGIENPL  SLLNLVDDLQ  RLGISYHFLD 130         140         150         160
    EISNVLEKIY  LNFYKSPEKW  TNMDLNLRSL  GFRLLROHGY 170         180         190         200
    HIPQEIFKDF  IDVNGNFKGD  IISMLNLYEA  SYHSVEEESI 210         220         230         240
    LDDAREFTTK  YLKETLENIE  DQNIALFISH  ALVFPLHWMV 250         260         270         280
    PRVETSWFIE  VYPKKVGMNP  TVLEFAKLDF  NILQAVHQED 290         300         310         320
    MKKASRWWKE  TCWEKFGFAR  DRLVENFMWT  VAENYLPHFQ 330         340         350         360
    TGRGVLTKVN  AMITTIDDVY  DVYGTLPELE  LETNIVNSWD 370         380         390         400
    INAIDELPDY  LKICFLACYN  ATNELSYNTL  TNKGFFVHPY 410         420         430         440
    LKKAWQDLCN  SYIIEAKWEN  DGYTPTFNEF  IENAYMSIGI 450         460         470         480
    APIIRHAYLL  TLTSVTEEAL  QHIERAESMI  RNACLIVRLT 490         500         510         520
    NDMGTSSDEL  ERGDIPKSIQ  CYMHESGATE  MEARAYIKOF 530         540         550         560
    IVETWKKLNK  ERQEIGSEFP  QEFVDCVINL  PRMGHFMYTD 570         580
    GDKHGKPDMF  KPYVESLEVN  PI
```

In some embodiments, the (−)-beta-pinene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of (−)-beta-pinene synthase, presumably through binding to $Mg^{2+}$.

In some embodiments, the vetispiradiene synthase, or a homologous enzyme thereof, has an amino acid sequence having at least 70% identity to the amino acid sequence of *Solanum tuberosum* vetispiradiene synthase which is as follows:

```
                                             (SEQ ID NO: 10)
            10          20          30          40
    MTPAAVVMSN  YGEEEIVRPI  ADFSPSLWGD  RFHSFSLDNQ 50          60          70          80
    IAGKYAQEIE  TLKEQSRIIL  SASSRRTLAE  KLDLIDIVER 90         100         110         120
    LGIAYHFEKQ  IDDMLDQFYK  ADPNFEAHEY  NDLQTLSVQF 130         140         150         160
    RLLROHGYNI  SPKLFIRFQD  AKGKFKESLC  NDIKGLLNLY 170         180         190         200
    EASHVRTHGE  DILEEALAFS  TAHLESAAPH  LKSPLSKQVT 210         220         230         240
    HALEQSLHKS  IPRVETRYFI  SIYEEEEQKN  DVLLQFAKLD 250         260         270         280
    FNLLQMLHKQ  ELSEVSRWWK  DLDFVTTLPY  ARDRAVECYF 290         300         310         320
    WTMGVYAEPQ  YSQARVMLAK  TIAMISIVDD  TFDAYGIVKE
```

```
                    330        340        350        360
            LEIYTDAIQR WDISQIDRLP DYMKISYKAL LDLYNDYEME 370        380        390        400
            LSKDGRSDVV HYAKERMKEI VRNYFVEAKW FIEGYMPPVS 410        420        430        440
            EYLSNALATS TYYLLTTTSY LGMKSANKQD FEWLAKNPKI 450        460        470        480
            LEANVTLCRV IDDIATYEVE KGRGQIATGI ECYMRDYGVS 490        500        510        520
            TEKAMEKFQE MAETAWKDVN EGILRPTPVS TEILTRILNL 530        540        550
            ARIIDVTYKH NODGYTHPEK VLKPHIIALL VDSIEI
```

In some embodiments, the vetispiradiene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of vetispiradiene synthase, presumably through binding to $Mg^{2+}$.

In some embodiments, the amorphadiene synthase, or a homologous enzyme thereof, has an amino acid sequence having at least 70% identity to the amino acid sequence of *Artemisia annua* amorphadiene synthase which is as follows:

```
                                              (SEQ ID NO: 11)
                    10         20         30         40
            MSLTEEKPIR PIANFPPSIW GDQFLIYEKQ VEQGVEQIVN 50         60         70         80
            DLKKEVRQLL KEALDIPMKH ANLLKLIDEI QRLGIPYHFE 90        100        110        120
            REIDHALQCI YETYGDNWNG DRSSLWFRLM RKOGYYVTCD 130        140        150        160
            VENNYKDKNG AFKQSLANDV EGLLELYEAT SMRVPGEIIL 170        180        190        200
            EDALGFTRSR LSIMTKDAFS TNPALFTEIQ RALKQPLWKR 210        220        230        240
            LPRIEAAQYI PFYQQQDSHN KTLLKLAKLE FNLLQSLHKE 250        260        270        280
            ELSHVCKWWK AFDIKKNAPC LRDRIVECYF WGLGSGYEPQ 290        300        310        320
            YSRARVFFTK AVAVITLIDD TYDAYGTYEE LKIFTEAVER 330        340        350        360
            WSITCLDTLP EYMKPIYKLF MDTYTEMEEF LAKEGRTDLF 370        380        390        400
            NCGKEFVKEF VRNLMVEAKW ANEGHIPTTE EHDPVVIITG 410        420        430        440
            GANLLTTTCY LGMSDIFTKE SVEWAVSAPP LFRYSGILGR 450        460        470        480
            RLNDLMTHKA EQERKHSSSS LESYMKEYNV NEEYAQTLIY 490        500        510        520
            KEVEDVWKDI NREYLTTKNI PRPLLMAVIY LCQFLEVQYA 530        540
            GKDNFTRMGD EYKHLIKSLL VYPMSI
```

In some embodiments, the amorphadiene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of amorphadiene synthase, presumably through binding to $Mg^{2+}$.

In some embodiments, the curcumene synthase, or a homologous enzyme thereof, has an amino acid sequence having at least 70% identity to the amino acid sequence of *Pogostemon cablin* curcumene synthase which is as follows:

```
                                              (SEQ ID NO: 12)
                    10         20         30         40
            MAAFTANAVD MRPPVITIHP RSKDIFSQFS LDDKLOKQYA 50         60         70         80
            QGIEALKEEA RSMLMAAKSA KVMILIDTLE RLGLGYHFEK 90        100        110        120
            EIEEKLEAIY KKEDGDDYDL FTTALRFRLL ROHQRRVPCS 130        140        150        160
            VFDKFMNKEG KFEEEPLISD VEGLLSLYDA AYLQIHGEHI 170        180        190        200
            LQEALIFTTH HLTRIEPQLD DHSPLKLKLN RALEFPFYRE 210        220        230        240
            IPIIYAHFYI SVYERDDSRD EVLLKMAKLS YNFLQNLYKK 250        260        270        280
            ELSQLSRWWN KLELIPNLPY IRDSVAGAYL WAVALYFEPQ 290        300        310        320
            YSDVRMAIAK LIQIAAAVDD TYDNYATIRE AOLLTEALER 330        340        350        360
            LNVHEIDTLP DYMKIVYREV MSWSEDFERD ATIKEQMLAT 370        380        390        400
            PYFKAEMKKL GRAYNQELKW VMERQLPSFE EYMKNSEITS 410        420        430        440
            GVYIMFTVIS PYLNSATQKN IDWLLSQPRL ASSTAIVMRC 450        460        470        480
            CNDLGSNQRE SKGGEVMTSL DCYMKOHGAS KQETISKFKL 490        500        510        520
            IIEDEWKNLN EEWAATTCLP KVMVEIFRNY ARIAGFCYKN 530        540
            NGDAYTSPKI VQQCFDALFV NPLRI
```

In some embodiments, the curcumene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of curcumene synthase, presumably through binding to $Mg^{2+}$.

In some embodiments, the bisabolene synthase, or a homologous enzyme thereof, has an amino acid sequence having at least 70% identity to the amino acid sequence of *Pogostemon cablin* bisabolene synthase which is as follows:

```
                                              (SEQ ID NO: 13)
                    10         20         30         40
            MDAFATSPTT ALFETVNCNA HVAPMAGEDS SENRPASNYK 50         60         70         80
            PSTWDYEFLQ SLATTNNTVG EKHTRMADKL KEEVKSMMKG 90        100        110        120
            TMEPVAKLEL INIVQRLGLK YRFESEIKEE LFSLYKDGTD 130        140        150        160
            AWWVGNLHAT ALRFRLLREN GIFVPQDVFE TFKDKSGEFK
```

```
                                   170         180         190         200
                          SQLCKDVRGL  LSLYEASYLG  WEGEELLDEA  KKFSTTNLNN 210         220         230         240
                          VKESISSNTL  GRLVKHALNL  PLHWSAARYE  ARWFIDEYER 250         260         270         280
                          EENVIPNLLK  YAKLDENVVQ  SIHQKELGNL  ARWWVETGLD 290         300         310         320
                          KLGFVRNTLM  QNFMWGCAMA  FEPQYGKVRD  AAVKLGSLIT 330         340         350         360
                          MVDDVYDVYG  TLEELEIFTD  IVDRWDINGI  DKLPRNISMI 370         380         390         400
                          VLTMFNTANQ  ISYDLLRDRG  FNSIPHIAEA  WATLCKTYLK 410         420         430         440
                          EAKWYHSGYK  PTLEEYLENG  LVSISFVLSL  VTAYLQTERL 450         460         470         480
                          ENLTYESAAY  VNSVPPLVRY  SGLLNRLYND  LGTSSAEIAR 490         500         510         520
                          GDTLKSIQCY  MTQTGATEEV  AREHIKGLVH  EAWKGMNRCL 530         540         550         560
                          FEQTPLAEPF  VGFNVNTVRG  SQFFYQHGDG  YAVTESWTKD

570
                          LSLSVLIHPI  PLNEED
```

In some embodiments, the bisabolene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of bisabolene synthase, presumably through binding to $Mg^{2+}$.

In some embodiments, the farnesene synthase, or a homologous enzyme thereof, has an amino acid sequence having at least 70% identity to the amino acid sequence of *Zea mays* farnesene synthase which is as follows:

```
                                                   (SEQ ID NO: 14)
                                   10          20          30          40
                          MDATAFHPSL  WGDFFVKYKP  PTAPKRGHMT  ERAELLKEEV 50          60          70          80
                          RKTLKAAANQ  ITNALDLIIT  LORLGLDHHY  ENEISELLRF 90         100         110         120
                          VYSSSDYDDK  DLYVVSLRFY  LLRKHGHCVS  SDVFTSFKDE 130         140         150         160
                          EGNFVVDDTK  CLLSLYNAAY  VRTHGEKVLD  EAITFTRRQL 170         180         190         200
                          EASLLDPLEP  ALADEVHLTL  QTPLFRRLRI  LEAINYIPIY 210         220         230         240
                          GKEAGRNEAI  LELAKLNFNL  AQLIYCEELK  EVTLWWKQLN 250         260         270         280
                          VETNLSFIRD  RIVECHFWMT  GACCEPQYSL  SRVIATKMTA 290         300         310         320
                          LITVLDDMMD  TYSTTEEAML  LAEAIYRWEE  NAAELLPRYM 330         340         350         360
                          KDFYLYLLKT  IDSCGDELGP  NRSFRTFYLK  EMLKVLVRGS 370         380         390         400
                          SQEIKWRNEN  YVPKTISEHL  EHSGPTVGAF  QVACSSFVGM 410         420         430         440
                          GDSITKESFE  WLLTYPELAK  SLMNISRLLN  DTASTKREQN 450         460         470         480
                          AGQHVSTVQC  YMLKHGTTMD  EACEKIKELT  EDSWKDMMEL 490         500         510         520
                          YLTPTEHPKL  IAQTIVDFAR  TADYMYKETD  GFTFSHTIKD

530
                          MIAKLFVDPI  SLF
```

In some embodiments, the farnesene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of farnesene synthase, presumably through binding to $Mg^{2+}$.

In some embodiments, the cadinene synthase, or a homologous enzyme thereof, has an amino acid sequence having at least 70% identity to the amino acid sequence of *Ocimum basilicum* cadinene synthase which is as follows:

```
                                                   (SEQ ID NO: 15)
                                   10          20          30          40
                          MDVSILRDVR  PPVTSYAPNI  WADTFSNISL  DEEVQKKYAE 50          60          70          80
                          TIEALKQVVR  GMLMAAATPI  KQMIFIDTLE  RLGLAYHFET 90         100         110         120
                          EIEHKLQKIY  DDNVCGDDCD  LFTTALRFRL  LROHRHHVSC 130         140         150         160
                          DVFDKFLYEE  GKFKGDAEGL  LSLYEASHVR  FHNEKILEEA 170         180         190         200
                          ERFTROELSC  WIKLQSPLKD  KVKRALERPL  HREVPILYAR 210         220         230         240
                          HFISIYEKDE  SMDEHLLKLA  KFNFNFLQNL  YKKELYDLSR 250         260         270         280
                          WWNKFDLKTK  LPYIRDRLAE  AYLWGVGYHF  EPQYSVRKG 290         300         310         320
                          VVLSIKIIGI  LDDTYDNYAT  VNEAQLFTEI  LDRWSMDEID 330         340         350         360
                          RLPDYMKIVL  HFVMSAYEEY  ERDAKIVYGK  KFASPYFKET 370         380         390         400
                          IQQLARGYNQ  ELKWVMEKQM  PPFKDYLKNS  EITSCIYIMF 410         420         430         440
                          ASIIPGLKSF  TOEAIDWIKN  EPNFAVKAGL  IGRYWDDIGS 450         460         470         480
                          HKRESKGGEM  LTVMDCYMKQ  YSVSIQETIS  EFAKAVEDSW 490         500         510         520
                          KEVNEGWVYT  ISMSKEITVQ  FLNYSRMCDA  SYNRNNGDGY 530         540
                          TDPSFAKSNI  TALFVDPIII
```

In some embodiments, the cadinene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of cadinene synthase, presumably through binding to $Mg^{2+}$.

In some embodiments, the aristolochene synthase, or a homologous enzyme thereof, has an amino acid sequence having at least 70% identity to the amino acid sequence of *Penicillium roqueforti* aristolochene synthase which is as follows:

```
                                            (SEQ ID NO: 16)
         10         20         30         40
   MATSTETISS LAQPFVHLEN PINSPLVKET IRPRNDTTIT 50         60         70         80
   PPPTQWSYLC HPRVKEVQDE VDGYFLENWK FPSFKAVRTF 90        100        110        120
   LDAKFSEVTC LYFPLALDDR IHFACRLLTV LFLIDDVLEH 130        140        150        160
   MSFADGEAYN NRLIPISRGD VLPDRTKPEE FILYDLWESM 170        180        190        200
   RAHDAELANE VLEPTFVFMR AQTDRARLSI HELGHYLEYR 210        220        230        240
   EKDVGKALLS ALMRFSMGLR LSADELQDMK ALEANCAKQL 250        260        270        280
   SVVNDIYSYD KEEEASRTGH KEGAFLCSAV KVLAEESKLG 290        300        310        320
   IPATKRVLWS MTREWETVHD EIVAEKIASP DGCSEAAKAY 330        340
   MKGLEYQMSG NEQWSKTTRR YN
```

In some embodiments, the aristolochene synthase comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of aristolochene synthase, presumably through binding to $Mg^{2+}$.

In some embodiments, any of the synthase described herein comprises the amino acid sequence Asp-Asp-Xaa-Xaa-Asp (DDXXD) (SEQ ID NO:17), or Asp-Asp-Xaa-Xaa-Glu (DDXXE) (SEQ ID NO:18), which is important for the catalytic activity of the synthase, presumably through binding to $Mg^{2+}$.

In some embodiments, the 1,8-cineole 2-endo-monooxygenase, or a homologous enzyme thereof, has an amino acid sequence having at least 70% identity to the amino acid sequence of *Citrobacter braakii* 1,8-cineole 2-endo-monooxygenase which is as follows:

```
                                            (SEQ ID NO: 19)
         10         20         30         40
   MTATVASTSL FTTADHYHTP LGPDGTPHAF FEALRDEAET 50         60         70         80
   TPIGWSEAYG GHWVVAGYKE IQAVIQNTKA FSNKGVTFPR 90        100        110        120
   YETGEFELMM AGQDDPVHKK YRQLVAKPFS PEATDLFTEQ 130        140        150        160
   LRQSTNDLID ARIELGEGDA ATWLANEIPA RLTAILLGLP 170        180        190        200
   PEDGDTYRRW VWAITHVENP EEGAEIFAEL VAHARTLIAE 210        220        230        240
   RRTNPGNDIM SRVIMSKIDG ESLSEDDLIG FFTILLLGGI 250        260        270        280
   DNTARFLSSV FWRLAWDIEL RRRLIAHPEL IPNAVDELLR 290        300        310        320
   FYGPAMVGRL VTQEVTVGDI TMKPGQTAML WFPIASRDRS 330        340        350        360
   AFDSPDNIVI ERTPNRHLSL GHGIHRCLGA HLIRVEARVA 370        380        390        400
   ITEFLKRIPE FSLDPNKECE WLMGQVAGML HVPIIFPKGK

RLSE
```

In some embodiments, the 1,8-cineole 2-endo-monooxygenase, or homolog thereof, comprises FXXGXRXCXG (SEQ ID NO:21), or CXG, motif and/or EXXR motif.

In some embodiments, the epi-isozizaene 5-monooxygenase, or a homologous enzyme thereof, has an amino acid sequence having at least 70% identity to the amino acid sequence of *Streptomyces coelicolor* epi-isozizaene 5-monooxygenase which is as follows:

```
                                            (SEQ ID NO: 20)
         10         20         30         40
   MTVESVNPET RAPAAPGAPE LREPPVAGGG VPLLGHGWRL 50         60         70         80
   ARDPLAFMSQ LRDHGDVVRI KLGPKTVYAV TNPELTGALA 90        100        110        120
   LNPDYHIAGP LWESLEGLLG KEGVATANGP LHRRORRTIQ 130        140        150        160
   PAFRLDAIPA YGPIMEEEAH ALTERWQPGK TVDATSESFR 170        180        190        200
   VAVRVAARCL LRGQYMDERA ERLCVALATV FRGMYRRMVV 210        220        230        240
   PLGPLYRLPL PANRRFNDAL ADLHLLVDEI IAERRASGOK 250        260        270        280
   PDDLLTALLE AKDDNGDPIG EQEIHDQVVA ILTPGSETIA 290        300        310        320
   STIMWLLQAL ADHPEHADRI RDEVEAVTGG RPVAFEDVRK 330        340        350        360
   LRHTGNVIVE AMRLRPAVWV LTRRAVAESE LGGYRIPAGA 370        380        390        400
   DIIYSPYAIQ RDPKSYDDNL EFDPDRWLPE RAANVPKYAM 410        420        430        440
   KPFSAGKRKC PSDHFSMAQL TLITAALATK YRFEQVAGSN 450        460
   DAVRVGITLR PHDLLVRPVA R
```

In some embodiments, the epi-isozizaene 5-monooxygenase, or homolog thereof, comprises FXXGXRXCXG (SEQ ID NO:21), or CXG, motif and/or EXXR motif.

Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding one or more enzymes described herein. The gene(s) encoding the enzyme(s) may be heterologous to the host cell or the gene may be native to the host cell but is operatively linked to a heterologous promoter and one or more control regions which result in a higher expression of the gene in the host cell.

The enzyme can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

Any prokaryotic or eukaryotic host cell may be used in the present method so long as it remains viable after being transformed with a sequence of nucleic acids. Generally, although not necessarily, the host cell is a yeast or a bacterium. In some embodiments, the host cell is a Gram negative bacterium. In some embodiments, the host cell is of the phylum Proteobactera. In some embodiments, the host cell is of the class Gammaproteobacteria. In some embodiments, the host cell is of the order Enterobacteriales. In some embodiments, the host cell is of the family Enterobacteriaceae. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus* taxonomical classes. In some embodiments, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway. Suitable eukaryotic cells include, but are not limited to, fungal, insect or mammalian cells. Suitable fungal cells are yeast cells, such as yeast cells of the *Saccharomyces* genus.

The genetically modified host cell can be any microbe capable of production of the modified terpenoid in accordance with the methods of the invention.

In some embodiments, the host cell is a yeast. Yeast host cells suitable for the invention include, but are not limited to, *Yarrowia, Candida, Bebaromyces, Saccharomyces, Schizosaccharomyces* and *Pichia* cells. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In one embodiment, *Candida tropicalis* is the host cell. In some embodiments, the yeast host cell is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast host cell is an oleaginous yeast. In some embodiments, the oleaginous yeast is a *Rhodosporidium* species. In some embodiments, the *Rhodosporidium* species is *Rhodosporidium toruloides*.

In some embodiments the host cell is a bacteria. Bacterial host cells suitable for the invention include, but are not limited to, *Escherichia, Corynebacterium, Pseudomonas, Streptomyces,* and *Bacillus*. In some embodiments, the *Escherichia* cell is an *E. coli, E. albertii, E. fergusonii, E. hermanii, E. marmotae,* or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtherias, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum,* or *Corynebacterium uropygiale*. In some embodiments, the *Pseudomonas* cell is a *P. putida, P. aeruginosa, P. chloro-raphis, P. fluorescens, P. pertucinogena, P. stutzeri, P. syringae, P. cremoricolorata, P. entomophila, P. fulva, P. monteilii, P. mosselii, P. oryzihabitans, P. parafluva,* or *P. plecoglossicida*. In some embodiments, the *Streptomyces* cell is a *S. coelicolor, S. lividans, S. venezuelae, S. ambofaciens, S. avermitilis, S. albus,* or *S. scabies*. In some embodiments, the *Bacillus* cell is a *B. subtilis, B. megaterium, B. licheniformis, B. anthracis, B. amyloliquefaciens,* or *B. pumilus*.

REFERENCES CITED (WHICH ARE ALL EACH INCORPORATED HEREIN BY REFERENCE)

(1) Aharoni, A.; Jongsma, M. A.; Bouwmeester, H. J. Volatile Science? Metabolic Engineering of Terpenoids in Plants. *Trends Plant Sci.* 2005, 10 (12), 594-602.

(2) Chang, M. C. Y.; Eachus, R. A.; Trieu, W.; Ro, D.-K.; Keasling, J. D. Engineering *Escherichia Coli* for Production of Functionalized Terpenoids Using Plant P450s. *Nat. Chem. Biol.* 2007, 3,274.

(3) Renault, H.; Bassard, J.-E.; Hamberger, B.; Werck-Reichhart, D. Cytochrome P450-Mediated Metabolic Engineering: Current Progress and Future Challenges. *Curr. Opin. Plant Biol.* 2014, 19, 27-34.

(4) van Beilen, J. B.; Holtackers, R.; Lüscher, D.; Bauer, U.; Witholt, B.; Duetz, W. A. Biocatalytic Production of Perillyl Alcohol from Limonene by Using a Novel *Mycobacterium* Sp. Cytochrome P450 Alkane Hydroxylase Expressed in *Pseudomonas Putida*. *Appl. Environ. Microbiol.* 2005, 71 (4), 1737 LP-1744.

(5) Alonso-Gutierrez, J.; Chan, R.; Batth, T. S.; Adams, P. D.; Keasling, J. D.; Petzold, C. J.; Lee, T. S. Metabolic Engineering of *Escherichia Coli* for Limonene and Perillyl Alcohol Production. *Metab. Eng.* 2013, 19, 33-41.

(6) Conrado, R. J.; Varner, J. D.; DeLisa, M. P. Engineering the Spatial Organization of Metabolic Enzymes: Mimicking Nature's Synergy. *Curr. Opin. Biotechnol.* 2008, 19 (5), 492-499.

(7) Meynial Salles, I.; Forchhammer, N.; Croux, C.; Girbal, L.; Soucaille, P. Evolution of a *Saccharomyces Cerevisiae* Metabolic Pathway in *Escherichia Coli*. *Metab. Eng.* 2007, 9 (2), 152-159.

(8) Kourtz, L.; Dillon, K.; Daughtry, S.; Madison, L. L.; Peoples, O.; Snell, K. D. A Novel Thiolase-Reductase Gene Fusion Promotes the Production of Polyhydroxybutyrate in *Arabidopsis*. *Plant Biotechnol. J.* 2005, 3 (4), 435-447.

(9) Dueber, J. E.; Wu, G. C.; Malmirchegini, G. R.; Moon, T. S.; Petzold, C. J.; Ullal, A. V; Prather, K. L. J.; Keasling, J. D. Synthetic Protein Scaffolds Provide Modular Control over Metabolic Flux. *Nat. Biotechnol.* 2009, 27 (8), 753-759.

(10) Avalos, J. L.; Fink, G. R.; Stephanopoulos, G. Compartmentalization of Metabolic Pathways in Yeast Mitochondria Improves the Production of Branched-Chain Alcohols. *Nat. Biotechnol.* 2013, 31, 335.

(11) Yu, K.; Liu, C.; Kim, B.-G.; Lee, D.-Y. Synthetic Fusion Protein Design and Applications. *Biotechnol. Adv.* 2015, 33 (1), 155-164.

(12) Sarria, S.; Wong, B.; Martin, H. G.; Keasling, J. D.; Peralta-Yahya, P. Microbial Synthesis of Pinene. *ACS Synth. Biol.* 2014, 3 (7), 466-475.

(13) Gao, X.; Gao, F.; Liu, D.; Zhang, H.; Nie, X.; Yang, C. Engineering the Methylerythritol Phosphate Pathway in Cyanobacteria for Photosynthetic Isoprene Production from $CO_2$. *Energy Environ. Sci.* 2016, 9 (4), 1400-1411.

(14) Zuo, R.; Zhang, Y.; Jiang, C.; Hackett, J. C.; Loria, R.; Bruner, S. D.; Ding, Y. Engineered P450 Biocatalysts Show Improved Activity and Regio-Promiscuity in Aromatic Nitration. *Sci. Rep.* 2017, 7 (1), 842.

(15) Girvan, H. M.; Munro, A. W. Applications of Microbial Cytochrome P450 Enzymes in Biotechnology and Synthetic Biology. *Curr. Opin. Chem. Biol.* 2016, 31, 136-145.

(16) Munro, A. W.; Girvan, H. M.; Mason, A. E.; Dunford, A. J.; McLean, K. J. What Makes a P450 Tick? *Trends Biochem. Sci.* 2013, 38 (3), 140-150.

(17) Shaw, J. J.; Berbasova, T.; Sasaki, T.; Jefferson-George, K.; Spakowicz, D. J.; Dunican, B. F.; Portero, C. E.; Narváez-Trujillo, A.; Strobel, S. A. Identification of a Fungal 1,8-Cineole Synthase from *Hypoxylon* Sp. with Specificity Determinants in Common with the Plant Synthases. *J. Biol. Chem.* 2015, 290 (13), 8511-8526.

(18) Yang, X.; Li, T.; Tang, K.; Zhou, X.; Lu, M.; Ounkham, W. L.; Spain, S. M.; Frost, B. J.; Lin, H. Highly Efficient Conversion of Terpenoid Biomass to Jet-Fuel Range Cycloalkanes in a Biphasic Tandem Catalytic Process. *Green Chem.* 2017, 19 (15), 3566-3573.

(19) Bergman, A.; Siewers, V. Chapter 7—Metabolic Engineering Strategies to Convert Carbohydrates to Aviation Range Hydrocarbons; Chuck, C. J. B. T.-B. for A., Ed.; Academic Press, 2016; pp 151-190.

(20) Mendez-Perez, D.; Alonso-Gutierrez, J.; Hu, Q.; Molinas, M.; Baidoo, E. E. K.; Wang, G.; Chan, L. J. G.; Adams, P. D.; Petzold, C. J.; Keasling, J. D.; et al. Production of Jet Fuel Precursor Monoterpenoids from Engineered *Escherichia coli*. *Biotechnol. Bioeng.* 2017, 114 (8), 1703-1712.

(21) Leita, B. A.; Warden, A. C.; Burke, N.; O'Shea, M. S.; Trimm, D. Production of P-Cymene and Hydrogen from a Bio-Renewable Feedstock-1,8-Cineole (*Eucalyptus* Oil). *Green Chem.* 2010, 12 (1), 70-76.

(22) Hawkes, D. B.; Adams, G. W.; Burlingame, A. L.; Ortiz de Montellano, P. R.; De Voss, J. J. Cytochrome P450cin (CYP176A), Isolation, Expression, and Characterization. *J. Biol. Chem.* 2002, 277 (31), 27725-27732.

(23) Hawkes, D. B.; Slessor, K. E.; Bernhardt, P. V; De Voss, J. J. Cloning, Expression and Purification of Cindoxin, an Unusual Fmn-Containing Cytochrome P450 Redox Partner. *ChemBioChem* 2010, 11 (8), 1107-1114.

(24) Guo, H.; Yang, Y.; Xue, F.; Zhang, H.; Huang, T.; Liu, W.; Liu, H.; Zhang, F.; Yang, M.; Liu, C.; et al. Effect of Flexible Linker Length on the Activity of Fusion Protein 4-Coumaroyl-CoA Ligase::Stilbene Synthase. *Mol. Biosyst.* 2017, 13 (3), 598-606.

(25) Ljungcrantz, P.; Carlsson, H.; Mansson, M. O.; Buckel, P.; Mosbach, K.; Buelow, L. Construction of an Artificial Bifunctional Enzyme, .Beta.-Galactosidase/Galactose Dehydrogenase, Exhibiting Efficient Galactose Channeling. *Biochemistry* 1989, 28 (22), 8786-8792.

(26) Hoffmann, S. M.; Weissenborn, M. J.; Gricman, Ł.; Notonier, S.; Pleiss, J.; Hauer, B. The Impact of Linker Length on P450 Fusion Constructs: Activity, Stability and Coupling. *ChemCatChem* 2016, 8 (8), 1591-1597.

(27) Belsare, K. D.; Ruff, A. J.; Martinez, R.; Shivange, A. V; Mundhada, H.; Holtmann, D.; Schrader, J.; Schwaneberg, U. P-LinK: A Method for Generating Multicomponent Cytochrome P450 Fusions with Variable Linker Length. *Biotechniques* 2014, 57 (1), 13-20.

(28) Zhao, B.; Lin, X.; Lei, L.; Lamb, D. C.; Kelly, S. L.; Waterman, M. R.; Cane, D. E. Biosynthesis of the Sesquiterpene Antibiotic Albaflavenone in *Streptomyces Coelicolor* A3(2). *J. Biol. Chem.* 2008, 283 (13), 8183-8189.

(29) Liu, C.-L.; Tian, T.; Alonso-Gutierrez, J.; Garabedian, B.; Wang, S.; Baidoo, E. E. K.; Benites, V.; Chen, Y.; Petzold, C. J.; Adams, P. D.; et al. Renewable Production of High Density Jet Fuel Precursor Sesquiterpenes from *Escherichia coli*. *Biotechnol. Biofuels* 2018, 11 (1), 285.

(30) Kang, A.; George, K. W.; Wang, G.; Baidoo, E.; Keasling, J. D.; Lee, T. S. Isopentenyl Diphosphate (IPP)-Bypass Mevalonate Pathways for Isopentenol Production. *Metab. Eng.* 2016, 34, 25-35.

(31) Redding-Johanson, A. M.; Batth, T. S.; Chan, R.; Krupa, R.; Szmidt, H. L.; Adams, P. D.; Keasling, J. D.; Soon Lee, T.; Mukhopadhyay, A.; Petzold, C. J. Targeted Proteomics for Metabolic Pathway Optimization: Application to Terpene Production. *Metab. Eng.* 2011, 13 (2), 194-203.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Production of Oxidized Terpenoids Using P450 Enzymes and their Engineered Enzymes Fusions Terpenes are a large class of organic compounds, primarily produced by plants and constitute the main components of essential oils. The functionalization of terpene hydrocarbons using cytochrome P450 enzymes can derive many useful compounds that can be converted to diverse valuable products. In this study, to expand the portfolio of bioproducts from biofuel pathways, cytochrome P450 enzymes are investigated for oxidizing monoterpene (e.g. limonene, 1,8-cineole), a few oxidized terpenes are produced, including carveol, isopiperitenol, (1R)-6-hydroxycineole. Based on those oxidized terpenes, possible biosynthetic pathways are explored toward making biological-derived functionalized terpenes, such as carvolactone, a monomer of thermoplastic polyester. On the other hand, terpenes are hydrophobic and volatile compounds that limit the accessibility of P450 enzymes. To optimize the production of oxidized terpenes, an enzyme fusion strategy is developed with linking terpene synthase and P450 enzyme. In an example of producing (1R)-6-hydroxycineole, the engineered fusion shows higher efficiency from both in vitro and in vivo production results. Thus, engineering a fusion between terpene synthase and P450 presents a feasible strategy for producing oxidized terpenes, suggesting broad application during the production of terpene-based bioproducts.

Production of oxidized terpenes and derived bioproducts using P450 enzymes. The functionalization of terpene hydrocarbons using cytochrome P450 enzymes can derive many useful compounds that can be converted to diverse valuable products. See FIG. 1.

Biosynthesis of carvolactone as a monomer. Biosynthetic pathway is explored based on oxidized terpenes and carvolactone is selected as a functionalized terpene target since it is a new monomer for making thermoplastic polymer. To build the biosynthetic pathway of carvolactone, optimal enzymes (dehydrogenase/reductase) are screened and selected. See FIGS. 2A to 2D.

Figure 3:
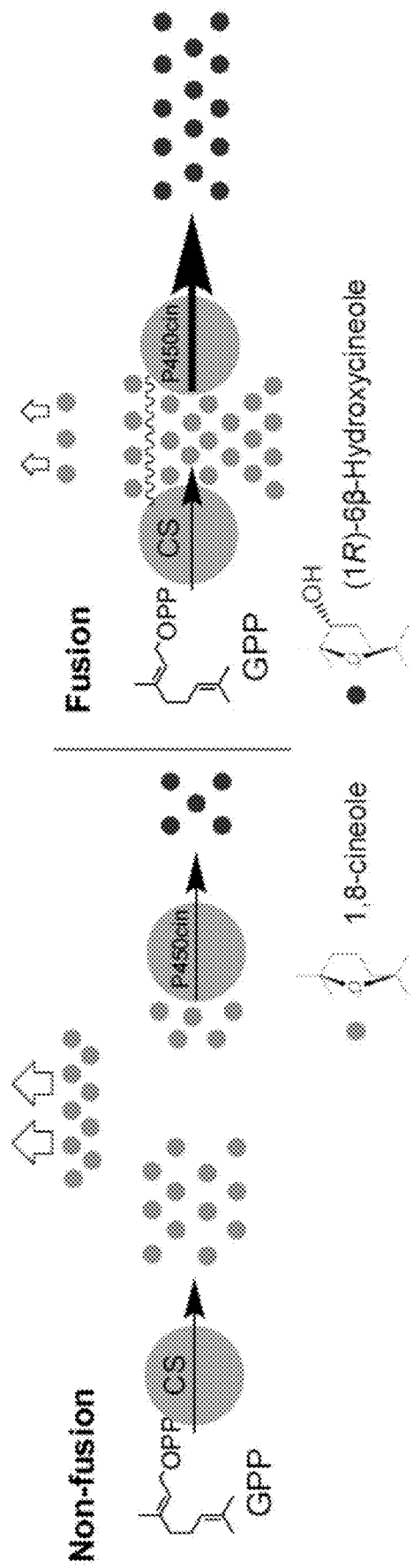
FIG. 3. A particular embodiment of the engineered fusion protein of the present invention.

Engineering fusion between terpene synthase and P450 toward efficient production of oxidized terpene. Enzyme fusions are engineered to improve substrate availability as terpenes are hydrophobic and easily lost by phase separation. See FIG. 3. Enzyme fusions of cineole synthase and P450cin with different linker lengths are engineered. Fusions show up to 5-fold increase than non-fused enzymes during the in vitro hydroxycineole production. See FIGS. 5A to 5D.

In vivo assessment of fusion enzymes toward hydroxycineole production. Fusions are engineered into 1,8-cineole overproducing strain to assess the in vivo production of hydroxycineole. Fusions increase up to 3 folds in hydroxycineole production than non-fused enzymes, a 9 amino-acid linker (G3) shows the highest production of hydroxycineole (56 mg/L). See FIGS. 6A to 6C.

Conclusions. P450 enzymes are used to oxidize terpenes and several oxidized terpenes are produced. Carvolactone is selected and produced as a new monomer using P450 enzymes and limonene synthesis pathway. An enzyme fusion strategy is developed by linking terpene synthase and P450 enzyme toward optimizing oxidized terpene production. Fusion enzymes show higher efficiency during hydroxycineole production.

Example 2

Efficient Production of Oxidized Terpenoids Via Engineering Fusion Proteins of Terpene Synthase and P450

The functionalization of terpene hydrocarbons using cytochrome P450 enzymes is a versatile route to produce useful derivatives that can be further converted to value-added products. As terpenes are generally hydrophobic and volatile, however, their availability as a substrate for the P450 enzymes is limited especially when a solvent overlay is used to trap terpenes and prevent evaporation during the microbial terpene biosynthesis. In this study, an enzyme fusion strategy is developed by directly linking terpene synthase and P450 enzyme together to improve the accessibility of terpene molecules as a substrate for P450 enzymes. Using the hydroxylation of a monoterpene 1,8-cineole as a model system, a series of fusion proteins between 1,8-cineole synthase and $P450_{cin}$ (CYP176A1) are engineered with different lengths of peptide linkers to investigate the hydroxylation of 1,8-cineole. Results show that the fusion enzyme increases 5.4 and 3.1 folds in hydroxycineole production than non-fused individual enzymes at the in vitro and in vivo conditions, respectively. The enzyme fusion strategy is also applied to the oxidation of a sesquiterpene epi-isozizaene, in which a 90-fold increase is observed by the fusion in albaflavenol production. Developing fusion enzymes for terpene synthase and P450 presents an efficient strategy toward oxidation of hydrophobic terpene compounds and this strategy will be widely applicable for the functionalization of hydrophobic biosynthetic intermediates.

Given that the considerable loss of terpene molecules is a critical limitation for the subsequent P450 reaction during the microbial production[5], engineering a fusion protein by linking terpene synthase and P450 to form a chimeric protein could improve the proximity of P450 and the terpene substrate, which in turn would improve the substrate availability for P450.

Figure 4:
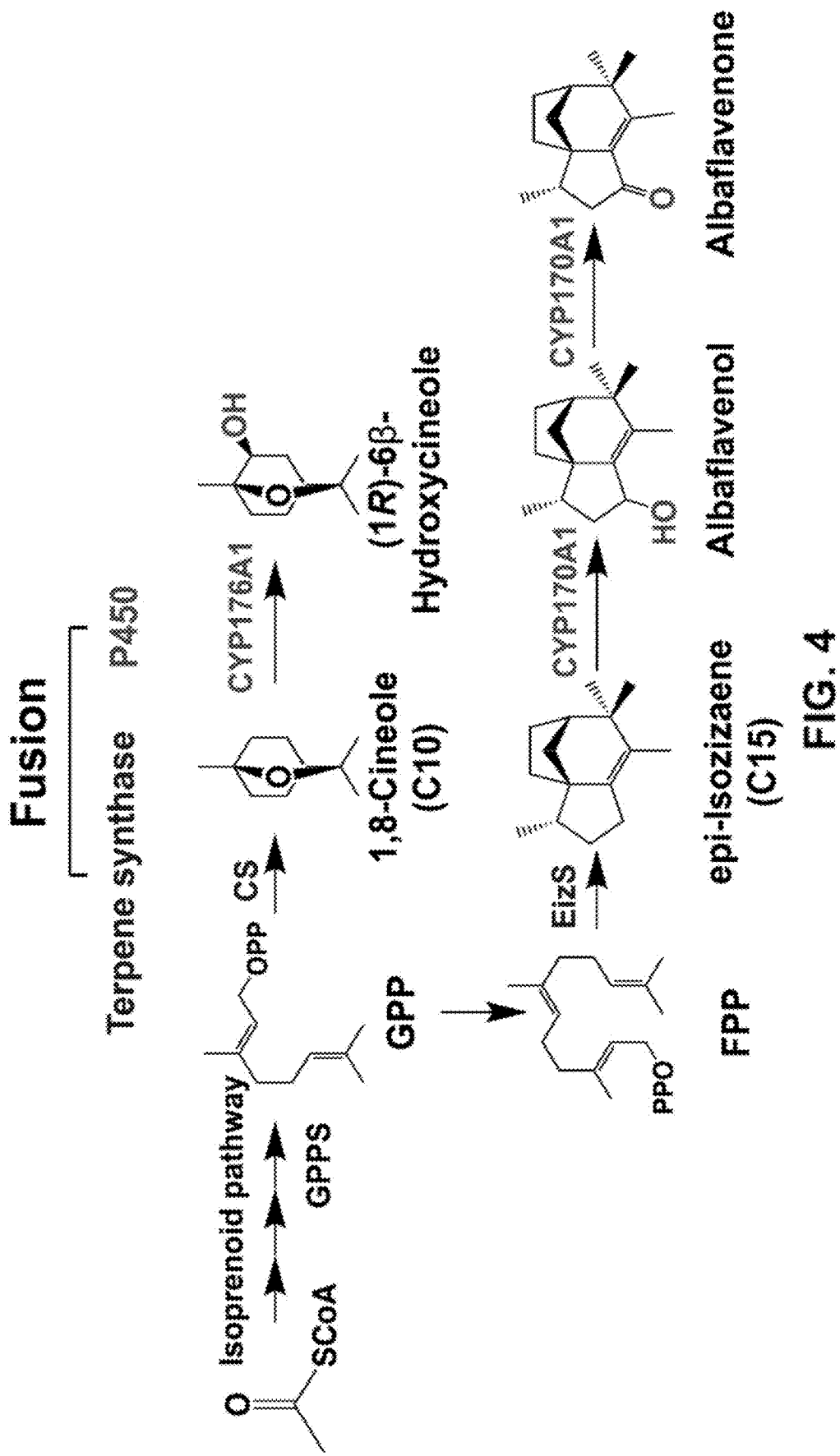
FIG. 4. Engineering enzyme fusions by linking terpene synthase and P450 enzyme for the production of oxidized terpenes. GPP, geranyl pyrophosphate; FPP, farnesyl pyrophosphate; CS, 1,8-cineole synthase; EizS, epi-isozizaene synthase; GPPS, geranyl pyrophosphate synthase.

In this study, hydroxylation of monoterpene 1,8 cineole is selected as a model system for this approach of terpene synthase-P450 fusion (FIG. 4). A series of fusion proteins are engineered between 1,8-cineole synthase and $P450_{cin}$ (CYP176A1) with different lengths of peptide linkers to investigate the hydroxylation of 1,8-cineole. The production of hydroxycineole from both in vitro and in vivo conditions is compared between the fusion and non-fused enzymes. This enzyme fusion strategy is also applied to the oxidization of a sesquiterpene epi-isozizaene (FIG. 4), and results from both examples showed the fused enzymes are more efficient than non-fused enzymes during the production of oxidized terpenes. This result suggests a feasible strategy for the efficient production of oxidized terpenes as well as possible applications for the production of terpene-based bioproducts.

Results and Discussion

While engineering of fusion proteins shows an easy approach for desirable enzymatic characteristics, it is still challenging to achieve the optimal activities, for example, it is difficult to precisely control the distance of enzymes in a fusion protein, the folding of a larger multidomain protein may be inefficient, etc.

Engineering Fusion Enzymes of 1,8-Cineole Synthase and $P450_{cin}$ 1,8-Cineole, or eucalyptol, is a monoterpene (C10) that naturally found in essential oils[17]. 1,8-Cineole is also a potential precursor for high energy density molecules used as jet fuels[18,19], and therefore E. coli is engineered to overproduce 1,8-cineole using the mevalonate (MVA) pathway[20]. Hydroxylation of 1,8-cineole introduces a functional group, which decorates this compound with possibilities to further derived valuable products, such as p-cymene[21]. $P450_{cin}$ (CYP176A1) from Citrobacter braakii is found showing a specific activity for 1,8-cineole hydroxylation to (1R)-6β-hydroxycineole (or hydroxycineole)[22,23].

Figure 5A:
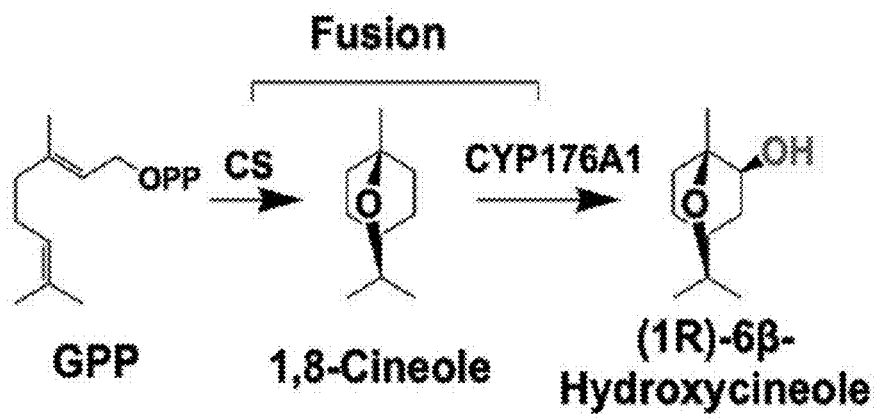
FIG. 5A. In vitro production of hydroxycineole. In vitro two-step reaction from GPP.
Figure 5B:
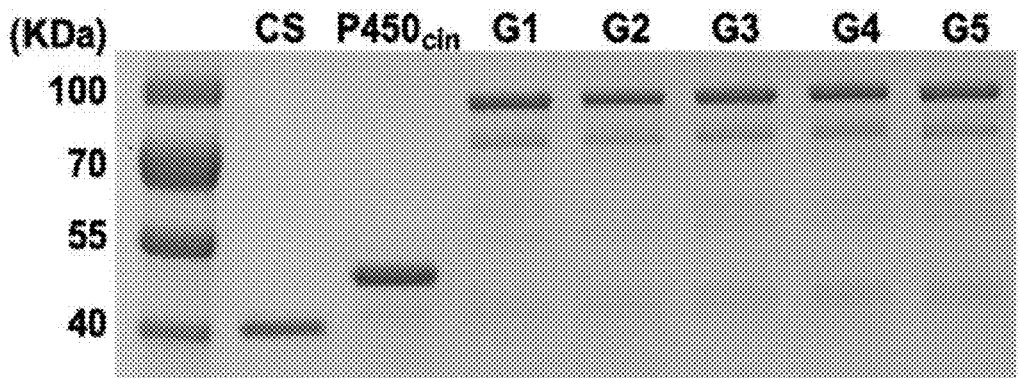
FIG. 5B. In vitro production of hydroxycineole. SDS-PAGE gel of purified non-fusion and fusions for CS and $P450_{cin}$. Fusions of 1,8-cineole synthase (CS) and $P450_{cin}$ are engineered with 1 to 5 repeats of the Gly-Ser-Gly (GSG) peptide linker. Size of purified proteins: CS, 40.71 KDa; $P450_{cin}$ (CinA), 48.25 KDa; G1, 86.16 KDa; G2, 86.37 KDa; G3, 86.57 KDa; G4, 86.77 KDa; G5, 86.97 KDa.

To investigate the hydroxylation of 1,8-cineole as a model system of the fusion of terpene synthase and P450, fusion proteins are prepared between 1,8-cineole synthase (CS) and $P450_{cin}$ using a widely studied flexible peptide linker (Gly-Ser-Gly)$_n$[24]. By adjusting the repeat number (n) of the Gly-Ser-Gly (GSG) linker, five CS-$P450_{cin}$ fusion proteins have been engineered with different linker lengths (n=1-5) and named as G1 to G5 according to their GSG linker repeats (FIG. 5A, FIG. 5B).

In Vitro Production of Hydroxycineole with CS-$P450_{cin}$ Fusions from GPP

Figure 5C:
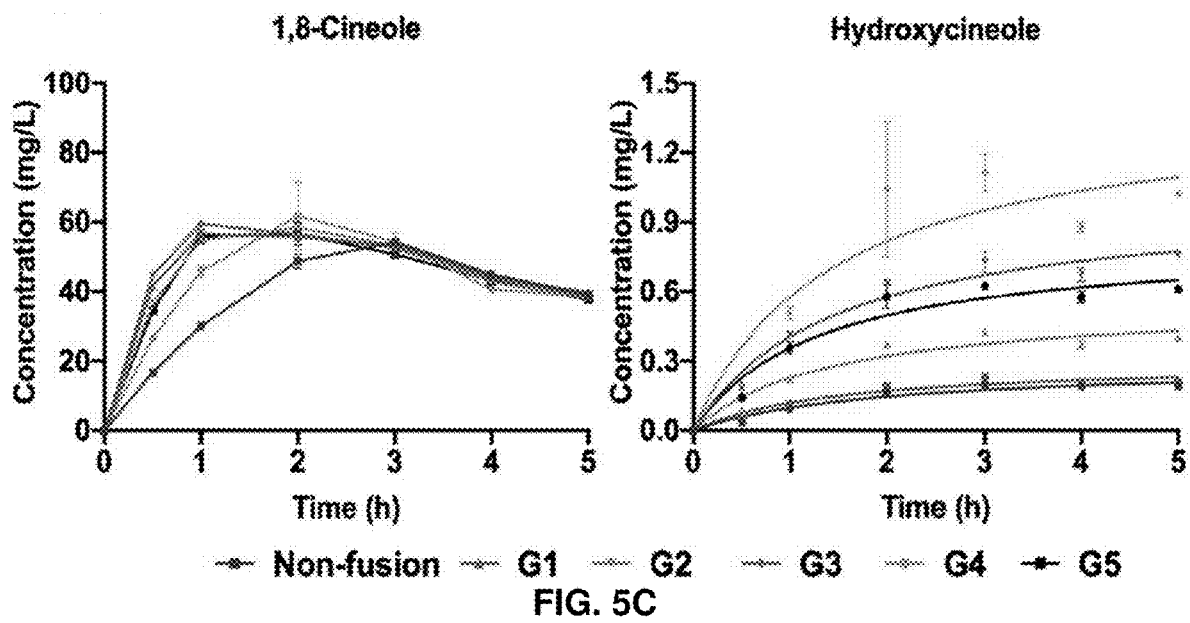
FIG. 5C. In vitro production of hydroxycineole. In vitro time-course production of hydroxycineole and cineole with purified proteins. Error bars indicate one standard deviation (n=3).

To investigate the hydroxylation of 1,8-cineole by various engineered CS-$P450_{cin}$ fusions, equal moles of purified proteins are used for in vitro production of hydroxycineole from GPP (FIGS. 5A to 5D). In a 5-hour reaction, all CS-$P450_{cin}$ fusions show higher production of hydroxycineole than non-fuse individual CS and $P450_{cin}$ n except for G1, which does not show a significant difference from the non-fusion control (FIG. 5C). The highest production of hydroxycineole is observed from G4 fusion with a 4-repeat of GSG linker, which shows a 5.4-fold increase over non-fused CS and $P450_{cin}$ after 5 hours (FIG. 5C). The highest hydroxycineole production rate in G4 is reached after 2 hours at 0.051 µM/min, which is 6.4-fold faster than that of the non-fusion enzymes (0.008 µM/min). The overall hydroxylation ratio of G4 is 2.3% after 5 hours, which is 5.4-fold higher than that of the non-fusion enzymes (0.4%)

Figure 5D:
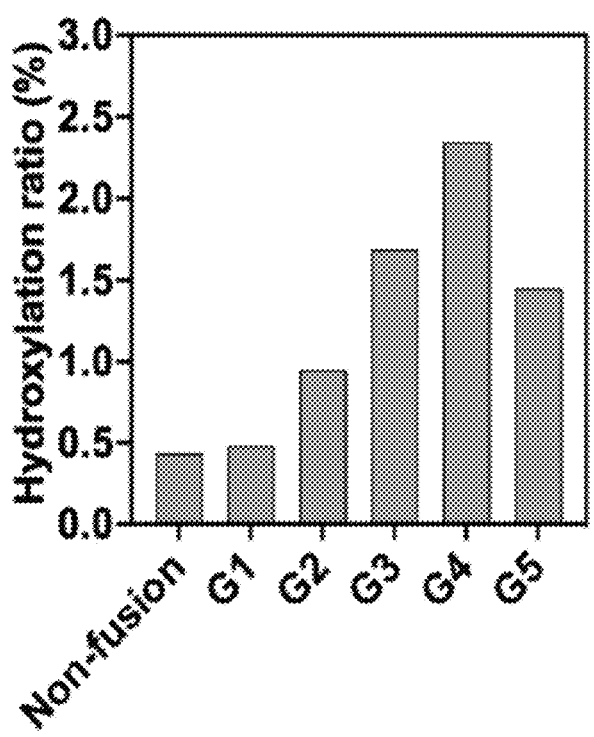
FIG. 5D. In vitro production of hydroxycineole. Hydroxylation ratio of in vitro reaction after 5 hours. Hydroxylation ratio is the molar ratio of hydroxycineole out of the total generated terpenes (1,8-cineole and hydroxycineole).

(FIG. 5D). It is also noticed that all 5 fusion enzymes showed up to a 2.7-fold increase of 1,8-cineole over the non-fused enzymes during the first 3 hours (FIG. 5C), indicating more terpene substrate was available in the reaction with CS-P450$_{cin}$ fusions.

According to the in vitro production results, the engineered CS-P450$_{cin}$ fusions show higher efficiencies than non-fused CS and P450$_{cin}$ during hydroxycineole production. The improved hydroxylation from fusions can be attributed to the proximity of P450$_{cin}$ to its hydrophobic substrate 1,8-cineole, which shows the feasibility of linking a P450 enzyme to a biosynthetic pathway enzyme, particularly when terpenes are used as substrates for P450 reactions. Additionally, the increased 1,8-cineole production in the first 3 hours might result from the local hydrophobic environment created by the fusion enzyme and thus facilitated the 1,8-cineole accumulation. It can also suggest that terpene synthase activity is increased in the fusion enzymes as previously reported in a fusion of *E. coli* beta-galactosidase (LacZ) and the dimeric galactose dehydrogenase (GalDH) from *Pseudomonas fluorescens* which shows improved enzyme activities when they are linked each other[25].

In Vivo Assessment of CS-P450$_{cin}$ Fusions for Hydroxycineole Production from Glucose The CS-P450$_{cin}$ fusions are further engineered into the 1,8-cineole overproducing *E. coli* strain[20] to assess hydroxycineole production under the in vivo conditions. Informed from the previous report[20], a 2-plasmid system is used for hydroxycineole production by inserting P450$_{cin}$ (CinA) and the reductase (CinC) at the downstream of CS on the plasmid JBEI-15065 (Table 2). For the non-fused expression of CS and P450$_{cin}$, an RBS sequence (5'-TT-TAAGAAGGAGATATACC-3') is used for individual expression of both CS and P450$_{cin}$ (Table 2). For the CS-P450$_{cin}$ fusions, the same RBS is used for the entire fused protein sequence. As solvent overlay is usually used to enrich terpene molecules and prevent evaporation of the product during fermentation, an overly is used to evaluate the performance of fusion enzymes at the in vivo conditions. While dodecane is used as the overlay for 1,8-cineole production previously[20], it has a similar molecular weight to hydroxycineole (MW=170), as well as a very close retention time in GC analysis. Therefore, nonane, instead of dodecane, is used as the overlay to obtain a better signal of hydroxycineole on GC.

TABLE 2

Strains and plasmids used in this study.

| | Description | Reference |
|---|---|---|
| Strains | | |
| CS | *E. coli* BL21 (DE3) with pSKB3-CS | This study |
| CinA | *E. coli* BL21 (DE3) with pSKB3-CinA | This study |
| CinC | *E. coli* BL21 (DE3) with pSKB3-CinC | This study |
| G1 | *E. coli* BL21 (DE3) with pSKB3-CS-G1-CinA | This study |
| G2 | *E. coli* BL21 (DE3) with pSKB3-CS-G2-CinA | This study |
| G3 | *E. coli* BL21 (DE3) with pSKB3-CS-G3-CinA | This study |
| G4 | *E. coli* BL21 (DE3) with pSKB3-CS-G4-CinA | This study |
| G5 | *E. coli* BL21 (DE3) with pSKB3-CS-G5-CinA | This study |
| Fpr | *E. coli* BL21 (DE3) with pSKB3-Fpr | This study |
| 2pCin_Non-fusion | *E. coli* DH1 with JBEI-3122 + pTrc99a-trGPPS-CS-RBS-CinAC | This study |
| 2pCin_G1 | *E. coli* DH1 with JBEI-3122 + pTrc99a-trGPPS-CS-G1-CinAC | This study |
| 2pCin_G2 | *E. coli* DH1 with JBEI-3122 + pTrc99a-trGPPS-CS-G2-CinAC | This study |
| 2pCin_G3 | *E. coli* DH1 with JBEI-3122 + pTrc99a-trGPPS-CS-G3-CinAC | This study |
| 2pCin_G4 | *E. coli* DH1 with JBEI-3122 + pTrc99a-trGPPS-CS-G4-CinAC | This study |
| 2pCin_G5 | *E. coli* DH1 with JBEI-3122 + pTrc99a-trGPPS-CS-G5-CinAC | This study |
| 2pCin_G3 reverse | *E. coli* DH1 with JBEI-3122 + pTrc99a-trGPPS-CinA-G3-CS-CinC | This study |
| 2pEiz | *E. coli* DH1 with JBEI-2704 + JBEI-15862 | This study |
| 2pEizSC_Non-fusion | *E. coli* DH1 with JBEI-2704 + pTrc99a-EizS-RBS-CYP170A1-CinC | This study |
| 2pEizSC_EG1 | *E. coli* DH1 with JBEI-2704 + pTrc99a-EizS-G1-CYP170A1-CinC | This study |
| 2pEizSC_EG2 | *E. coli* DH1 with JBEI-2704 + pTrc99a-EizS-G2-CYP170A1-CinC | This study |
| 2pEizSC_EG3 | *E. coli* DH1 with JBEI-2704 + pTrc99a-EizS-G3-CYP170A1-CinC | This study |
| 2pEizSC_EG4 | *E. coli* DH1 with JBEI-2704 + pTre998-EizS-G4-CYP170A1-CinC | This study |
| 2pEizSC_EG5 | *E. coli* DH1 with JBEI-2704 + pTrc99a-EizS-G5-CYP170A1-CinC | This study |
| Plasmids | | |
| pSKB3 | Modified pET-28a | 30 |
| JBEI-3122 | pBbA5c-MTSA-T1-MBI | 5 |
| JBEI-15065 | pTrc99a-GPPS-CS$_{Sr}$ | 20 |
| JBEI-2704 | pBbA5c-MevT-T1-MBIS | 31 |
| JBEI-15862 | pTrc99a-coEizS | 29 |
| | pSKB3-CS | This study |

TABLE 2-continued

Strains and plasmids used in this study.

| Description | Reference |
|---|---|
| pSKB3-CinA | This study |
| pSKB3-CinC | This study |
| pSKB3-CS-G1-CinA | This study |
| pSKB3-CS-G2-CinA | This study |
| pSKB3-CS-G3-CinA | This study |
| pSKB3-CS-G4-CinA | This study |
| pSKB3-CS-G5-CinA | This study |
| pSKB3-Fpr | This study |
| pTrc99a-trGPPS-CS-RBS-CinAC | This study |
| pTrc99a-trGPPS-CS-G1-CinAC | This study |
| pTrc99a-trGPPS-CS-G2-CinAC | This study |
| pTrc99a-trGPPS-CS-G3-CinAC | This study |
| pTrc99a-trGPPS-CS-G4-CinAC | This study |
| pTrc99a-trGPPS-CS-G5-CinAC | This study |
| pTrc99a-trGPPS-CinA-G3-CS-CinC | This study |
| pTrc99a-EizS-RBS-CYP170A1-CinC | This study |
| pTrc99a-EizS-G1-CYP170A1-CinC | This study |
| pTrc99a-EizS-G2-CYP170A1-CinC | This study |
| pTrc99a-EizS-G3-CYP170A1-CinC | This study |
| pTrc99a-EizS-G4-CYP170A1-CinC | This study |
| pTrc99a-EizS-G5-CYP170A1-CinC | This study |

Figure 6A:
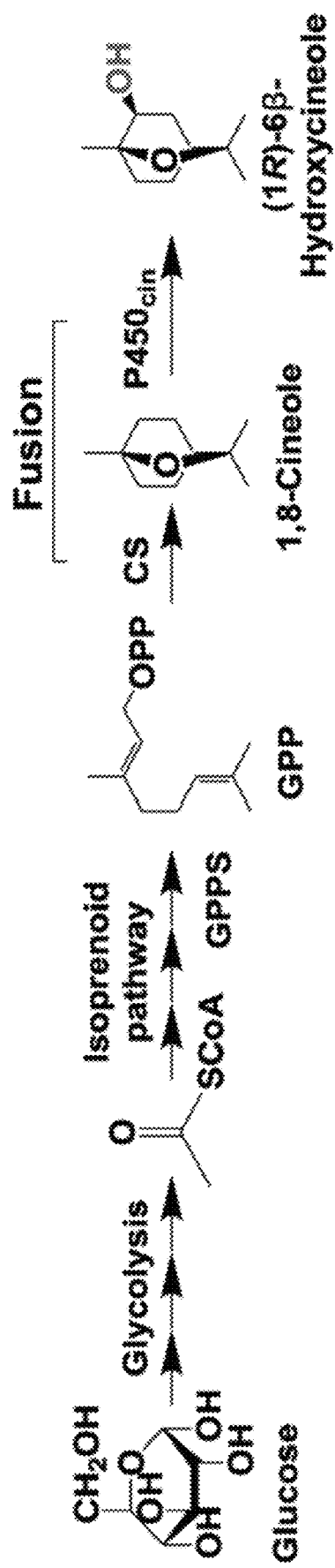
FIG. 6A. In vivo production of hydroxycineole by *E. coli* DH1 strains with engineered enzyme fusions. Metabolic pathway of hydroxycineole production from glucose using enzyme fusions of 1,8-cineole synthase (CS) and $P450_{cin}$, CS-$(GSG)_n$-$P450_{cin}$ (n=1-5).
Figure 6B:
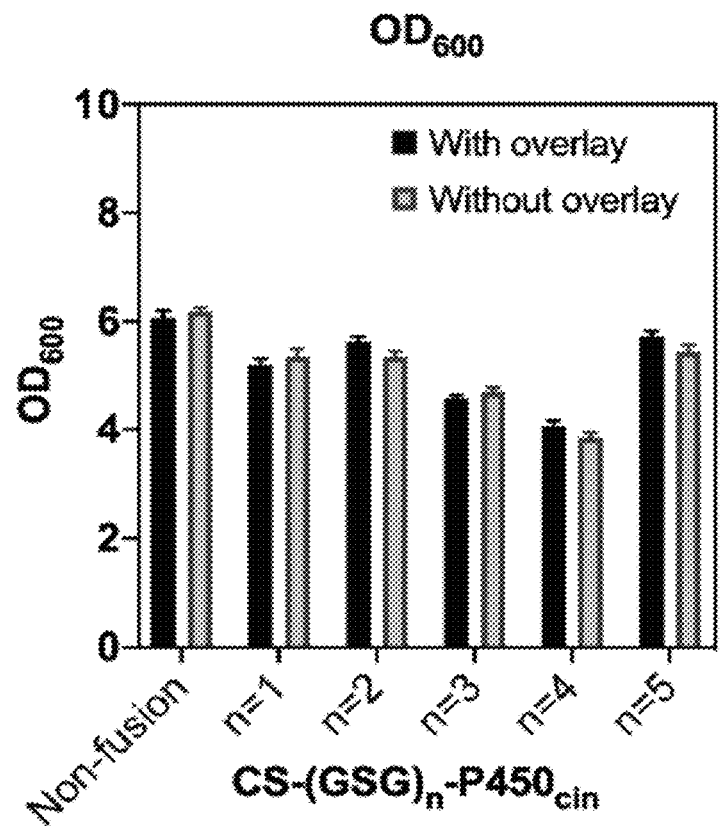
FIG. 6B. In vivo production of hydroxycineole by *E. coli* DH1 strains with engineered enzyme fusions. $OD_{600}$ of production strains after 48 hours. Error bars indicate one standard deviation (n=3).
Figure 6C:
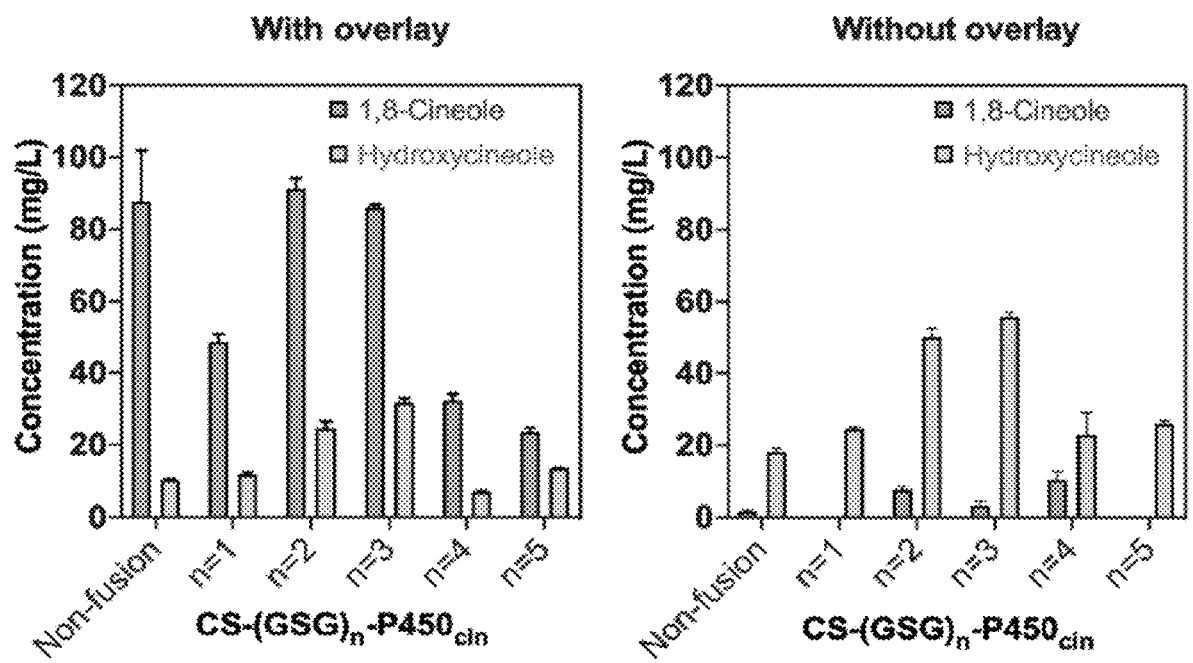
FIG. 6C. In vivo production of hydroxycineole by *E. coli* DH1 strains with engineered enzyme fusions. Production of 1,8-cineole and hydroxycineole with and without using solvent overlay. Error bars indicate one standard deviation (n=3).
Figure 7A:
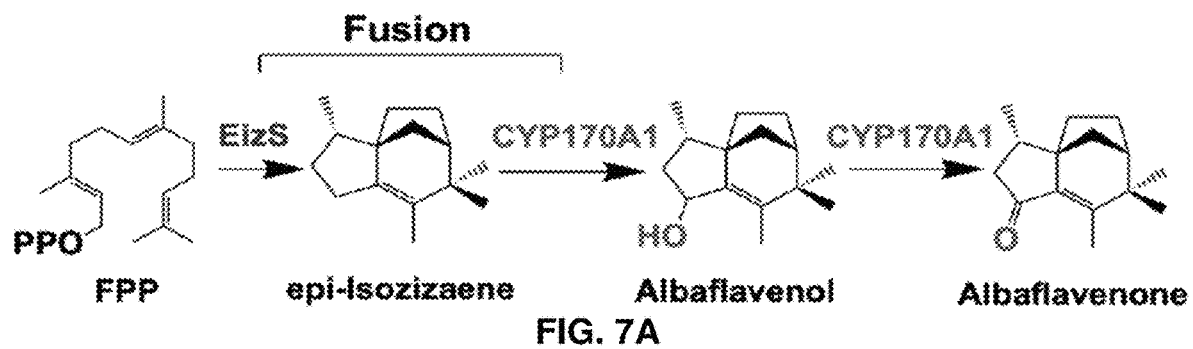
FIG. 7A. Production of oxidized epi-isozizaene with engineered enzyme fusions in *E. coli* DH1. Metabolic pathway of oxidized epi-isozizaene production from glucose using enzyme fusions of epi-isozizaene synthase (EizS) and CYP170A1, EizS-$(GSG)_n$-CYP170A1 (n=1-5), FPP, farnesyl pyrophosphate.
Figure 7B:
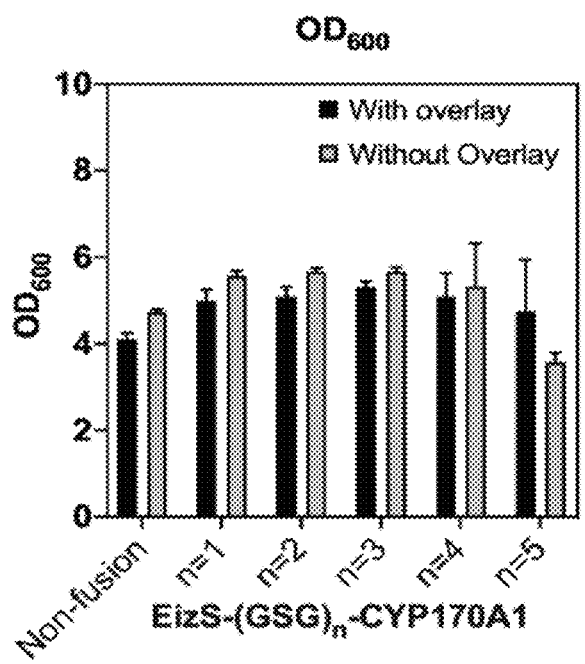
FIG. 7B. Production of oxidized epi-isozizaene with engineered enzyme fusions in *E. coli* DH1. $OD_{600}$ of production strains after 72 hours. Error bars indicate one standard deviation (n=3).
Figure 7C:
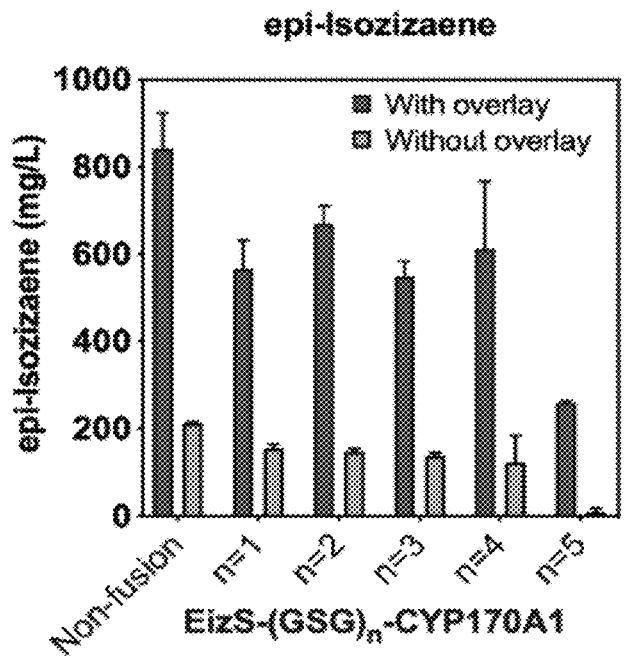
FIG. 7C. Production of oxidized epi-isozizaene with engineered enzyme fusions in *E. coli* DH1. Production of epi-isozizaene with and without using solvent overlay. Error bars indicate one standard deviation (n=3).
Figure 7D:
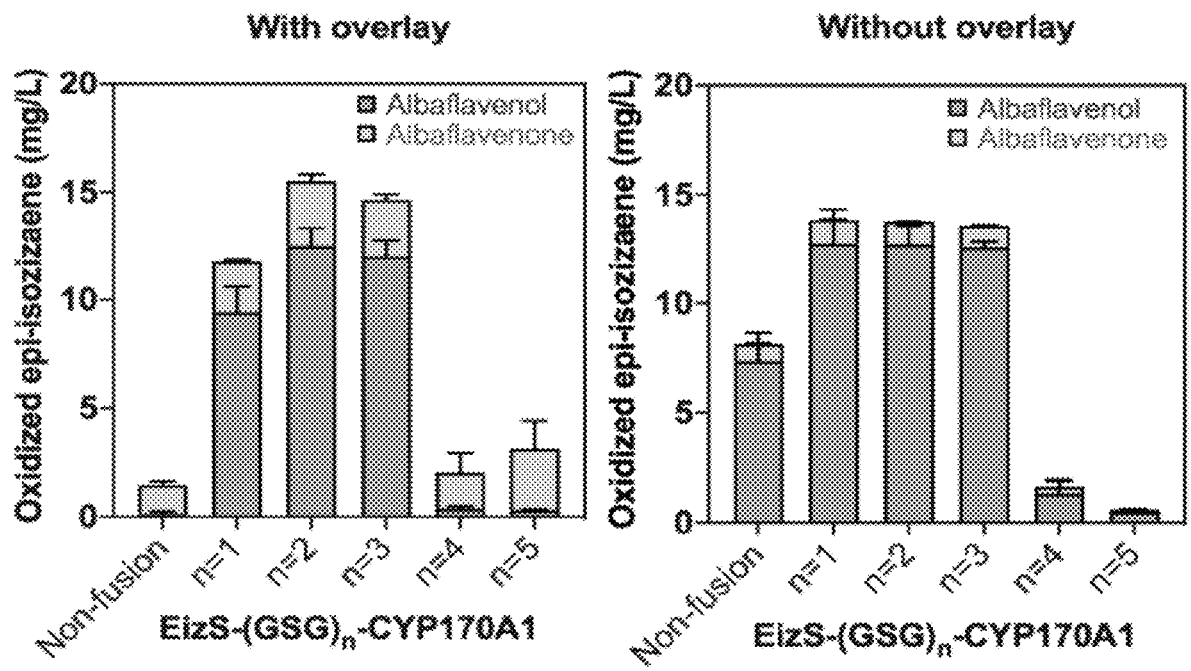
FIG. 7D. Production of oxidized epi-isozizaene with engineered enzyme fusions in *E. coli* DH1. Production of oxidized epi-isozizaene (albaflavenol, albaflavenone) with and without using solvent overlay. Error bars indicate one standard deviation (n=3).

As shown in FIGS. 6A to 6C, the use of solvent overlay generally facilitates 1,8-cineole production, but it does not help hydroxycineole production. For both non-fusion and fusion samples, hydroxycineole productions without using overlay are 1.7-3.4 folds higher than those with an overlay. When nonane overlay is used, all fusions except G4 produce more hydroxycineole than the non-fusion control strain does (FIG. 6C), while producing generally less amount of 1,8-cineole (except for G2), suggesting an inefficient hydroxylation in the non-fusion control strain. When overlay is not used during the production, all 5 strains with fusion protein produce more hydroxycineole than the non-fusion strain (FIG. 6C). The highest hydroxycineole titer is observed from G3 (56 mg/L), which is 3.1-fold higher than that of the non-fusion control (18 mg/L). Unlike the in vitro results, G4 does not show any significant advantage comparing with the other fusions with a different linker length. This indicates that the optimal linker length for a fusion protein may vary from the in vitro and in vivo conditions since the intracellular environment and cell culture medium usually introduces many factors other than the simplified conditions of in vitro reaction. The results also suggest an optimal linker length may play an important role in selecting the best activity of the fusion enzyme, and similar observations have also been reported previously. For example, a fusion of *Marinobacter aquaeolei* P450 (CYP153) and a CYP116B reductase shows 67% improvement of activity by adding two extra amino acids in the linker[26], and in another example, a ten amino-acid linker is found to present the best activity in the fusion of P450$_{cin}$ with its native flavodoxin (CinC)[27].

In addition to the linker length, the orientation of enzymes in a fusion protein is another important factor for the function of a fusion enzyme[12]. Given that G3 shows high production of hydroxycineole at both in vitro and in vivo conditions, GSG$_3$ (3-repeat of Gly-Ser-Gly) is used as the linker length to construct a fusion enzyme with reversely ordered CS and P450$_{cin}$ (i.e. P450$_{cin}$-GSG$_3$-CS) to test hydroxycineole production. Compared with the regular CS-GSG$_3$-P450$_{cin}$ fusion (G3), this reversed fusion produces 51% and 76% less 1,8-cineole and hydroxycineole, respectively when overlay is used (Table 3). These trends are also significant when the overlay is not used. In this case, the reversed fusion produces 80% and 63% less 1,8-cineole and hydroxycineole, respectively, than the fusion with the normal order (Table 3), indicating an inefficient fusion enzyme when CS and P450$_{cin}$ are linked in the reverse order.

TABLE 3

Comparison between CS-P450$_{cin}$ and P450$_{cin}$-CS (fusion with reverse order of enzymes).

| | 1,8-Cineole | | Hydroxycineole | |
|---|---|---|---|---|
| | With overlay | Without overlay | With overlay | Without overlay |
| CS-P450$_{cin}$ (mg/L) | 86 ± 1 | 3 ± 1 | 32 ± 1 | 56 ± 1 |
| P450$_{cin}$-CS (mg/L) | 42 ± 10 | 1 ± 0 | 8 ± 0 | 21 ± 1 |

Production of Oxidized Epi-Isozizaene Using Enzyme Fusions.

The enzyme fusion strategy is applied to the biosynthetic pathway for oxidized epi-isozizaene (FIGS. 7A to 7D) such as albaflavenol and the subsequently oxidized product albaflavenone, a sesquiterpene antibiotic found in *Streptomyces coelicolor* A3(2)[28]. The P450 (CYP170A1) has been identified to catalyze the oxidation of epi-isozizaene in *S. coelicolor* A3(2). Recently, epi-isozizaene biosynthesis was successfully engineered in *E. coli* to produce a novel jet fuel precursor using the MVA pathway[29]. Following the fusion enzyme engineering strategy used in hydroxycineole biosynthesis, fusions for epi-isozizaene synthase (EizS) and CYP170A1 with 1 to 5 repeats of Gly-Ser-Gly (GSG) peptide linker are engineered. An RBS sequence (5'-TTT-CACACAGGAAACAGACC-3') (SEQ ID NO:22) is used for the expression of EizS and CYP170A1 individually in the non-fusion control strain as performed in the 1,8-cineole oxidation case (Table 2).

Compared with the non-fusion control, epi-isozizaene production level is a little lower in the strains with engineered fusion enzymes. On the other hand, the total oxidized products (albaflavenol and albaflavonone) are notably increased in the fusions with shorter linkers (GSG$_{1-3}$) for both conditions with and without overlay (FIGS. 7A to 7D). As expected, the difference is more significant when the overlay is used. The highest oxidized epi-isozizaene level (13 mg/L albaflavenol, 3 mg/L albaflavenone) is observed by the fusion with a $GSG_2$ linker (EizS-$GSG_2$-CYP170A1), which achieves 90- and 2.3-fold increase in albaflavenol and albaflavenone production, respectively.

Conclusions

The functionalization of terpene molecules using cytochrome P450 enzymes presents opportunities for producing diverse bioproducts via the isoprenoid pathway. In this study, an enzyme fusion strategy is developed by directly linking terpene synthase and P450 enzyme together to facilitate the accessibility of terpene molecules to P450 enzymes.

The hydroxylation of a monoterpene 1,8-cineole as a model system is selected and engineered a series of fusion proteins between 1,8-cineole synthase and $P450_{cin}$ (CYP176A1) with different lengths of peptide linker to investigate the hydroxylation of 1,8-cineole. Results show that fusion enzymes increase up to 5.4 and 3.1 folds in hydroxycineole production than non-fused individual enzymes at the in vitro and in vivo conditions, respectively. The enzyme fusion strategy is also applied to the oxidation of a sesquiterpene epi-isozizaene, in which a ~90-fold increase is observed by the fusion in albaflavenol production. Results suggest engineering fusion enzymes between terpene synthase and P450 shows a feasible strategy toward efficient production of oxidized terpenes, especially when a solvent overlay is used to trap terpene molecules and prevent their evaporation during the production.

Methods
Strains and Plasmid Construction

All strains and plasmids used in this study are listed in Table 2. *E. coli* DH1 strain is used for terpene and oxidized terpene production, and *E. coli* DH5α is used for genetic cloning. Genes of CinA ($P450_{cin}$, CYP176A1; GenBank ID: AF456128) and CinC (GenBank ID: AF456128) from *Citrobacter braakii*, and CYP170A1 (sco5223; GenBank ID: NC_003888) from *Streptomyces coelicolor* A3(2) are codon-optimized and synthesized by Integrated DNA Technologies, Inc. (San Diego, Calif.). Fpr (GenBank ID: CP032667) is cloned from *E. coli* genomic DNA. CS from *Streptomyces clavuligerus* is cloned from plasmid JBEI-15065 (Table 2).

Protein Expression and Purification

A plasmid pSKB3 encoding interested proteins with N-terminal His-tag is transformed into *E. coli* BL21 (DE3). BL21 (DE3) strains bearing pSKB3 plasmids are cultured in Lysogeny Broth (LB) medium containing 50 μg/mL kanamycin at 37° C. until the optical density of the culture at 600 nm ($OD_{600}$) reaches to 0.5-0.8. The culture is then supplemented with 0.4 mM isopropyl β-D-1-thiogalactopyranoside (IPTG) for induction and transferred to 18° C. for culturing overnight. Cells are collected by centrifugation and resuspended in 25 mM Tris-HCl (pH 8.0) buffer containing 300 mM NaCl and 10 mM imidazole (pH 8.0). Cells are lysed by sonication and proteins were purified using QIAGEN Ni-NTA Agarose. All purified proteins are desalted in 25 mM Tris-HCl (pH 8.0) buffer containing 100 mM NaCl, and 10% glycerol, and stored at −80° C.

In Vitro Production of Hydroxycineole

Equal mole of purified proteins, 5 μM CS and 5 μM CinA, or 5 μM fusion protein (G1, G2, G3, G4, G5) with 40 μM CinC and 10 μM Fpr are used for the in vitro reaction in 50 mM Tris-HCl buffer (pH 7.4) containing 5 mM $MgCl_2$[17,23]. NADPH (2 mM) and 1 mM geranyl pyrophosphate (GPP, Sigma-Aldrich 19533) are added to start the reaction. The reaction is conducted in a 1.7-mL microcentrifuge tube at 25° C. for 5 hours.

In Vivo Production of Hydroxycineole

*E. coli* DH1 bearing two plasmids is used for hydroxycineole production. Seed cultures of all production strains are prepared by growing single colonies in LB medium containing 30 μg/mL chloramphenicol and 100 μg/mL carbenicillin at 37° C. with 200-rpm shaking for overnight. The seed cultures are diluted in 5 mL EZ-Rich defined medium (Teknova, USA) containing 10 g/L glucose (1%, w/v), 30 μg/mL chloramphenicol, 100 μg/mL carbenicillin, and 0.5 mM IPTG in 50-mL test tubes. 0.5 mL nonane (10%, v/v) is added when required as a solvent overlay. The *E. coli* cell cultures are incubated in rotary shakers (200 rpm) at 30° C. for 48 h.

In Vivo Production of Oxidized Epi-Isozizaene

*E. coli* DH1 bearing two plasmids are used for oxidized epi-isozizaene production. Seed cultures of all production strains are prepared by growing single colonies in LB medium containing 30 μg/mL chloramphenicol and 100 μg/mL carbenicillin at 37° C. with 200-rpm shaking for overnight. The seed cultures are diluted in 5 mL EZ-Rich defined medium (Teknova, USA) containing 10 g/L glucose (1%, w/v), 30 μg/mL chloramphenicol, 100 μg/mL carbenicillin, and 65 mg/L δ-aminolevulinic acid, 0.5 mM IPTG in 50-mL culture tubes. 0.5 mL nonane (10%, v/v) is added when required as a solvent overlay. The *E. coli* cell cultures are incubated in rotary shakers (200 rpm) at 30° C. for 72 hours.

GC-MS Analysis

For 1,8-cineole and hydroxycineole, samples are extracted by an equal volume of ethyl acetate containing β-pinene (5 mg/L) as an internal standard. For epi-isozizaene and oxidized products, samples are extracted by an equal volume of ethyl acetate containing guaiazulene (5 mg/L) as an internal standard. The mixture of ethyl acetate and cell culture is vigorously shaken for 15 min and subsequently centrifuged at 21,130 g for 3 min to separate ethyl acetate from the aqueous phase. The ethyl acetate layer is collected and 1 μL was analyzed by Agilent GC-MS equipped with HP-5 column (Agilent, USA). The GC oven is programmed from 40° C. (held for 3 min) to 295° C. at 15° C./min. The solvent delay is set at 3.4 min. Samples are normalized using internal standard (β-pinene or guaiazulene). 1,8-cineole is quantified using an authentic standard. Hydroxycineole is estimated using total ion chromatogram (TIC) areas and 1,8-cineole standards. Epi-isozizaene and oxidized products (albaflavenol, albaflavenone) are estimated using total ion chromatogram (TIC) areas and caryophyllene standards.

When nonane overlay is used during the production, the solvent delay is set at 6.8 min. Both the nonane overlay and the aqueous phase of the culture re sampled for the GC-MS measurement, respectively. The production titers are the sum of both measured values.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A fusion protein comprising: (a) a terpene synthase (TS) comprising an amino acid sequence having (i) at least 90% identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16, and (ii) the amino acid sequence Asp-Asp-Xaa-Xaa-Asp (DDXXD) (SEQ ID NO:17) or the amino acid sequence Asp-Asp-Xaa-Xaa-Glu (DDXXE) (SEQ ID NO:18), (b) a peptide linker, and (c) a P450 enzyme comprising (i) an amino acid sequence having at least 90% identity with SEQ ID NO:19 or SEQ ID NO:20, and (ii) a CXG motif or EXXR motif.

2. The fusion protein of claim 1, wherein the TS comprises an amino acid sequence having at least 95% identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

3. The fusion protein of claim 1, wherein the TS comprises the amino acid sequence Asp-Asp-Xaa-Xaa-Asp (DDXXD) (SEQ ID NO:17).

4. The fusion protein of claim 1, wherein the TS comprises the amino acid sequence Asp-Asp-Xaa-Xaa-Glu (DDXXE) (SEQ ID NO:18).

5. The fusion protein of claim 1, wherein the P450 enzyme comprises an amino acid sequence having at least 95% identity with SEQ ID NO:19 or SEQ ID NO:20.

6. The fusion protein of claim 1, wherein the P450 enzyme comprises the amino acid sequence FXXGXRXCXG (SEQ ID NO:21).

7. The fusion protein of claim 1, wherein the peptide linker comprises of 0-1000 amino acid residues.

8. The fusion protein of claim 7, wherein the peptide linker comprises of 1-5 repeats of the amino acid sequence GSG.

9. A genetically modified host cell capable of producing a modified terpenes, said genetically modified host cell comprising the fusion protein of claim 1.

10. A nucleic acid comprising a nucleotide sequence encoding the fusion protein of claim 1 operatively linked to a promoter.

11. A vector comprising the nucleic acid of claim 10.

12. A genetically modified host cell capable of producing a modified terpenes, said genetically modified host cell comprising the nucleic acid of claim 10 or a vector of claim 11.

13. The genetically modified host cell of claim 12, wherein the genetically modified host cell is a bacterium.

14. The genetically modified host cell of claim 13, wherein the bacterium is of the genus *Escherichia*, *Enterobacter*, *Azotobacter*, *Erwinia*, *Bacillus*, *Pseudomonas*, *Klebsielia*, *Proteus*, *Salmonella*, *Serratia*, *Shigella*, *Rhizobia*, *Vitreoscilla*, or *Paracoccus*.

15. The genetically modified host cell of claim 12, wherein the genetically modified host cell is a eukaryotic cell.

16. The genetically modified host cell of claim 15, wherein the eukaryotic cell is a yeast.

17. A method for producing a modified terpene comprising: (a) providing the genetically modified host cell of claim 1, or a culture thereof, (b) culturing or growing the genetically modified host cell to produce the modified terpene, (c) and/or extracting or separating the modified terpene from the culture, and (d) and/or introducing a fuel additive to the extracted or separated the modified terpene.

18. A fuel composition comprising: (a) a modified terpene produced by the fusion protein of claim 1; and (b) a fuel additive.

19. The fusion protein of claim 2, wherein the TS comprises an amino acid sequence having at least 99% identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

20. The fusion protein of claim 19, wherein the TS comprises an amino acid sequence comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

21. The fusion protein of claim 5, wherein the P450 enzyme comprises an amino acid sequence having at least 99% identity with SEQ ID NO:19 or SEQ ID NO:20.

22. The fusion protein of claim 21, wherein the P450 enzyme comprises an amino acid sequence comprising SEQ ID NO:19 or SEQ ID NO:20.

* * * * *